US011986234B2

(12) United States Patent
Shelton, IV et al.

(10) Patent No.: US 11,986,234 B2
(45) Date of Patent: May 21, 2024

(54) SURGICAL SYSTEM COMMUNICATION PATHWAYS

(71) Applicant: Cilag GmbH International, Zug (CH)

(72) Inventors: Frederick E. Shelton, IV, Hillsboro, OH (US); Daniel J. Mumaw, Liberty Township, OH (US); Chad E. Eckert, Terrace Park, OH (US); Kevin M. Fiebig, Cincinnati, OH (US); Taylor W. Aronhalt, Loveland, OH (US)

(73) Assignee: Cilag GmbH International, Zug (CH)

( * ) Notice: Subject to any disclaimer, the term of this patent is extended or adjusted under 35 U.S.C. 154(b) by 763 days.

(21) Appl. No.: 16/885,931

(22) Filed: May 28, 2020

(65) Prior Publication Data

US 2021/0196344 A1   Jul. 1, 2021

Related U.S. Application Data

(60) Provisional application No. 62/955,299, filed on Dec. 30, 2019.

(51) Int. Cl.
  *A61B 18/14*   (2006.01)
  *A61B 18/12*   (2006.01)
  (Continued)

(52) U.S. Cl.
  CPC ...... *A61B 18/1445* (2013.01); *A61B 18/1206* (2013.01); *A61B 18/1442* (2013.01);
  (Continued)

(58) Field of Classification Search
  CPC .......... A61B 17/320092; A61B 17/072; A61B 17/068; A61B 17/0686; A61B 17/295; A61B 17/32; A61B 2017/00017; A61B 2017/00398; A61B 2017/07271; A61B 2017/2927; A61B 2017/320095;
  (Continued)

(56) References Cited

U.S. PATENT DOCUMENTS 969,528 A   9/1910  Disbrow
1,570,025 A   1/1926  Young
(Continued)

FOREIGN PATENT DOCUMENTS

CA   2535467 A1   4/1993
CN   2460047 Y   11/2001
(Continued)

OTHER PUBLICATIONS

Covidien Brochure, [Value Analysis Brief], LigaSure Advance™ Pistol Grip, dated Rev. Apr. 2010 (7 pages).
(Continued)

*Primary Examiner* — Khadijeh A Vahdat

(57) ABSTRACT

A surgical system comprising a surgical hub, a surgical instrument, a generator configured to energize an end effector; and a smoke evacuation system configured to remove smoke from a surgical site is disclosed. The surgical instrument comprises the end effector. A control command is passed directly from the surgical hub to the surgical instrument. The surgical instrument is configured to pass the control command received from the surgical hub to the generator and the smoke evacuation system in a daisy-chain manner.

20 Claims, 21 Drawing Sheets

(51) Int. Cl.
　　　*A61B 34/00*　　(2016.01)
　　　*A61B 90/00*　　(2016.01)
　　　*G06F 16/901*　　(2019.01)
　　　*G16H 20/40*　　(2018.01)
　　　*G16H 40/63*　　(2018.01)
　　　*G16H 40/67*　　(2018.01)
　　　*A61B 18/00*　　(2006.01)
　　　*A61B 18/16*　　(2006.01)

(52) U.S. Cl.
　　　CPC .............. *A61B 34/25* (2016.02); *A61B 90/08* (2016.02); *A61B 90/36* (2016.02); *G06F 16/9017* (2019.01); *G16H 20/40* (2018.01); *G16H 40/63* (2018.01); *G16H 40/67* (2018.01); *A61B 2018/00589* (2013.01); *A61B 2018/00601* (2013.01); *A61B 2018/00613* (2013.01); *A61B 2018/0063* (2013.01); *A61B 2018/00684* (2013.01); *A61B 2018/00696* (2013.01); *A61B 2018/00994* (2013.01); *A61B 2018/1253* (2013.01); *A61B 2018/126* (2013.01); *A61B 18/16* (2013.01); *A61B 2218/006* (2013.01)

(58) Field of Classification Search
　　　CPC ........ A61B 2090/061; A61B 17/07207; A61B 18/1445; A61B 2017/00221; A61B 2017/0046; A61B 2017/00725; A61B 2017/07285; A61B 2017/00119; A61B 2017/2929; A61B 2017/00039; A61B 2017/00455; A61B 2017/07278; A61B 2017/00477; A61B 17/320068; A61B 2017/320075; A61B 2017/320094; A61B 17/00234; A61B 2017/00022; A61B 2017/00026; A61B 2017/00154; A61B 2017/00734; A61B 2017/07264; A61B 2017/2825; A61B 2017/320074; A61B 18/1442; A61B 18/1206; A61B 18/14; A61B 18/16; A61B 18/12; A61B 18/1482; A61B 18/149; A61B 18/18; A61B 18/1815; A61B 2018/0063; A61B 2018/00994; A61B 2018/126; A61B 2018/1465; A61B 2018/00083; A61B 2018/00607; A61B 2018/00875; A61B 2018/1253; A61B 2018/00077; A61B 2018/00136; A61B 2018/00404; A61B 2018/00589; A61B 2018/1412; A61B 2018/1455; A61B 2018/00107; A61B 2018/0019; A61B 2018/1452; A61B 2018/0013; A61B 2018/00613; A61B 2018/00702; A61B 2018/00202; A61B 2018/00595; A61B 2018/00636; A61B 2018/00672; A61B 2018/00684; A61B 2018/00696; A61B 2018/0072; A61B 2018/00726; A61B 2018/00732; A61B 2018/00767; A61B 2018/00827; A61B 2018/00892; A61B 2018/00916; A61B 2018/00922; A61B 2018/00928; A61B 2018/00958; A61B 2018/00988; A61B 2018/1405; A61B 90/03; A61B 90/06; A61B 90/36; A61B 90/361; A61B 90/94; A61B 90/96; A61B 2090/0811; A61B 2090/0812; A61B 2090/064; A61B 2090/065; A61B 2090/0803; A61B 2090/0814; A61B 2090/0804; A61B 2090/0806; A61B 2090/0807; A61B 2090/0808

See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |

(56) References Cited

U.S. PATENT DOCUMENTS

| | | |
|---|---|---|
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,739,759 A | 4/1988 | Rexroth et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,926,860 A | 5/1990 | Stice et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,003,693 A | 4/1991 | Atkinson et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,203,380 A | 4/1993 | Chikama |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |

(56) References Cited

U.S. PATENT DOCUMENTS

| | | |
|---|---|---|
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatla |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,536,267 A | 7/1996 | Edwards et al. |
| 5,540,681 A | 7/1996 | Strul et al. |
| 5,540,684 A | 7/1996 | Hassler, Jr. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,638,827 A | 6/1997 | Palmer et al. |
| 5,640,741 A | 6/1997 | Yano |
| D381,077 S | 7/1997 | Hunt |
| 5,647,871 A | 7/1997 | Levine et al. |

(56) References Cited

U.S. PATENT DOCUMENTS

| | | |
|---|---|---|
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,042 A | 12/1997 | Boiarski et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,759,183 A | 6/1998 | VanDusseldorp |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |

(56) References Cited

U.S. PATENT DOCUMENTS

| | | |
|---|---|---|
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,102,909 A | 8/2000 | Chen et al. |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,238,384 B1 | 5/2001 | Peer |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,261,286 B1 | 7/2001 | Goble et al. |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |
| 6,416,469 B1 | 7/2002 | Phung et al. |
| 6,416,486 B1 | 7/2002 | Wampler |
| 6,417,969 B1 | 7/2002 | DeLuca et al. |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,436,129 B1 | 8/2002 | Sharkey et al. |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |

(56) References Cited

U.S. PATENT DOCUMENTS

| | | |
|---|---|---|
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,558,380 B2 | 5/2003 | Lingenfelder et al. |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |

(56) References Cited

U.S. PATENT DOCUMENTS

| | | |
|---|---|---|
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,988,649 B2 | 1/2006 | Shelton, IV et al. |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |

(56) References Cited

U.S. PATENT DOCUMENTS

| | | |
|---|---|---|
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,525,309 B2 | 4/2009 | Sherman et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |

(56) References Cited

U.S. PATENT DOCUMENTS

| | | |
|---|---|---|
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,151 B2 | 9/2010 | Whitman |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,954,682 B2 | 6/2011 | Giordano et al. |

(56) References Cited

U.S. PATENT DOCUMENTS

| | | |
|---|---|---|
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,048,074 B2 | 11/2011 | Masuda |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,216,223 B2 | 7/2012 | Wham et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,308,721 B2 | 11/2012 | Shibata et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |

(56) References Cited

U.S. PATENT DOCUMENTS

| | | |
|---|---|---|
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,360,299 B2 | 1/2013 | Zemlok et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,398,674 B2 | 3/2013 | Prestel |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,036 B2 | 5/2013 | Shelton, IV |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,517,239 B2 | 8/2013 | Scheib et al. |
| 8,518,067 B2 | 8/2013 | Masuda et al. |
| 8,521,331 B2 | 8/2013 | Itkowitz |
| 8,523,043 B2 | 9/2013 | Ullrich et al. |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |

(56) References Cited

U.S. PATENT DOCUMENTS

| | | |
|---|---|---|
| 8,623,016 B2 | 1/2014 | Fischer |
| 8,623,027 B2 | 1/2014 | Price et al. |
| 8,623,040 B2 | 1/2014 | Artsyukhovich et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,702 B1 | 4/2014 | Edwards et al. |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,807,414 B2 | 8/2014 | Ross et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,831,779 B2 | 9/2014 | Ortmaier et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |

(56) References Cited

U.S. PATENT DOCUMENTS

| | | |
|---|---|---|
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,370 B2 | 4/2015 | Reschke et al. |
| 9,017,372 B2 | 4/2015 | Artale et al. |
| 9,023,035 B2 | 5/2015 | Allen, IV et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,691 B2 | 5/2015 | Moua et al. |
| 9,039,692 B2 | 5/2015 | Behnke, II et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,230 B2 | 6/2015 | Morgan et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,083 B2 | 6/2015 | Yates et al. |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,333 B2 | 8/2015 | Konesky et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,266,310 B2 | 2/2016 | Krogdahl et al. |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,283,054 B2 | 3/2016 | Morgan et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,767 B2 | 5/2016 | Koch, Jr. et al. |
| 9,326,787 B2 | 5/2016 | Sanai et al. |
| 9,326,788 B2 | 5/2016 | Batross et al. |
| 9,332,987 B2 | 5/2016 | Leimbach et al. |
| 9,333,025 B2 | 5/2016 | Monson et al. |

(56) References Cited

U.S. PATENT DOCUMENTS

| | | |
|---|---|---|
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,727 B2 | 5/2016 | Leimbach et al. |
| 9,351,754 B2 | 5/2016 | Vakharia et al. |
| 9,352,173 B2 | 5/2016 | Yamada et al. |
| 9,358,003 B2 | 6/2016 | Hall et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,206 B2 | 6/2016 | Vidal et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,014 B2 | 8/2016 | Ingmanson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,438 B2 | 10/2016 | Baber et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,465 B1 | 1/2017 | Liu et al. |
| 9,554,794 B2 | 1/2017 | Baber et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,056 B2 | 3/2017 | Mozdzierz et al. |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,629,623 B2 | 4/2017 | Lytle, IV et al. |
| 9,629,629 B2 | 4/2017 | Leimbach et al. |
| 9,632,573 B2 | 4/2017 | Ogawa et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,230 B2 | 6/2017 | Leimbach et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,094 B2 | 8/2017 | Baber et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,733,663 B2 | 8/2017 | Leimbach et al. |
| 9,737,301 B2 | 8/2017 | Baber et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,757,128 B2 | 9/2017 | Baber et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,169 B2 | 10/2017 | Kimsey et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,626 B2 | 10/2017 | Parihar et al. |
| 9,801,648 B2 | 10/2017 | Houser et al. |

(56) References Cited

U.S. PATENT DOCUMENTS

| | | |
|---|---|---|
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,815,211 B2 | 11/2017 | Cao et al. |
| 9,820,738 B2 | 11/2017 | Lytle, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,826,977 B2 | 11/2017 | Leimbach et al. |
| 9,839,443 B2 | 12/2017 | Brockman et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,877,782 B2 | 1/2018 | Voegele et al. |
| 9,878,184 B2 | 1/2018 | Beaupre |
| 9,883,860 B2 | 2/2018 | Leimbach et al. |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,895,160 B2 | 2/2018 | Fan et al. |
| 9,901,321 B2 | 2/2018 | Harks et al. |
| 9,901,342 B2 | 2/2018 | Shelton, IV et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,642 B2 | 3/2018 | Leimbach et al. |
| 9,913,656 B2 | 3/2018 | Stulen |
| 9,913,680 B2 | 3/2018 | Voegele et al. |
| 9,918,730 B2 | 3/2018 | Trees et al. |
| 9,924,961 B2 | 3/2018 | Shelton, IV et al. |
| 9,925,003 B2 | 3/2018 | Parihar et al. |
| 9,931,118 B2 | 4/2018 | Shelton, IV et al. |
| 9,937,001 B2 | 4/2018 | Nakamura |
| 9,943,309 B2 | 4/2018 | Shelton, IV et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,968,355 B2 | 5/2018 | Shelton, IV et al. |
| 9,974,539 B2 | 5/2018 | Yates et al. |
| 9,987,000 B2 | 6/2018 | Shelton, IV et al. |
| 9,987,033 B2 | 6/2018 | Neurohr et al. |
| 9,993,248 B2 | 6/2018 | Shelton, IV et al. |
| 9,993,258 B2 | 6/2018 | Shelton, IV et al. |
| 9,993,289 B2 | 6/2018 | Sobajima et al. |
| 10,004,497 B2 | 6/2018 | Overmyer et al. |
| 10,004,501 B2 | 6/2018 | Shelton, IV et al. |
| 10,004,526 B2 | 6/2018 | Dycus et al. |
| 10,004,527 B2 | 6/2018 | Gee et al. |
| D822,206 S | 7/2018 | Shelton, IV et al. |
| 10,010,339 B2 | 7/2018 | Witt et al. |
| 10,010,341 B2 | 7/2018 | Houser et al. |
| 10,013,049 B2 | 7/2018 | Leimbach et al. |
| 10,016,199 B2 | 7/2018 | Baber et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| D826,405 S | 8/2018 | Shelton, IV et al. |
| 10,039,588 B2 | 8/2018 | Harper et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,052,044 B2 | 8/2018 | Shelton, IV et al. |
| 10,052,102 B2 | 8/2018 | Baxter, III et al. |
| 10,070,916 B2 | 9/2018 | Artale |
| 10,080,609 B2 | 9/2018 | Hancock et al. |
| 10,085,748 B2 | 10/2018 | Morgan et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,347 B2 | 10/2018 | Weisshaupt et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,679 B2 | 10/2018 | Baber et al. |
| 10,111,699 B2 | 10/2018 | Boudreaux |
| 10,111,703 B2 | 10/2018 | Cosman, Jr. et al. |
| 10,117,649 B2 | 11/2018 | Baxter, III et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,154,848 B2 | 12/2018 | Chernov et al. |
| 10,154,852 B2 | 12/2018 | Conlon et al. |
| 10,159,483 B2 | 12/2018 | Beckman et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,178,992 B2 | 1/2019 | Wise et al. |
| 10,179,022 B2 | 1/2019 | Yates et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,455 B2 | 1/2019 | Hancock et al. |
| 10,194,907 B2 | 2/2019 | Marczyk et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,206,676 B2 | 2/2019 | Shelton, IV |
| 10,226,250 B2 | 3/2019 | Beckman et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,095 B2 | 4/2019 | Boudreaux |
| 10,245,097 B2 | 4/2019 | Honda et al. |
| 10,245,104 B2 | 4/2019 | McKenna et al. |
| 10,251,664 B2 | 4/2019 | Shelton, IV et al. |
| 10,258,331 B2 | 4/2019 | Shelton, IV et al. |
| 10,258,505 B2 | 4/2019 | Ovchinnikov |

(56) References Cited

U.S. PATENT DOCUMENTS

| | | |
|---|---|---|
| 10,263,171 B2 | 4/2019 | Wiener et al. |
| 10,265,068 B2 | 4/2019 | Harris et al. |
| 10,265,117 B2 | 4/2019 | Wiener et al. |
| 10,265,118 B2 | 4/2019 | Gerhardt |
| 10,271,840 B2 | 4/2019 | Sapre |
| 10,271,851 B2 | 4/2019 | Shelton, IV et al. |
| D847,989 S | 5/2019 | Shelton, IV et al. |
| 10,278,721 B2 | 5/2019 | Dietz et al. |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,704 B2 | 5/2019 | Harris et al. |
| 10,299,810 B2 | 5/2019 | Robertson et al. |
| 10,299,821 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,579 B2 | 6/2019 | Chowaniec et al. |
| 10,314,582 B2 | 6/2019 | Shelton, IV et al. |
| 10,314,638 B2 | 6/2019 | Gee et al. |
| 10,321,907 B2 | 6/2019 | Shelton, IV et al. |
| 10,321,950 B2 | 6/2019 | Yates et al. |
| D854,151 S | 7/2019 | Shelton, IV et al. |
| 10,335,149 B2 | 7/2019 | Baxter, III et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,543 B2 | 7/2019 | Shelton, IV et al. |
| 10,342,602 B2 | 7/2019 | Strobl et al. |
| 10,342,606 B2 | 7/2019 | Cosman et al. |
| 10,342,623 B2 | 7/2019 | Huelman et al. |
| 10,348,941 B2 | 7/2019 | Elliot, Jr. et al. |
| 10,349,999 B2 | 7/2019 | Yates et al. |
| 10,350,016 B2 | 7/2019 | Burbank et al. |
| 10,350,025 B1 | 7/2019 | Loyd et al. |
| 10,357,246 B2 | 7/2019 | Shelton, IV et al. |
| 10,357,247 B2 | 7/2019 | Shelton, IV et al. |
| 10,357,303 B2 | 7/2019 | Conlon et al. |
| 10,363,084 B2 | 7/2019 | Friedrichs |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,376,305 B2 | 8/2019 | Yates et al. |
| 10,390,841 B2 | 8/2019 | Shelton, IV et al. |
| 10,398,439 B2 | 9/2019 | Cabrera et al. |
| 10,398,466 B2 | 9/2019 | Stulen et al. |
| 10,398,497 B2 | 9/2019 | Batross et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,413,352 B2 | 9/2019 | Thomas et al. |
| 10,413,353 B2 | 9/2019 | Kerr et al. |
| 10,420,552 B2 | 9/2019 | Shelton, IV et al. |
| 10,420,579 B2 | 9/2019 | Wiener et al. |
| 10,420,607 B2 | 9/2019 | Woloszko et al. |
| D865,175 S | 10/2019 | Widenhouse et al. |
| 10,426,471 B2 | 10/2019 | Shelton, IV et al. |
| 10,426,507 B2 | 10/2019 | Wiener et al. |
| 10,426,546 B2 | 10/2019 | Graham et al. |
| 10,426,978 B2 | 10/2019 | Akagane |
| 10,433,837 B2 | 10/2019 | Worthington et al. |
| 10,433,849 B2 | 10/2019 | Shelton, IV et al. |
| 10,433,865 B2 | 10/2019 | Witt et al. |
| 10,433,866 B2 | 10/2019 | Witt et al. |
| 10,433,900 B2 | 10/2019 | Harris et al. |
| 10,441,279 B2 | 10/2019 | Shelton, IV et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,448,986 B2 | 10/2019 | Zikorus et al. |
| 10,456,140 B2 | 10/2019 | Shelton, IV et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,470,762 B2 | 11/2019 | Leimbach et al. |
| 10,470,764 B2 | 11/2019 | Baxter, III et al. |
| 10,478,182 B2 | 11/2019 | Taylor |
| 10,478,190 B2 | 11/2019 | Miller et al. |
| 10,485,542 B2 | 11/2019 | Shelton, IV et al. |
| 10,485,543 B2 | 11/2019 | Shelton, IV et al. |
| 10,485,607 B2 | 11/2019 | Strobl et al. |
| D869,655 S | 12/2019 | Shelton, IV et al. |
| 10,492,785 B2 | 12/2019 | Overmyer et al. |
| 10,492,849 B2 | 12/2019 | Juergens et al. |
| 10,499,914 B2 | 12/2019 | Huang et al. |
| 10,507,033 B2 | 12/2019 | Dickerson et al. |
| 10,512,795 B2 | 12/2019 | Voegele et al. |
| 10,517,595 B2 | 12/2019 | Hunter et al. |
| 10,517,596 B2 | 12/2019 | Hunter et al. |
| 10,517,627 B2 | 12/2019 | Timm et al. |
| 10,524,787 B2 | 1/2020 | Shelton, IV et al. |
| 10,524,789 B2 | 1/2020 | Swayze et al. |
| 10,524,854 B2 | 1/2020 | Woodruff et al. |
| 10,524,872 B2 | 1/2020 | Stewart et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,543,008 B2 | 1/2020 | Vakharia et al. |
| 10,548,504 B2 | 2/2020 | Shelton, IV et al. |
| 10,548,655 B2 | 2/2020 | Scheib et al. |
| 10,555,769 B2 | 2/2020 | Worrell et al. |
| 10,561,560 B2 | 2/2020 | Boutoussov et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,892 B2 | 3/2020 | Danziger et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,929 B2 | 3/2020 | Boudreaux et al. |
| 10,595,930 B2 | 3/2020 | Scheib et al. |
| 10,603,036 B2 | 3/2020 | Hunter et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,420 B2 | 4/2020 | Shelton, IV et al. |
| 10,617,464 B2 | 4/2020 | Duppuis |
| 10,624,635 B2 | 4/2020 | Harris et al. |
| 10,624,691 B2 | 4/2020 | Wiener et al. |
| 10,631,858 B2 | 4/2020 | Burbank |
| 10,631,859 B2 | 4/2020 | Shelton, IV et al. |
| 10,631,928 B2 | 4/2020 | Basu et al. |
| 10,632,630 B2 | 4/2020 | Cao et al. |
| RE47,996 E | 5/2020 | Turner et al. |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,639,092 B2 | 5/2020 | Corbett et al. |
| 10,639,098 B2 | 5/2020 | Cosman et al. |
| 10,646,269 B2 | 5/2020 | Worrell et al. |
| 10,646,292 B2 | 5/2020 | Solomon et al. |
| 10,653,413 B2 | 5/2020 | Worthington et al. |
| 10,660,692 B2 | 5/2020 | Lesko et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,677,764 B2 | 6/2020 | Ross et al. |

(56) References Cited

U.S. PATENT DOCUMENTS

| | | |
|---|---|---|
| 10,682,136 B2 | 6/2020 | Harris et al. |
| 10,682,138 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,688,321 B2 | 6/2020 | Wiener et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,119 B2 | 6/2020 | Smith |
| 10,702,270 B2 | 7/2020 | Shelton, IV et al. |
| 10,702,329 B2 | 7/2020 | Strobl et al. |
| 10,709,446 B2 | 7/2020 | Harris et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,233 B2 | 7/2020 | Wellman |
| D893,717 S | 8/2020 | Messerly et al. |
| 10,729,458 B2 | 8/2020 | Stoddard et al. |
| 10,729,494 B2 | 8/2020 | Parihar et al. |
| 10,736,629 B2 | 8/2020 | Shelton, IV et al. |
| 10,736,685 B2 | 8/2020 | Wiener et al. |
| 10,751,108 B2 | 8/2020 | Yates et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,294 B2 | 9/2020 | Jones |
| 10,765,427 B2 | 9/2020 | Shelton, IV et al. |
| 10,765,470 B2 | 9/2020 | Yates et al. |
| 10,772,629 B2 | 9/2020 | Shelton, IV et al. |
| 10,772,630 B2 | 9/2020 | Wixey |
| 10,779,821 B2 | 9/2020 | Harris et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,845 B2 | 9/2020 | Timm et al. |
| 10,779,849 B2 | 9/2020 | Shelton, IV et al. |
| 10,779,879 B2 | 9/2020 | Yates et al. |
| 10,786,253 B2 | 9/2020 | Shelton, IV et al. |
| 10,786,276 B2 | 9/2020 | Hirai et al. |
| 10,806,454 B2 | 10/2020 | Kopp |
| 10,813,638 B2 | 10/2020 | Shelton, IV et al. |
| 10,820,938 B2 | 11/2020 | Fischer et al. |
| 10,828,032 B2 | 11/2020 | Leimbach et al. |
| 10,828,058 B2 | 11/2020 | Shelton, IV et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,307 B2 | 11/2020 | Shelton, IV et al. |
| 10,842,492 B2 | 11/2020 | Shelton, IV et al. |
| 10,842,523 B2 | 11/2020 | Shelton, IV et al. |
| 10,842,563 B2 | 11/2020 | Gilbert et al. |
| D906,355 S | 12/2020 | Messerly et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,856,896 B2 | 12/2020 | Eichmann et al. |
| 10,856,929 B2 | 12/2020 | Yates et al. |
| 10,856,934 B2 | 12/2020 | Trees et al. |
| 10,874,465 B2 | 12/2020 | Weir et al. |
| D908,216 S | 1/2021 | Messerly et al. |
| 10,881,399 B2 | 1/2021 | Shelton, IV et al. |
| 10,881,401 B2 | 1/2021 | Baber et al. |
| 10,881,409 B2 | 1/2021 | Cabrera |
| 10,881,449 B2 | 1/2021 | Boudreaux et al. |
| 10,888,322 B2 | 1/2021 | Morgan et al. |
| 10,888,347 B2 | 1/2021 | Witt et al. |
| 10,893,863 B2 | 1/2021 | Shelton, IV et al. |
| 10,893,864 B2 | 1/2021 | Harris et al. |
| 10,893,883 B2 | 1/2021 | Dannaher |
| 10,898,186 B2 | 1/2021 | Bakos et al. |
| 10,898,256 B2 | 1/2021 | Yates et al. |
| 10,912,559 B2 | 2/2021 | Harris et al. |
| 10,912,580 B2 | 2/2021 | Green et al. |
| 10,912,603 B2 | 2/2021 | Boudreaux et al. |
| 10,918,385 B2 | 2/2021 | Overmyer et al. |
| 10,925,659 B2 | 2/2021 | Shelton, IV et al. |
| 10,926,022 B2 | 2/2021 | Hickey et al. |
| D914,878 S | 3/2021 | Shelton, IV et al. |
| 10,932,766 B2 | 3/2021 | Tesar et al. |
| 10,932,847 B2 | 3/2021 | Yates et al. |
| 10,945,727 B2 | 3/2021 | Shelton, IV et al. |
| 10,952,788 B2 | 3/2021 | Asher et al. |
| 10,959,727 B2 | 3/2021 | Hunter et al. |
| 10,966,741 B2 | 4/2021 | Illizaliturri-Sanchez et al. |
| 10,966,747 B2 | 4/2021 | Worrell et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,980,536 B2 | 4/2021 | Weaner et al. |
| 10,987,105 B2 | 4/2021 | Cappola et al. |
| 10,987,123 B2 | 4/2021 | Weir et al. |
| 10,987,156 B2 | 4/2021 | Trees et al. |
| 10,993,715 B2 | 5/2021 | Shelton, IV et al. |
| 10,993,716 B2 | 5/2021 | Shelton, IV et al. |
| 10,993,763 B2 | 5/2021 | Batross et al. |
| 11,000,278 B2 | 5/2021 | Shelton, IV et al. |
| 11,000,279 B2 | 5/2021 | Shelton, IV et al. |
| 11,020,114 B2 | 6/2021 | Shelton, IV et al. |
| 11,020,140 B2 | 6/2021 | Gee et al. |
| 11,033,322 B2 | 6/2021 | Wiener et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,045,275 B2 | 6/2021 | Boudreaux et al. |
| 11,051,840 B2 | 7/2021 | Shelton, IV et al. |
| 11,051,873 B2 | 7/2021 | Wiener et al. |
| 11,058,424 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,064,997 B2 | 7/2021 | Shelton, IV et al. |
| 11,065,048 B2 | 7/2021 | Messerly et al. |
| 11,083,455 B2 | 8/2021 | Shelton, IV et al. |
| 11,083,458 B2 | 8/2021 | Harris et al. |
| 11,090,048 B2 | 8/2021 | Fanelli et al. |
| 11,090,049 B2 | 8/2021 | Bakos et al. |
| 11,090,104 B2 | 8/2021 | Wiener et al. |
| 11,096,688 B2 | 8/2021 | Shelton, IV et al. |
| 11,096,752 B2 | 8/2021 | Stulen et al. |
| 11,109,866 B2 | 9/2021 | Shelton, IV et al. |
| 11,129,611 B2 | 9/2021 | Shelton, IV et al. |
| 11,129,666 B2 | 9/2021 | Messerly et al. |
| 11,129,669 B2 | 9/2021 | Stulen et al. |
| 11,129,670 B2 | 9/2021 | Shelton, IV et al. |
| 11,134,942 B2 | 10/2021 | Harris et al. |
| 11,134,978 B2 | 10/2021 | Shelton, IV et al. |
| 11,141,154 B2 | 10/2021 | Shelton, IV et al. |
| 11,141,213 B2 | 10/2021 | Yates et al. |
| 11,147,551 B2 | 10/2021 | Shelton, IV |
| 11,147,553 B2 | 10/2021 | Shelton, IV |
| 11,160,551 B2 | 11/2021 | Shelton, IV et al. |
| 11,166,716 B2 | 11/2021 | Shelton, IV et al. |
| 11,172,929 B2 | 11/2021 | Shelton, IV |
| 11,179,155 B2 | 11/2021 | Shelton, IV et al. |
| 11,179,173 B2 | 11/2021 | Price et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,670 B2 | 12/2021 | Worrell et al. |
| 11,207,065 B2 | 12/2021 | Harris et al. |
| 11,207,067 B2 | 12/2021 | Shelton, IV et al. |
| 11,213,293 B2 | 1/2022 | Worthington et al. |
| 11,213,294 B2 | 1/2022 | Shelton, IV et al. |
| 11,219,453 B2 | 1/2022 | Shelton, IV et al. |
| 11,224,426 B2 | 1/2022 | Shelton, IV et al. |
| 11,224,497 B2 | 1/2022 | Shelton, IV et al. |
| 11,229,437 B2 | 1/2022 | Shelton, IV et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |

(56) References Cited

U.S. PATENT DOCUMENTS

| | | |
|---|---|---|
| 11,234,698 B2 | 2/2022 | Shelton, IV et al. |
| 11,241,235 B2 | 2/2022 | Shelton, IV et al. |
| 11,246,592 B2 | 2/2022 | Shelton, IV et al. |
| 11,246,625 B2 | 2/2022 | Kane et al. |
| 11,246,678 B2 | 2/2022 | Shelton, IV et al. |
| 11,253,256 B2 | 2/2022 | Harris et al. |
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,266,430 B2 | 3/2022 | Clauda et al. |
| 11,272,931 B2 | 3/2022 | Boudreaux et al. |
| 11,278,280 B2 | 3/2022 | Shelton, IV et al. |
| 11,284,890 B2 | 3/2022 | Nalagatla et al. |
| 11,291,440 B2 | 4/2022 | Harris et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,451 B2 | 4/2022 | Shelton, IV |
| 11,298,127 B2 | 4/2022 | Shelton, IV |
| 11,298,129 B2 | 4/2022 | Bakos et al. |
| 11,298,130 B2 | 4/2022 | Bakos et al. |
| 11,304,695 B2 | 4/2022 | Shelton, IV et al. |
| 11,304,696 B2 | 4/2022 | Shelton, IV et al. |
| 11,304,699 B2 | 4/2022 | Shelton, IV et al. |
| 11,311,306 B2 | 4/2022 | Shelton, IV et al. |
| 11,311,326 B2 | 4/2022 | Boudreaux |
| 11,311,342 B2 | 4/2022 | Parihar et al. |
| D950,728 S | 5/2022 | Bakos et al. |
| D952,144 S | 5/2022 | Boudreaux |
| 11,317,915 B2 | 5/2022 | Boudreaux et al. |
| 11,324,503 B2 | 5/2022 | Shelton, IV et al. |
| 11,324,527 B2 | 5/2022 | Aldridge et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,747 B2 | 5/2022 | Voegele et al. |
| 11,344,362 B2 | 5/2022 | Yates et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,369,377 B2 | 6/2022 | Boudreaux et al. |
| 11,376,098 B2 | 7/2022 | Shelton, IV et al. |
| 11,382,642 B2 | 7/2022 | Robertson et al. |
| 11,389,161 B2 | 7/2022 | Shelton, IV et al. |
| 11,389,164 B2 | 7/2022 | Yates et al. |
| 11,399,837 B2 | 8/2022 | Shelton, IV et al. |
| 11,399,855 B2 | 8/2022 | Boudreaux et al. |
| 11,406,382 B2 | 8/2022 | Shelton, IV et al. |
| 11,406,386 B2 | 8/2022 | Baber et al. |
| 11,413,060 B2 | 8/2022 | Faller et al. |
| 11,419,606 B2 | 8/2022 | Overmyer et al. |
| 11,419,626 B2 | 8/2022 | Timm et al. |
| 11,424,027 B2 | 8/2022 | Shelton, IV |
| 11,426,167 B2 | 8/2022 | Shelton, IV et al. |
| 11,426,191 B2 | 8/2022 | Vakharia et al. |
| D964,564 S | 9/2022 | Boudreaux |
| 11,446,029 B2 | 9/2022 | Shelton, IV et al. |
| 11,452,525 B2 | 9/2022 | Shelton, IV et al. |
| 11,464,511 B2 | 10/2022 | Timm et al. |
| 11,464,512 B2 | 10/2022 | Shelton, IV et al. |
| 11,464,601 B2 | 10/2022 | Shelton, IV et al. |
| 11,471,155 B2 | 10/2022 | Shelton, IV et al. |
| 11,471,156 B2 | 10/2022 | Shelton, IV et al. |
| 11,471,206 B2 | 10/2022 | Henderson et al. |
| 11,471,209 B2 | 10/2022 | Yates et al. |
| 11,478,242 B2 | 10/2022 | Shelton, IV et al. |
| 11,484,310 B2 | 11/2022 | Shelton, IV et al. |
| 11,497,547 B2 | 11/2022 | McKenna et al. |
| 11,504,122 B2 | 11/2022 | Shelton, IV et al. |
| 11,517,309 B2 | 12/2022 | Bakos et al. |
| 11,529,137 B2 | 12/2022 | Shelton, IV et al. |
| 11,529,139 B2 | 12/2022 | Shelton, IV et al. |
| 11,553,971 B2 | 1/2023 | Shelton, IV et al. |
| 11,559,304 B2 | 1/2023 | Boudreaux et al. |
| 11,559,307 B2 | 1/2023 | Shelton, IV et al. |
| 11,559,308 B2 | 1/2023 | Yates et al. |
| 11,559,347 B2 | 1/2023 | Wiener et al. |
| 11,571,210 B2 | 2/2023 | Shelton, IV et al. |
| 11,576,672 B2 | 2/2023 | Shelton, IV et al. |
| 11,576,677 B2 | 2/2023 | Shelton, IV et al. |
| 11,583,306 B2 | 2/2023 | Olson et al. |
| 11,589,865 B2 | 2/2023 | Shelton, IV et al. |
| 11,589,888 B2 | 2/2023 | Shelton, IV et al. |
| 11,589,916 B2 | 2/2023 | Shelton, IV et al. |
| 11,607,219 B2 | 3/2023 | Shelton, IV et al. |
| 11,638,587 B2 | 5/2023 | Shelton, IV et al. |
| 11,653,920 B2 | 5/2023 | Shelton, IV et al. |
| 11,659,023 B2 | 5/2023 | Shelton, IV et al. |
| 11,660,089 B2 | 5/2023 | Shelton, IV et al. |
| 11,660,163 B2 | 5/2023 | Shelton, IV et al. |
| 11,666,368 B2 | 6/2023 | Henderson et al. |
| 11,666,375 B2 | 6/2023 | Scheib et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0032452 A1 | 3/2002 | Tierney et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0123749 A1 | 9/2002 | Jain |
| 2002/0133152 A1 | 9/2002 | Strul |
| 2002/0151884 A1 | 10/2002 | Hoey et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177373 A1 | 11/2002 | Shibata et al. |
| 2002/0177862 A1 | 11/2002 | Aranyi et al. |
| 2003/0009164 A1 | 1/2003 | Woloszko et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0073981 A1 | 4/2003 | Whitman et al. |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0176778 A1 | 9/2003 | Messing et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0208186 A1 | 11/2003 | Moreyra |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0094597 A1 | 5/2004 | Whitman et al. |

(56) References Cited

U.S. PATENT DOCUMENTS

| | | |
|---|---|---|
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0143263 A1 | 7/2004 | Schechter et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0181242 A1 | 9/2004 | Stack et al. |
| 2004/0193150 A1 | 9/2004 | Sharkey et al. |
| 2004/0193153 A1 | 9/2004 | Sartor et al. |
| 2004/0193212 A1 | 9/2004 | Taniguchi et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0171533 A1 | 8/2005 | Latterell et al. |
| 2005/0177184 A1 | 8/2005 | Easley |
| 2005/0182339 A1 | 8/2005 | Lee et al. |
| 2005/0187576 A1 | 8/2005 | Whitman et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0142656 A1 | 6/2006 | Malackowski et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217700 A1 | 9/2006 | Garito et al. |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0259102 A1* | 11/2006 | Slatkine ............... A61B 17/205 607/88 |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0129726 A1 | 6/2007 | Eder et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015473 A1 | 1/2008 | Shimizu |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0046122 A1 | 2/2008 | Manzo et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |

(56) References Cited

U.S. PATENT DOCUMENTS

| | | |
|---|---|---|
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0161809 A1 | 7/2008 | Schmitz et al. |
| 2008/0167670 A1 | 7/2008 | Shelton et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0036913 A1 | 2/2009 | Wiener et al. |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088745 A1 | 4/2009 | Hushka et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0105750 A1 | 4/2009 | Price et al. |
| 2009/0112206 A1 | 4/2009 | Dumbauld et al. |
| 2009/0118751 A1 | 5/2009 | Wiener et al. |
| 2009/0131885 A1 | 5/2009 | Akahoshi |
| 2009/0131934 A1 | 5/2009 | Odom et al. |
| 2009/0138025 A1 | 5/2009 | Stahler et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0182333 A1 | 7/2009 | Eder et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |
| 2009/0248022 A1 | 10/2009 | Falkenstein et al. |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0036373 A1* | 2/2010 | Ward ................ A61B 18/1206 606/34 |
| 2010/0042093 A9 | 2/2010 | Wham et al. |
| 2010/0049180 A1 | 2/2010 | Wells et al. |
| 2010/0057081 A1 | 3/2010 | Hanna |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0145335 A1 | 6/2010 | Johnson et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0193566 A1 | 8/2010 | Scheib et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0225209 A1 | 9/2010 | Goldberg et al. |
| 2010/0228249 A1 | 9/2010 | Mohr et al. |
| 2010/0228250 A1 | 9/2010 | Brogna |
| 2010/0234906 A1 | 9/2010 | Koh |
| 2010/0256635 A1 | 10/2010 | McKenna et al. |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0305564 A1 | 12/2010 | Livneh |
| 2010/0331742 A1 | 12/2010 | Masuda |
| 2010/0331871 A1 | 12/2010 | Nield et al. |
| 2011/0004233 A1 | 1/2011 | Muir et al. |
| 2011/0015632 A1 | 1/2011 | Artale |
| 2011/0015650 A1 | 1/2011 | Choi et al. |
| 2011/0022032 A1 | 1/2011 | Zemlok et al. |
| 2011/0028964 A1 | 2/2011 | Edwards |
| 2011/0071523 A1 | 3/2011 | Dickhans |
| 2011/0082494 A1 | 4/2011 | Kerr et al. |
| 2011/0106141 A1 | 5/2011 | Nakamura |
| 2011/0112400 A1 | 5/2011 | Emery et al. |
| 2011/0125149 A1* | 5/2011 | El-Galley ............ A61B 17/00 606/34 |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0238079 A1 | 9/2011 | Hannaford et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |

(56) References Cited

U.S. PATENT DOCUMENTS

| | | |
|---|---|---|
| 2012/0022526 A1 | 1/2012 | Aldridge et al. |
| 2012/0022528 A1 | 1/2012 | White et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101493 A1 | 4/2012 | Masuda et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136347 A1 | 5/2012 | Brustad et al. |
| 2012/0136386 A1 | 5/2012 | Kishida et al. |
| 2012/0143182 A1 | 6/2012 | Ullrich et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0193396 A1 | 8/2012 | Zemlok et al. |
| 2012/0211542 A1 | 8/2012 | Racenet |
| 2012/0226266 A1 | 9/2012 | Ghosal et al. |
| 2012/0234893 A1 | 9/2012 | Schuckmann et al. |
| 2012/0253328 A1 | 10/2012 | Cunningham et al. |
| 2012/0253329 A1 | 10/2012 | Zemlok et al. |
| 2012/0265241 A1 | 10/2012 | Hart et al. |
| 2012/0296239 A1 | 11/2012 | Chernov et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0071282 A1 | 3/2013 | Fry |
| 2013/0085510 A1 | 4/2013 | Stefanchik et al. |
| 2013/0103031 A1 | 4/2013 | Garrison |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0190760 A1 | 7/2013 | Allen, IV et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0264369 A1 | 10/2013 | Whitman |
| 2013/0267874 A1 | 10/2013 | Marcotte et al. |
| 2013/0277410 A1 | 10/2013 | Fernandez et al. |
| 2013/0296843 A1 | 11/2013 | Boudreaux et al. |
| 2013/0321425 A1 | 12/2013 | Greene et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005663 A1 | 1/2014 | Heard et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0077426 A1 | 3/2014 | Park |
| 2014/0107538 A1 | 4/2014 | Wiener et al. |
| 2014/0121569 A1 | 5/2014 | Schafer et al. |
| 2014/0135804 A1 | 5/2014 | Weisenburgh, II et al. |
| 2014/0163541 A1 | 6/2014 | Shelton, IV et al. |
| 2014/0163549 A1 | 6/2014 | Yates et al. |
| 2014/0180274 A1 | 6/2014 | Kabaya et al. |
| 2014/0180310 A1 | 6/2014 | Blumenkranz et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207124 A1 | 7/2014 | Aldridge et al. |
| 2014/0207135 A1 | 7/2014 | Winter |
| 2014/0221994 A1 | 8/2014 | Reschke |
| 2014/0236152 A1 | 8/2014 | Walberg et al. |
| 2014/0246475 A1 | 9/2014 | Hall et al. |
| 2014/0249557 A1 | 9/2014 | Koch, Jr. et al. |
| 2014/0263541 A1 | 9/2014 | Leimbach et al. |
| 2014/0263552 A1 | 9/2014 | Hall et al. |
| 2014/0276794 A1 | 9/2014 | Batchelor et al. |
| 2014/0276797 A1 | 9/2014 | Batchelor et al. |
| 2014/0276798 A1 | 9/2014 | Batchelor et al. |
| 2014/0303605 A1 | 10/2014 | Boyden et al. |
| 2014/0303612 A1 | 10/2014 | Williams |
| 2014/0357984 A1 | 12/2014 | Wallace et al. |
| 2014/0373003 A1 | 12/2014 | Grez et al. |
| 2015/0014392 A1 | 1/2015 | Williams et al. |
| 2015/0025528 A1 | 1/2015 | Arts |
| 2015/0032150 A1 | 1/2015 | Ishida et al. |
| 2015/0048140 A1 | 2/2015 | Penna et al. |
| 2015/0066027 A1 | 3/2015 | Garrison et al. |
| 2015/0080876 A1 | 3/2015 | Worrell et al. |
| 2015/0080887 A1 | 3/2015 | Sobajima et al. |
| 2015/0080889 A1 | 3/2015 | Cunningham et al. |
| 2015/0088122 A1 | 3/2015 | Jensen |
| 2015/0100056 A1 | 4/2015 | Nakamura |
| 2015/0112335 A1 | 4/2015 | Boudreaux et al. |
| 2015/0119901 A1 | 4/2015 | Steege |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0230796 A1 | 8/2015 | Calderoni |
| 2015/0238260 A1 | 8/2015 | Nau, Jr. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272657 A1 | 10/2015 | Yates et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2015/0317899 A1 | 11/2015 | Dumbauld et al. |
| 2015/0351765 A1 | 12/2015 | Valentine et al. |
| 2015/0351857 A1 | 12/2015 | Vander Poorten et al. |
| 2015/0374430 A1 | 12/2015 | Weiler et al. |
| 2015/0374457 A1 | 12/2015 | Colby |
| 2016/0000437 A1 | 1/2016 | Giordano et al. |
| 2016/0038228 A1 | 2/2016 | Daniel et al. |
| 2016/0044841 A1 | 2/2016 | Chamberlain |
| 2016/0045248 A1 | 2/2016 | Unger et al. |
| 2016/0051314 A1 | 2/2016 | Batchelor et al. |
| 2016/0051316 A1 | 2/2016 | Boudreaux |
| 2016/0066913 A1 | 3/2016 | Swayze et al. |
| 2016/0120601 A1 | 5/2016 | Boudreaux et al. |
| 2016/0175025 A1 | 6/2016 | Strobl |
| 2016/0175029 A1 | 6/2016 | Witt et al. |
| 2016/0206342 A1 | 7/2016 | Robertson et al. |
| 2016/0228171 A1 | 8/2016 | Boudreaux |
| 2016/0249910 A1 | 9/2016 | Shelton, IV et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0317216 A1 | 11/2016 | Hermes et al. |
| 2016/0331455 A1 | 11/2016 | Hancock et al. |
| 2016/0358849 A1 | 12/2016 | Jur et al. |
| 2017/0020614 A1 | 1/2017 | Jackson et al. |
| 2017/0065331 A1 | 3/2017 | Mayer et al. |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0164997 A1 | 6/2017 | Johnson et al. |
| 2017/0189095 A1 | 7/2017 | Danziger et al. |
| 2017/0202595 A1 | 7/2017 | Shelton, IV |

(56) References Cited

U.S. PATENT DOCUMENTS

| | | |
|---|---|---|
| 2017/0209145 A1 | 7/2017 | Swayze et al. |
| 2017/0224332 A1 | 8/2017 | Hunter et al. |
| 2017/0224405 A1 | 8/2017 | Takashino et al. |
| 2017/0231628 A1 | 8/2017 | Shelton, IV et al. |
| 2017/0281186 A1 | 10/2017 | Shelton, IV et al. |
| 2017/0296169 A1 | 10/2017 | Yates et al. |
| 2017/0296177 A1 | 10/2017 | Harris et al. |
| 2017/0296180 A1 | 10/2017 | Harris et al. |
| 2017/0303954 A1 | 10/2017 | Ishii |
| 2017/0312018 A1 | 11/2017 | Trees et al. |
| 2017/0325874 A1 | 11/2017 | Noack et al. |
| 2017/0333073 A1 | 11/2017 | Faller et al. |
| 2017/0348043 A1 | 12/2017 | Wang et al. |
| 2017/0348044 A1 | 12/2017 | Wang et al. |
| 2017/0367772 A1 | 12/2017 | Gunn et al. |
| 2018/0014872 A1 | 1/2018 | Dickerson |
| 2018/0085157 A1 | 3/2018 | Batchelor et al. |
| 2018/0132850 A1 | 5/2018 | Leimbach et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |
| 2018/0206904 A1 | 7/2018 | Felder et al. |
| 2018/0221045 A1 | 8/2018 | Zimmerman et al. |
| 2018/0250066 A1 | 9/2018 | Ding et al. |
| 2018/0271578 A1 | 9/2018 | Coulombe |
| 2018/0289432 A1 | 10/2018 | Kostrzewski et al. |
| 2018/0303493 A1 | 10/2018 | Chapolini |
| 2018/0325517 A1 | 11/2018 | Wingardner et al. |
| 2018/0333179 A1 | 11/2018 | Weisenburgh, II et al. |
| 2018/0353245 A1 | 12/2018 | Mccloud et al. |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0000475 A1 | 1/2019 | Shelton, IV et al. |
| 2019/0000477 A1 | 1/2019 | Shelton, IV et al. |
| 2019/0029746 A1 | 1/2019 | Dudhedia et al. |
| 2019/0038283 A1 | 2/2019 | Shelton, IV et al. |
| 2019/0053818 A1 | 2/2019 | Nelson et al. |
| 2019/0104919 A1 | 4/2019 | Shelton, IV et al. |
| 2019/0117293 A1 | 4/2019 | Kano et al. |
| 2019/0125361 A1 | 5/2019 | Shelton, IV et al. |
| 2019/0125384 A1 | 5/2019 | Scheib et al. |
| 2019/0125390 A1 | 5/2019 | Shelton, IV et al. |
| 2019/0175258 A1 | 6/2019 | Tsuruta |
| 2019/0183504 A1 | 6/2019 | Shelton, IV et al. |
| 2019/0200844 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201045 A1 | 7/2019 | Yates et al. |
| 2019/0201048 A1 | 7/2019 | Stulen et al. |
| 2019/0201104 A1 | 7/2019 | Shelton, IV et al. |
| 2019/0201594 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0209201 A1 | 7/2019 | Boudreaux et al. |
| 2019/0223941 A1 | 7/2019 | Kitamura et al. |
| 2019/0269455 A1 | 9/2019 | Mensch et al. |
| 2019/0290265 A1 | 9/2019 | Shelton, IV et al. |
| 2019/0298353 A1 | 10/2019 | Shelton, IV et al. |
| 2019/0366562 A1 | 12/2019 | Zhang et al. |
| 2019/0388091 A1 | 12/2019 | Eschbach et al. |
| 2020/0054321 A1 | 2/2020 | Harris et al. |
| 2020/0078076 A1 | 3/2020 | Henderson et al. |
| 2020/0078085 A1 | 3/2020 | Yates et al. |
| 2020/0078609 A1 | 3/2020 | Messerly et al. |
| 2020/0100825 A1 | 4/2020 | Henderson et al. |
| 2020/0113622 A1 | 4/2020 | Honegger |
| 2020/0129261 A1 | 4/2020 | Eschbach |
| 2020/0138473 A1 | 5/2020 | Shelton, IV et al. |
| 2020/0188047 A1 | 6/2020 | Itkowitz et al. |
| 2020/0222111 A1 | 7/2020 | Yates et al. |
| 2020/0222112 A1 | 7/2020 | Hancock et al. |
| 2020/0261086 A1 | 8/2020 | Zeiner et al. |
| 2020/0268430 A1 | 8/2020 | Takei et al. |
| 2020/0268433 A1 | 8/2020 | Wiener et al. |
| 2020/0305870 A1 | 10/2020 | Shelton, IV |
| 2020/0315623 A1 | 10/2020 | Eisinger et al. |
| 2020/0315712 A1 | 10/2020 | Jasperson et al. |
| 2020/0338370 A1 | 10/2020 | Wiener et al. |
| 2020/0405296 A1 | 12/2020 | Shelton, IV et al. |
| 2020/0405302 A1 | 12/2020 | Shelton, IV et al. |
| 2020/0405410 A1 | 12/2020 | Shelton, IV |
| 2020/0410177 A1 | 12/2020 | Shelton, IV |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0153927 A1 | 5/2021 | Ross et al. |
| 2021/0177481 A1 | 6/2021 | Shelton, IV et al. |
| 2021/0177494 A1 | 6/2021 | Houser et al. |
| 2021/0177496 A1 | 6/2021 | Shelton, IV et al. |
| 2021/0186492 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186499 A1 | 6/2021 | Shelton, IV et al. |
| 2021/0186501 A1 | 6/2021 | Shelton, IV et al. |
| 2021/0186553 A1 | 6/2021 | Green et al. |
| 2021/0186554 A1 | 6/2021 | Green et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196301 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196350 A1 | 7/2021 | Fiebig et al. |
| 2021/0196351 A1 | 7/2021 | Sarley et al. |
| 2021/0196352 A1 | 7/2021 | Messerly et al. |
| 2021/0196353 A1 | 7/2021 | Gee et al. |
| 2021/0196354 A1 | 7/2021 | Shelton, IV et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0212754 A1 | 7/2021 | Olson |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |

(56) References Cited

U.S. PATENT DOCUMENTS

| | | | |
|---|---|---|---|
| 2021/0393314 | A1 | 12/2021 | Wiener et al. |
| 2021/0393319 | A1 | 12/2021 | Shelton, IV et al. |
| 2022/0039891 | A1 | 2/2022 | Stulen et al. |
| 2022/0071655 | A1 | 3/2022 | Price et al. |
| 2022/0167982 | A1 | 6/2022 | Shelton, IV et al. |
| 2022/0168005 | A1 | 6/2022 | Aldridge et al. |
| 2022/0168039 | A1 | 6/2022 | Worrell et al. |
| 2022/0226014 | A1 | 7/2022 | Clauda, IV et al. |
| 2022/0304736 | A1 | 9/2022 | Boudreaux |
| 2022/0313297 | A1 | 10/2022 | Aldridge et al. |
| 2022/0346863 | A1 | 11/2022 | Yates et al. |
| 2022/0387067 | A1 | 12/2022 | Faller et al. |
| 2022/0406452 | A1 | 12/2022 | Shelton, IV |
| 2023/0038162 | A1 | 2/2023 | Timm et al. |
| 2023/0048996 | A1 | 2/2023 | Vakharia et al. |
| 2023/0270486 | A1 | 8/2023 | Wiener et al. |
| 2023/0277205 | A1 | 9/2023 | Olson et al. |
| 2023/0372743 | A1 | 11/2023 | Wiener et al. |
| 2023/0380880 | A1 | 11/2023 | Wiener et al. |

FOREIGN PATENT DOCUMENTS

| | | | |
|---|---|---|---|
| CN | 1634601 | A | 7/2005 |
| CN | 1775323 | A | 5/2006 |
| CN | 1922563 | A | 2/2007 |
| CN | 2868227 | Y | 2/2007 |
| CN | 201029899 | Y | 3/2008 |
| CN | 101474081 | A | 7/2009 |
| CN | 101516285 | A | 8/2009 |
| CN | 101522112 | A | 9/2009 |
| CN | 102100582 | A | 6/2011 |
| CN | 102149312 | A | 8/2011 |
| CN | 202027624 | U | 11/2011 |
| CN | 102792181 | A | 11/2012 |
| CN | 103281982 | A | 9/2013 |
| CN | 103379853 | A | 10/2013 |
| CN | 203468630 | U | 3/2014 |
| CN | 104001276 | A | 8/2014 |
| CN | 104013444 | A | 9/2014 |
| CN | 104434298 | A | 3/2015 |
| CN | 107374752 | A | 11/2017 |
| DE | 3904558 | A1 | 8/1990 |
| DE | 9210327 | U1 | 11/1992 |
| DE | 4300307 | A1 | 7/1994 |
| DE | 29623113 | U1 | 10/1997 |
| DE | 20004812 | U1 | 9/2000 |
| DE | 20021619 | U1 | 3/2001 |
| DE | 10042606 | A1 | 8/2001 |
| DE | 10201569 | A1 | 7/2003 |
| DE | 102012109037 | A1 | 4/2014 |
| EP | 0171967 | A2 | 2/1986 |
| EP | 0336742 | A2 | 10/1989 |
| EP | 0136855 | B1 | 11/1989 |
| EP | 0705571 | A1 | 4/1996 |
| EP | 1698289 | A2 | 9/2006 |
| EP | 1862133 | A1 | 12/2007 |
| EP | 1972264 | A1 | 9/2008 |
| EP | 2060238 | A1 | 5/2009 |
| EP | 1747761 | B1 | 10/2009 |
| EP | 2131760 | A1 | 12/2009 |
| EP | 1214913 | B1 | 7/2010 |
| EP | 1946708 | B1 | 6/2011 |
| EP | 1767164 | B1 | 1/2013 |
| EP | 2578172 | A2 | 4/2013 |
| EP | 2668922 | A1 | 12/2013 |
| EP | 2076195 | B1 | 12/2015 |
| EP | 2510891 | B1 | 6/2016 |
| EP | 3476302 | A2 | 5/2019 |
| EP | 3476331 | A1 | 5/2019 |
| EP | 3694298 | A1 | 8/2020 |
| GB | 2032221 | A | 4/1980 |
| GB | 2317566 | A | 4/1998 |
| JP | S50100891 | A | 8/1975 |
| JP | S5968513 | U | 5/1984 |
| JP | S59141938 | A | 8/1984 |
| JP | S62221343 | A | 9/1987 |
| JP | S62227343 | A | 10/1987 |
| JP | S62292153 | A | 12/1987 |
| JP | S62292154 | A | 12/1987 |
| JP | S63109386 | A | 5/1988 |
| JP | S63315049 | A | 12/1988 |
| JP | H01151452 | A | 6/1989 |
| JP | H01198540 | A | 8/1989 |
| JP | H0271510 | U | 5/1990 |
| JP | H02286149 | A | 11/1990 |
| JP | H02292193 | A | 12/1990 |
| JP | H0337061 | A | 2/1991 |
| JP | H0425707 | U | 2/1992 |
| JP | H0464351 | A | 2/1992 |
| JP | H0430508 | U | 3/1992 |
| JP | H04152942 | A | 5/1992 |
| JP | H 0541716 | A | 2/1993 |
| JP | H0576482 | A | 3/1993 |
| JP | H0595955 | A | 4/1993 |
| JP | H05115490 | A | 5/1993 |
| JP | H0670938 | A | 3/1994 |
| JP | H06104503 | A | 4/1994 |
| JP | H0824266 | A | 1/1996 |
| JP | H08229050 | A | 9/1996 |
| JP | H08275951 | A | 10/1996 |
| JP | H08299351 | A | 11/1996 |
| JP | H08336545 | A | 12/1996 |
| JP | H09130655 | A | 5/1997 |
| JP | H09135553 | A | 5/1997 |
| JP | H09140722 | A | 6/1997 |
| JP | H105237 | A | 1/1998 |
| JP | 10127654 | A | 5/1998 |
| JP | H10295700 | A | 11/1998 |
| JP | H11128238 | A | 5/1999 |
| JP | H11169381 | A | 6/1999 |
| JP | 2000210299 | A | 8/2000 |
| JP | 2000271142 | A | 10/2000 |
| JP | 2000271145 | A | 10/2000 |
| JP | 2000287987 | A | 10/2000 |
| JP | 2001029353 | A | 2/2001 |
| JP | 2002059380 | A | 2/2002 |
| JP | 2002186901 | A | 7/2002 |
| JP | 2002263579 | A | 9/2002 |
| JP | 2002330977 | A | 11/2002 |
| JP | 2003000612 | A | 1/2003 |
| JP | 2003010201 | A | 1/2003 |
| JP | 2003116870 | A | 4/2003 |
| JP | 2003126104 | A | 5/2003 |
| JP | 2003126110 | A | 5/2003 |
| JP | 2003153919 | A | 5/2003 |
| JP | 2003339730 | A | 12/2003 |
| JP | 2004129871 | A | 4/2004 |
| JP | 2004147701 | A | 5/2004 |
| JP | 2005003496 | A | 1/2005 |
| JP | 2005027026 | A | 1/2005 |
| JP | 2005074088 | A | 3/2005 |
| JP | 2005337119 | A | 12/2005 |
| JP | 2006068396 | A | 3/2006 |
| JP | 2006081664 | A | 3/2006 |
| JP | 2006114072 | A | 4/2006 |
| JP | 2006217716 | A | 8/2006 |
| JP | 2006288431 | A | 10/2006 |
| JP | 2007037568 | A | 2/2007 |
| JP | 200801876 | A | 1/2008 |
| JP | 2008017876 | A | 1/2008 |
| JP | 200833644 | A | 2/2008 |
| JP | 2008188160 | A | 8/2008 |
| JP | D1339835 | S | 8/2008 |
| JP | 2010009686 | A | 1/2010 |
| JP | 2010121865 | A | 6/2010 |
| JP | 2012071186 | A | 4/2012 |
| JP | 2012223582 | A | 11/2012 |
| JP | 2012235658 | A | 11/2012 |
| JP | 2013126430 | A | 6/2013 |
| KR | 100789356 | B1 | 12/2007 |
| KR | 101298237 | B1 | 8/2013 |
| RU | 2154437 | C1 | 8/2000 |
| RU | 22035 | U1 | 3/2002 |
| RU | 2201169 | C2 | 3/2003 |

(56) References Cited

FOREIGN PATENT DOCUMENTS

| RU | 2405603 C1 | 12/2010 |
|---|---|---|
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9712557 A1 | 4/1997 |
| WO | WO-9800069 A1 | 1/1998 |
| WO | WO-9840015 A2 | 9/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-02080793 A1 | 10/2002 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2006091494 A1 | 8/2006 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |
| WO | WO-2011060031 A1 | 5/2011 |
| WO | WO-2011092464 A1 | 8/2011 |
| WO | WO-2012044606 A2 | 4/2012 |
| WO | WO-2012061722 A2 | 5/2012 |
| WO | WO-2012088535 A1 | 6/2012 |
| WO | WO-2012150567 A1 | 11/2012 |
| WO | WO-2016130844 A1 | 8/2016 |
| WO | WO-2019130090 A1 | 7/2019 |
| WO | WO-2019130113 A1 | 7/2019 |

OTHER PUBLICATIONS

Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
Jang, J. et al. "Neuro-fuzzy and Soft Computing." Prentice Hall, 1997, pp. 13-89, 199-293, 335-393, 453-496, 535-549.
Sullivan, "Optimal Choice for Number of Strands in a Litz-Wire Transformer Winding," IEEE Transactions on Power Electronics, vol. 14, No. 2, Mar. 1999, pp. 283-291.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wall et al., "Thermal modification of collagen," J Shoulder Elbow Surg, No. 8, pp. 339-344 (Jul./Aug. 1999).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Douglas, S.C. "Introduction to Adaptive Filter". Digital Signal Processing Handbook. Ed. Vijay K. Madisetti and Douglas B. Williams. Boca Raton: CRC Press LLC, 1999.
Chen et al., "Heat-induced changes in the mechanics of a collagenous tissue: pseudoelastic behavior at 37° C," Journal of Biomechanics, 31, pp. 211-216 (1998).
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Walsh, S. J., White, R. G., "Vibrational Power Transmission in Curved Beams," Journal of Sound and Vibration, 233(3), 455-488 (2000).
Covidien 501(k) Summary Sonicision, dated Feb. 24, 2011 (7 pages).
Morley, L. S. D., "Elastic Waves in a Naturally Curved Rod," Quarterly Journal of Mechanics and Applied Mathematics, 14: 155-172 (1961).

(56) References Cited

OTHER PUBLICATIONS

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C .; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Campbell et al, "Thermal Imaging in Surgery," p. 19-3, in Medical Infrared Imaging, N. A. Diakides and J. D. Bronzino, Eds. (2008).
Gerhard, Glen C., "Surgical Electrotechnology: Quo Vadis?," IEEE Transactions on Biomedical Engineering, vol. BME-31, No. 12, pp. 787-792, Dec. 1984.
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Kurt Gieck & Reiner Gieck, *Engineering Formulas* § Z.7 (7th ed. 1997).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Leonard I. Malis, M.D., "The Value of Irrigation During Bipolar Coagulation," 1989.
Covidien Brochure, The LigaSure Precise™ Instrument, dated Mar. 2011 (2 pages).
Glaser and Subak-Sharpe,Integrated Circuit Engineering, Addison-Wesley Publishing, Reading, MA (1979). (book—not attached).
Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Moraleda et al., A Temperature Sensor Based on a Polymer Optical Fiber Macro-Bend, Sensors 2013, 13, 13076-13089, doi: 10.3390/s131013076, ISSN 1424-8220.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Missinne, et al. "Stretchable Optical Waveguides," vol. 22, No. 4, Feb. 18, 2014, pp. 4168-4179 (12 pages).

\* cited by examiner

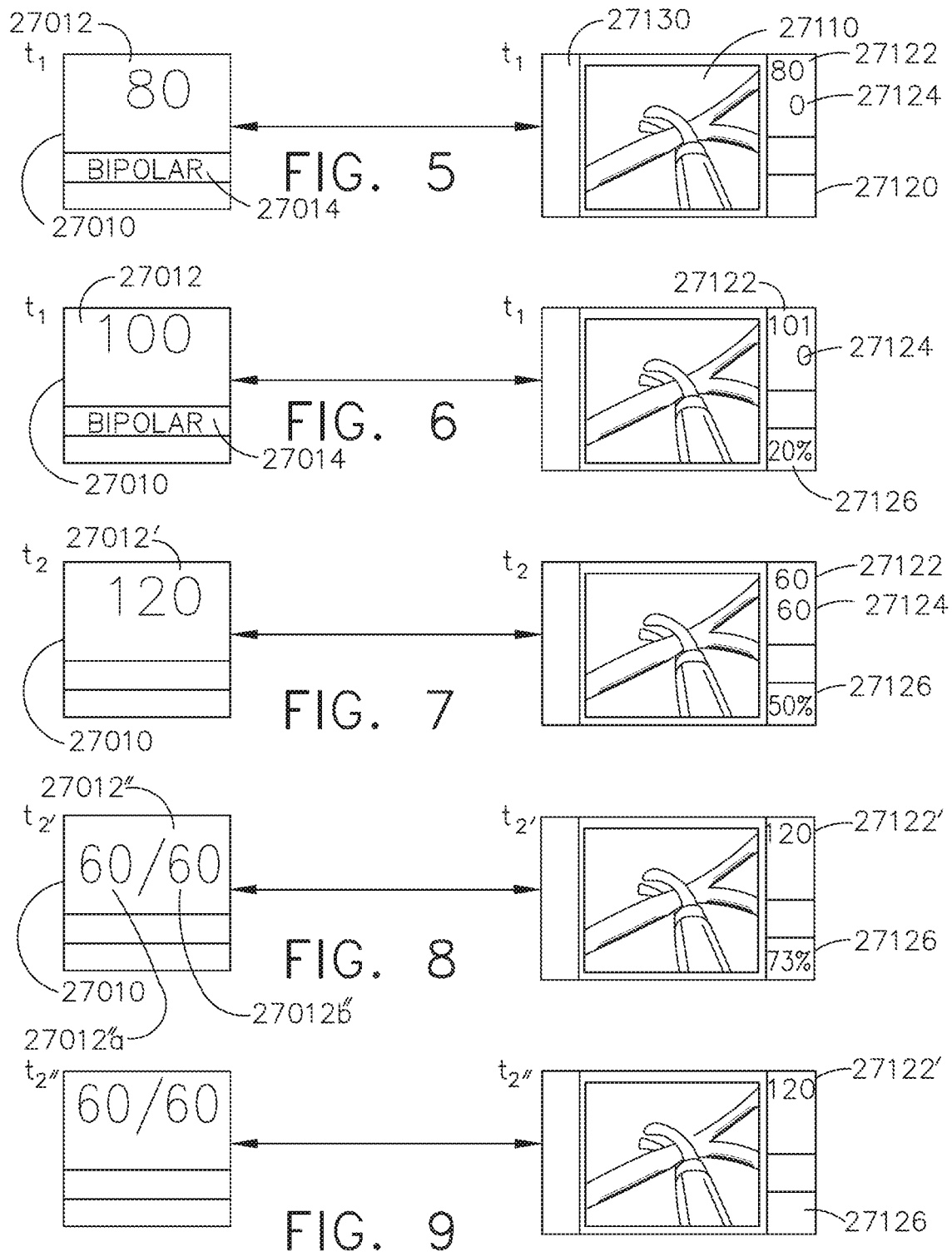

| Time | Tissue Operation | Energy type | Jaw aperture | Image |
|---|---|---|---|---|
| $t_0$ | No tissue contact | n/a | 0.700"–0.500" | |
| $t_1$ | Feathering | Bipolar | 0.500"–0.030" | |
| $t_2$ | Tissue Warming power | Bipolar & Monopolar | 0.030"–0.010" | |
| $t_3$ | Sealing | Monopolar & Bipolar | 0.010"–0.003" | |
| $t_4$ | Cutting | Monopolar | 0.010"–0.003" | |

FIG. 16

SURGICAL SYSTEM COMMUNICATION PATHWAYS

CROSS REFERENCE TO RELATED APPLICATIONS

This non-provisional application claims the benefit under 35 U.S.C. § 119(e) of U.S. Provisional Patent Application Ser. No. 62/955,299, entitled DEVICES AND SYSTEMS FOR ELECTROSURGERY, filed Dec. 30, 2019, the disclosure of which is incorporated by reference herein in its entirety.

BACKGROUND

The present invention relates to surgical instruments designed to treat tissue, including but not limited to surgical instruments that are configured to cut and fasten tissue. The surgical instruments may include electrosurgical instruments powered by generators to effect tissue dissecting, cutting, and/or coagulation during surgical procedures. The surgical instruments may include instruments that are configured to cut and staple tissue using surgical staples and/or fasteners. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

SUMMARY

In various embodiments, a surgical system comprising a surgical hub, a surgical instrument, a generator configured to energize an end effector, and a smoke evacuation system configured to remove smoke from a surgical site is disclosed. The surgical instrument comprises the end effector. A control command is passed directly from the surgical hub to the surgical instrument. The surgical instrument is configured to pass the control command received from the surgical hub to the generator and the smoke evacuation system in a daisy-chain manner.

In various embodiments, a surgical system comprising a surgical hub, a surgical instrument, a generator configured to energize an end effector, and a smoke evacuation system configured to remove smoke from a surgical site is disclosed. The surgical instrument comprises the end effector. A control command is passed directly from the surgical hub to the surgical instrument. The surgical instrument is configured to pass the control command received from the surgical hub to the generator and the smoke evacuation system.

In various embodiments, a surgical system comprising a surgical hub, a first surgical instrument, a first generator configured to energize a first end effector, and a second surgical instrument is disclosed. The first surgical instrument comprises the first end effector. A control command is passed directly from the surgical hub to the first surgical instrument. The first surgical instrument is configured to pass the control command received from the surgical hub to the first generator and the second surgical instrument in a daisy-chain manner.

FIGURE DESCRIPTIONS

The novel features of the various aspects are set forth with particularity in the appended claims. The described aspects, however, both as to organization and methods of operation, may be best understood by reference to the following description, taken in conjunction with the accompanying drawings in which:

FIG. 5 is a schematic representation of the corresponding views of the display screen of the surgical instrument and the display monitor of FIG. 4 in accordance with at least one embodiment;

FIG. 6 is a schematic representation of the corresponding views of the display screen of the surgical instrument and the display monitor of FIG. 4 in accordance with at least one embodiment;

FIG. 7 is a schematic representation of the corresponding views of the display screen of the surgical instrument and the display monitor of FIG. 4 in accordance with at least one embodiment;

FIG. 8 is a schematic representation of the corresponding views of the display screen of the surgical instrument and the display monitor of FIG. 4 in accordance with at least one embodiment;

FIG. 9 is a schematic representation of the corresponding views of the display screen of the surgical instrument and the display monitor of FIG. 4 in accordance with at least one embodiment;

Figure 13:
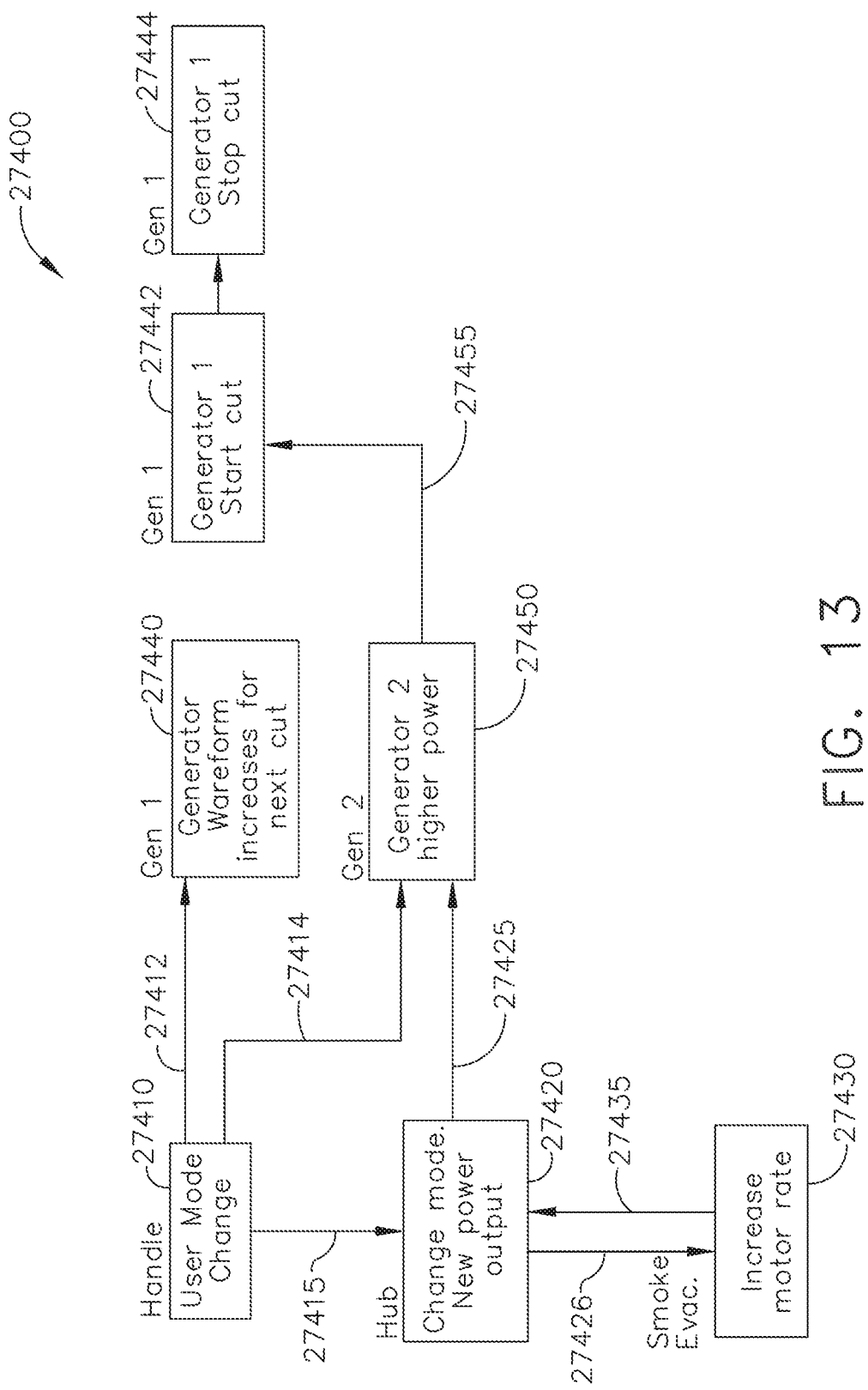
Figure 14:
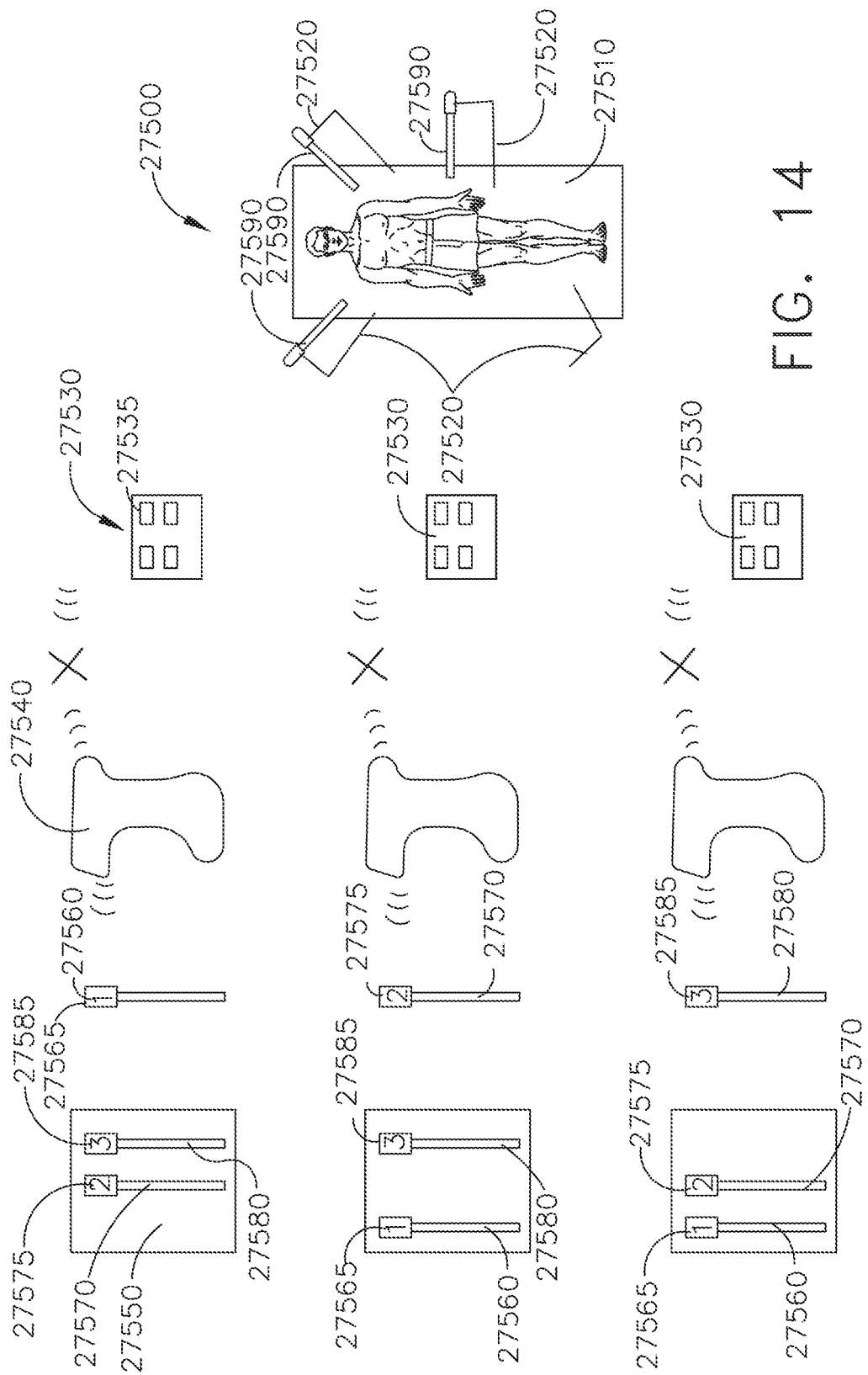
Figure 15:
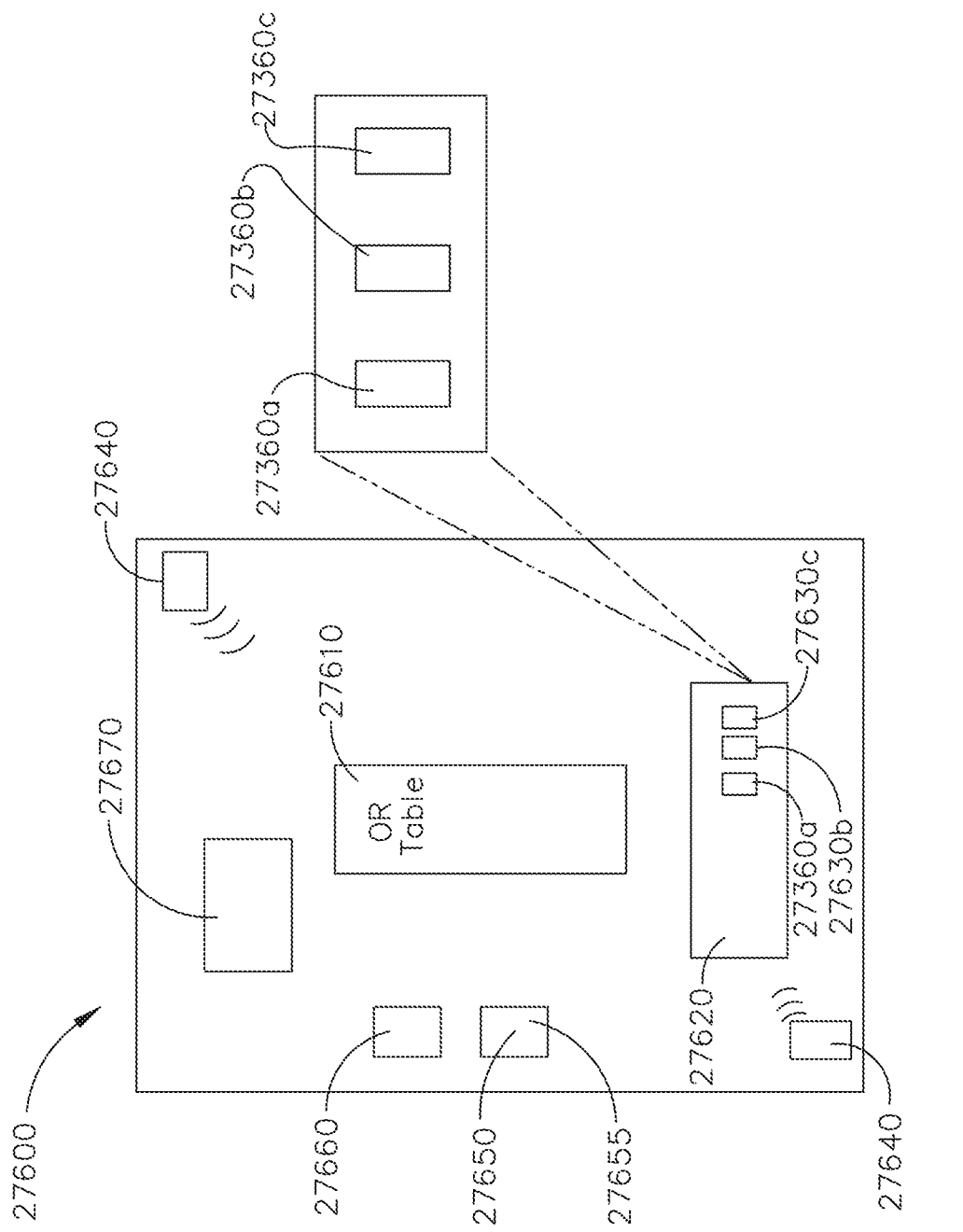
Figure 17:
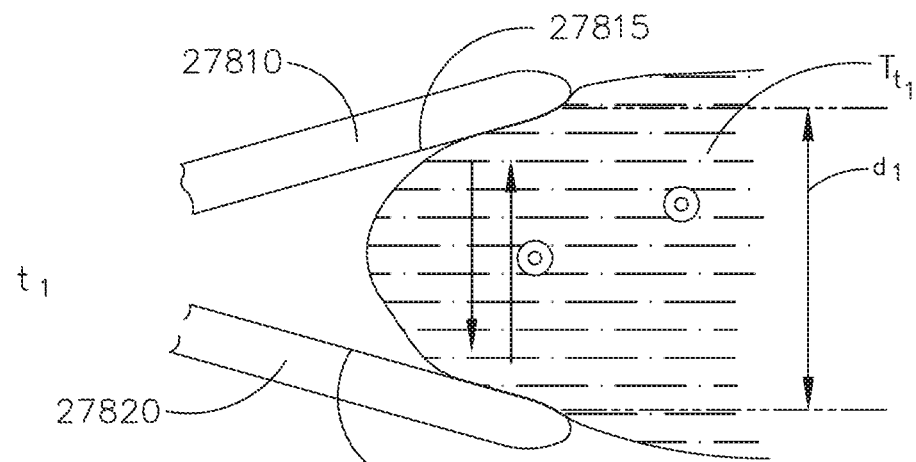
Figure 18:
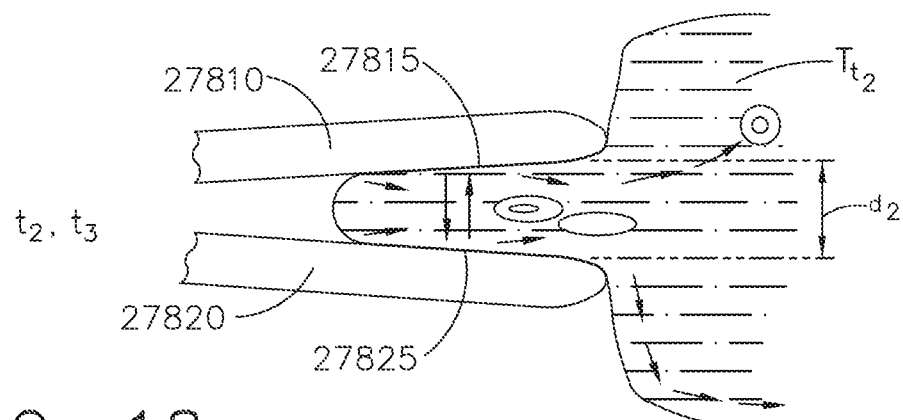
Figure 19:
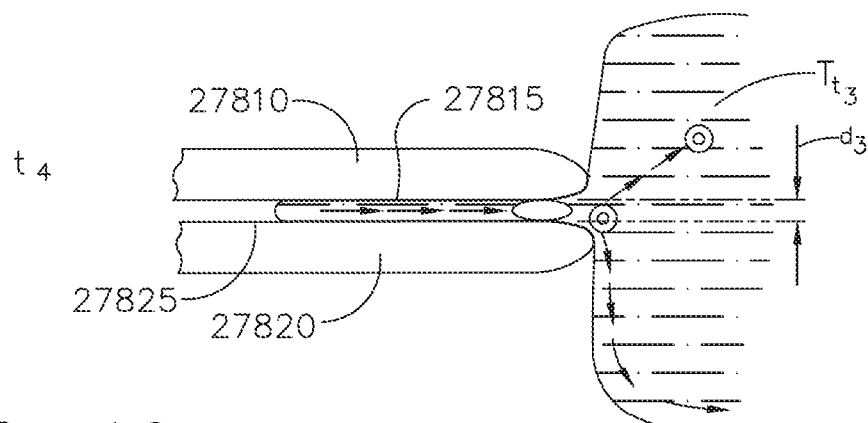
Figure 20:
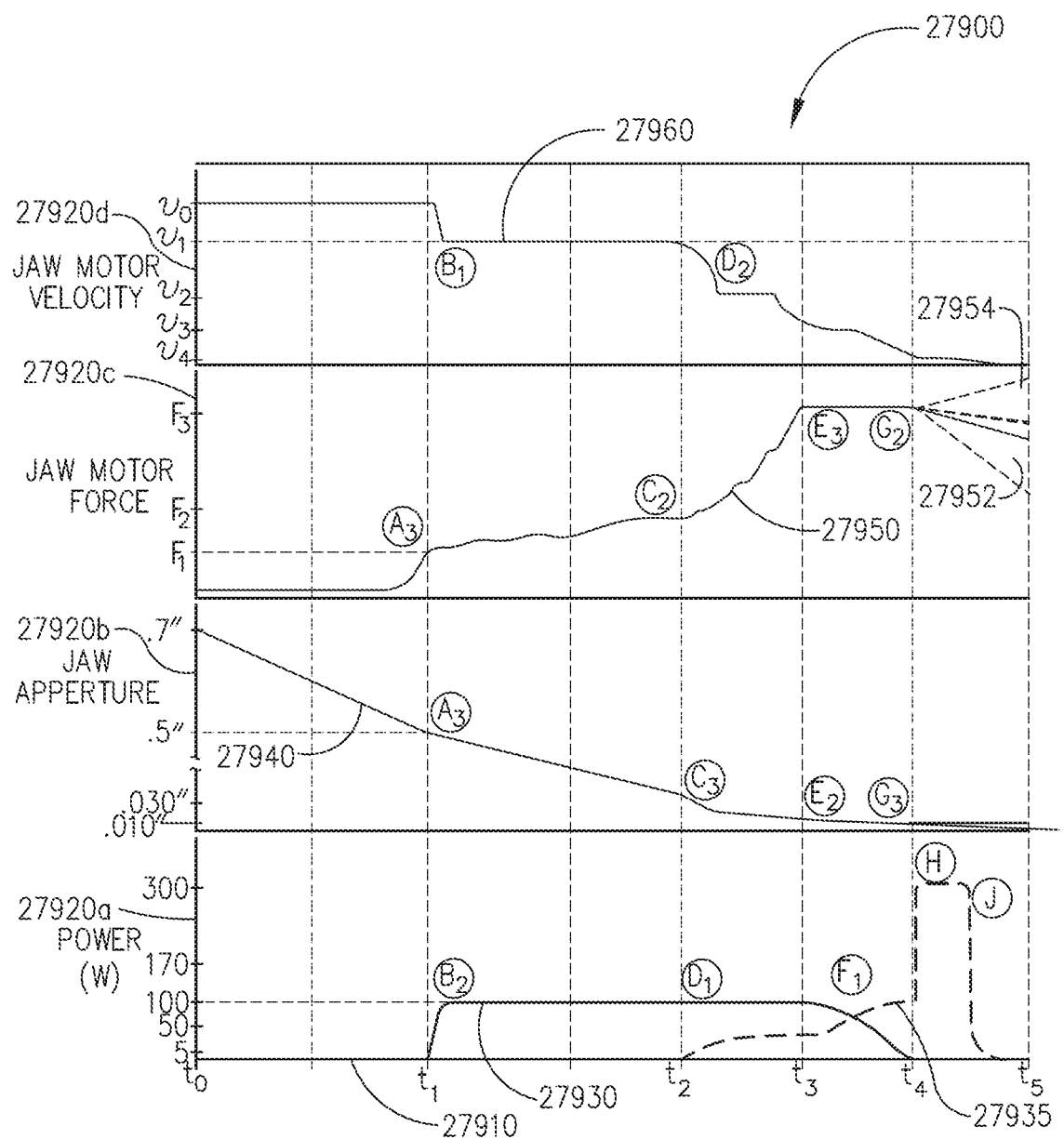
Figure 22:
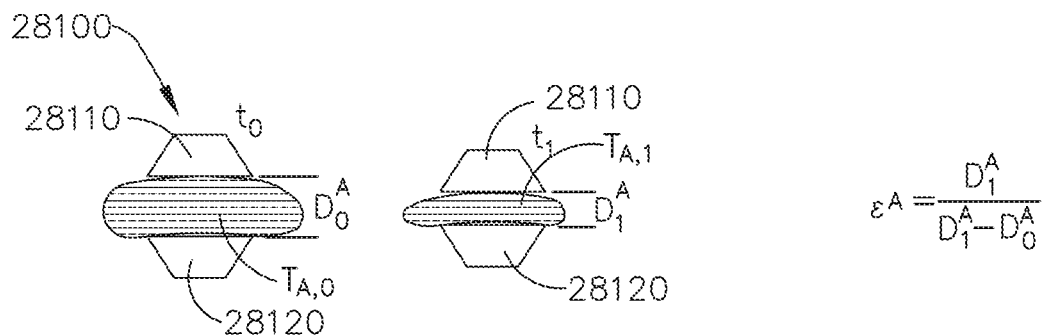
Figure 23:
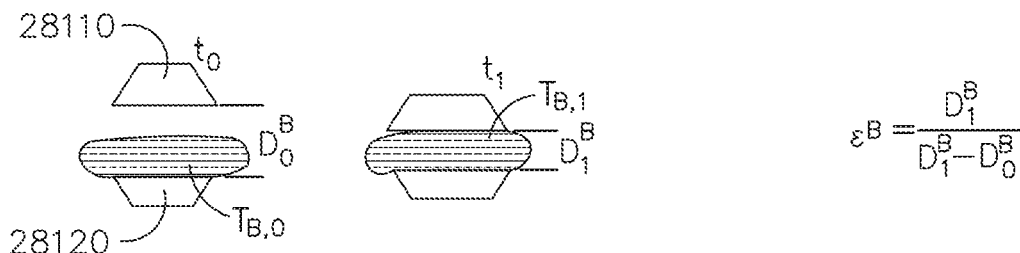
Figure 24:
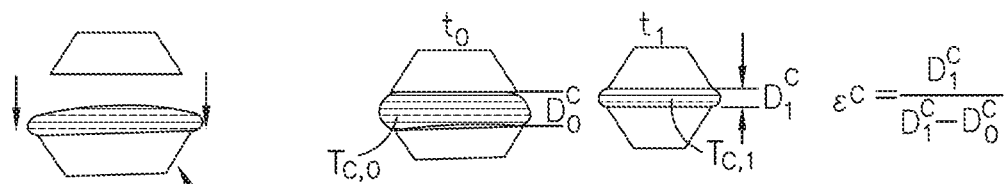
Figure 21:
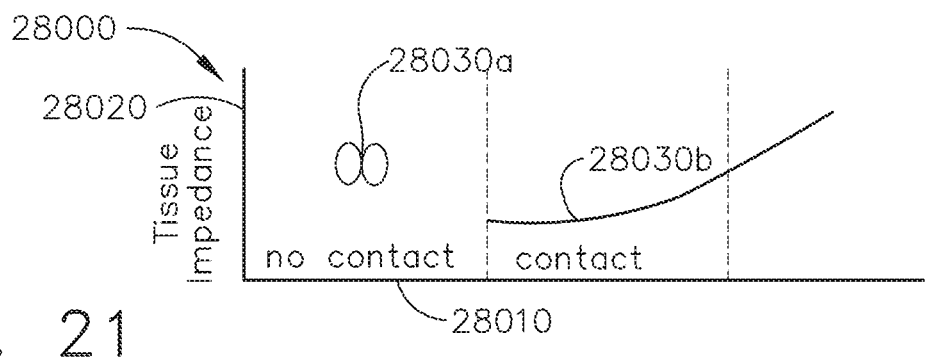
Figure 25:
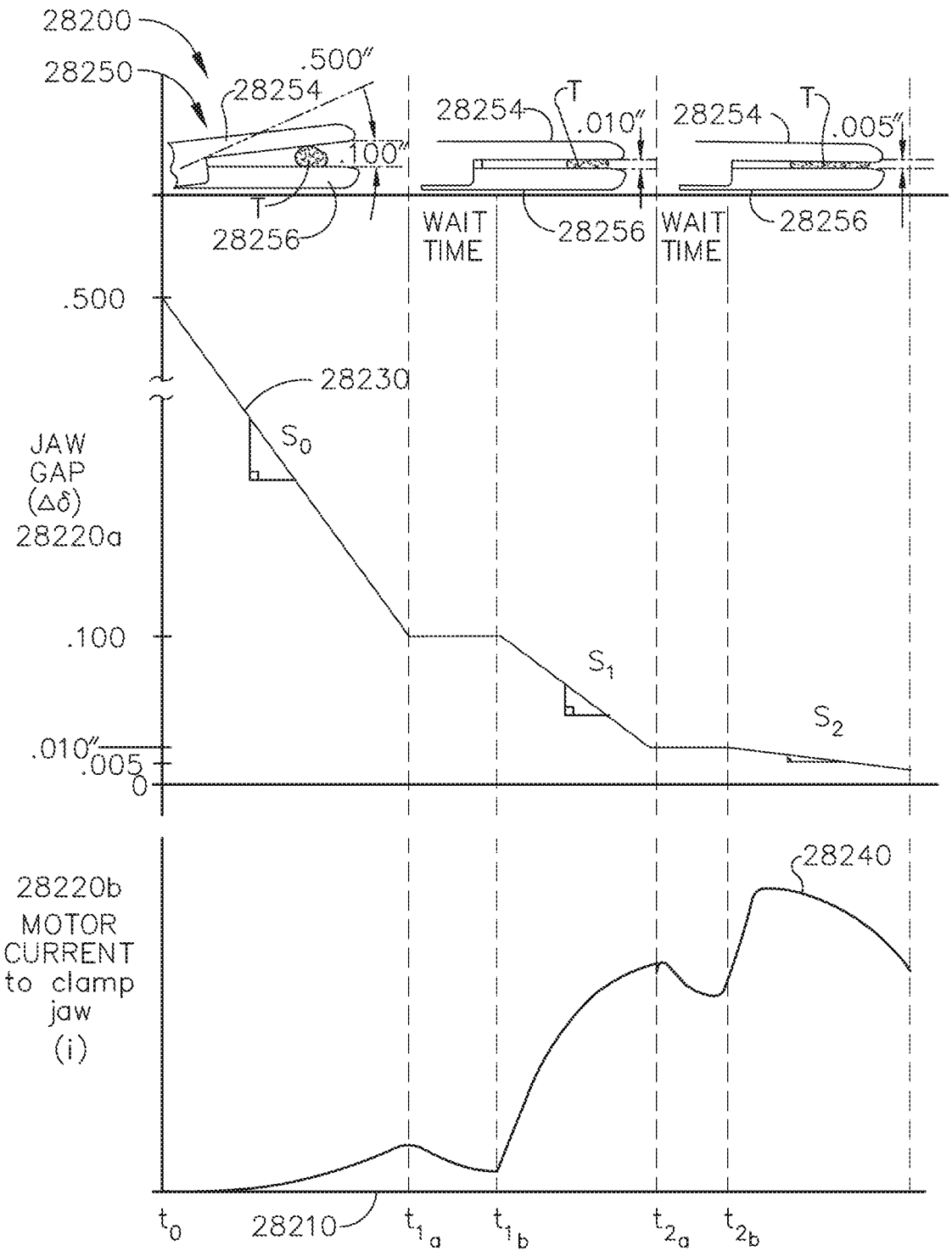
Figure 26:
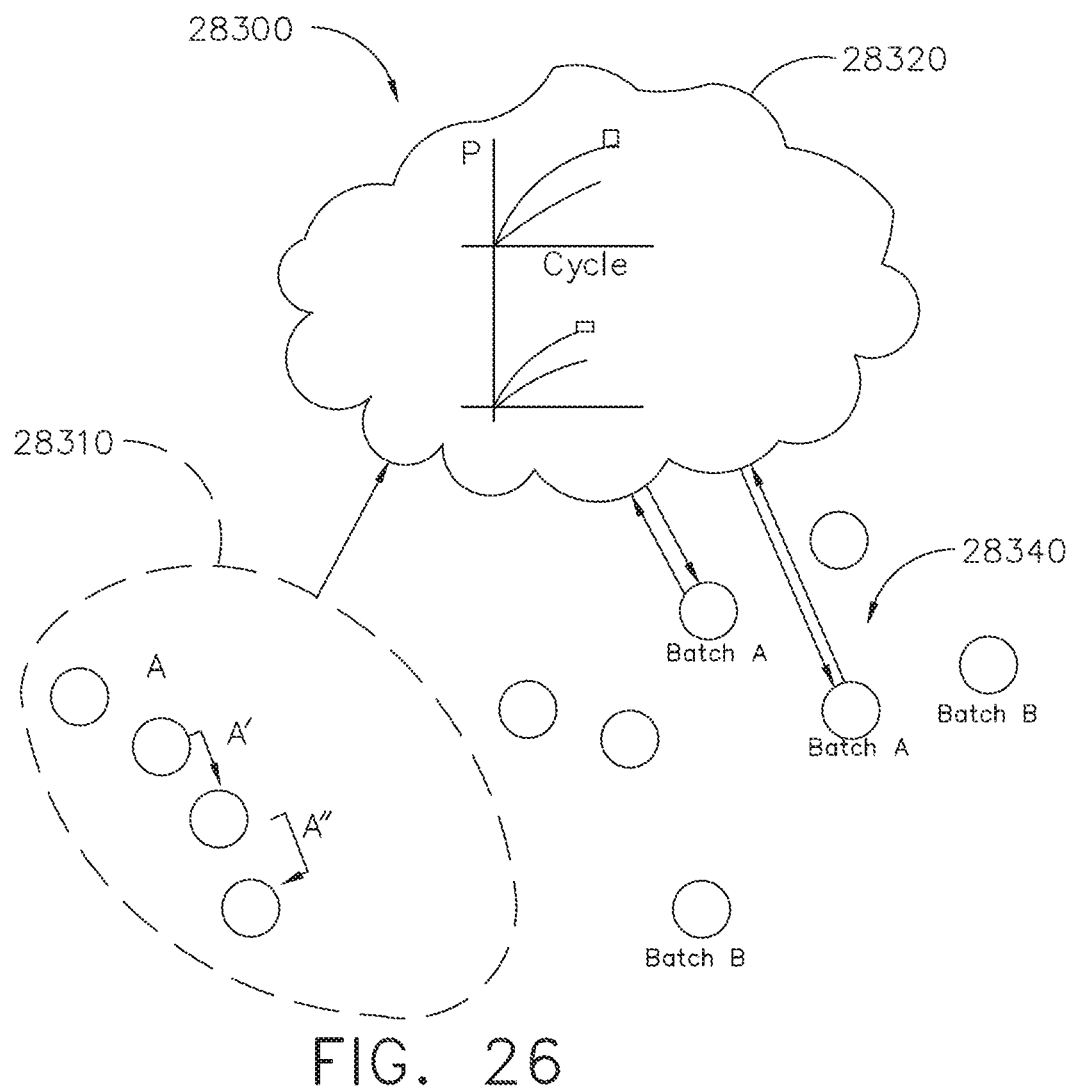
Figure 27:
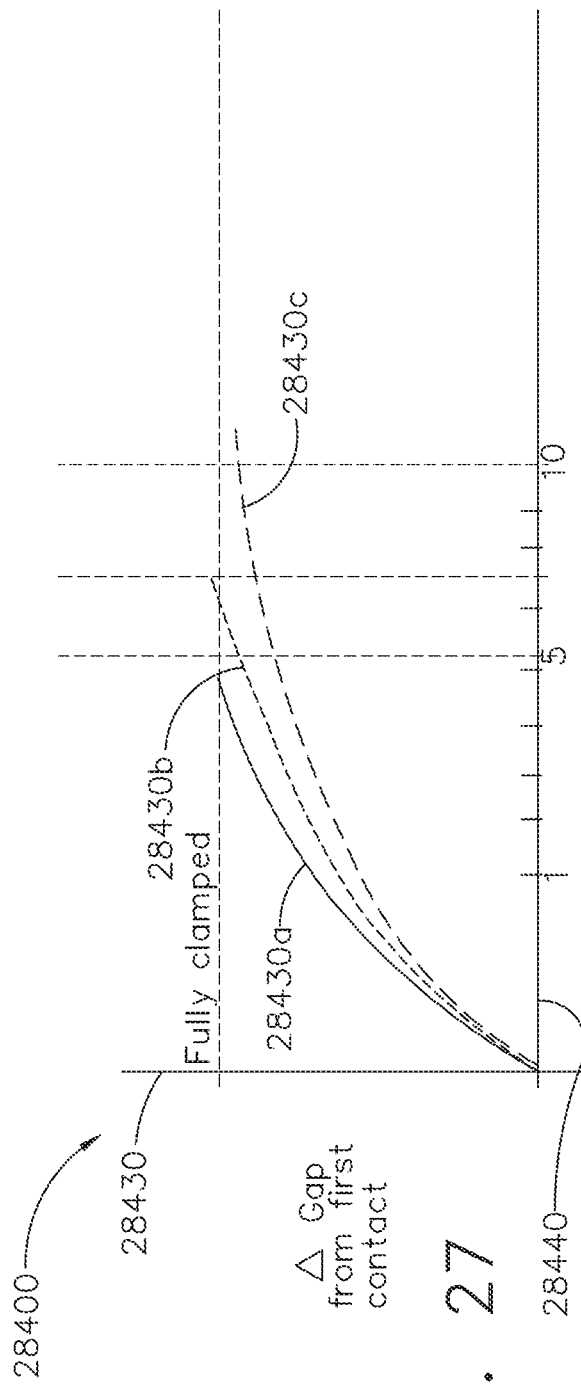
Figure 28:
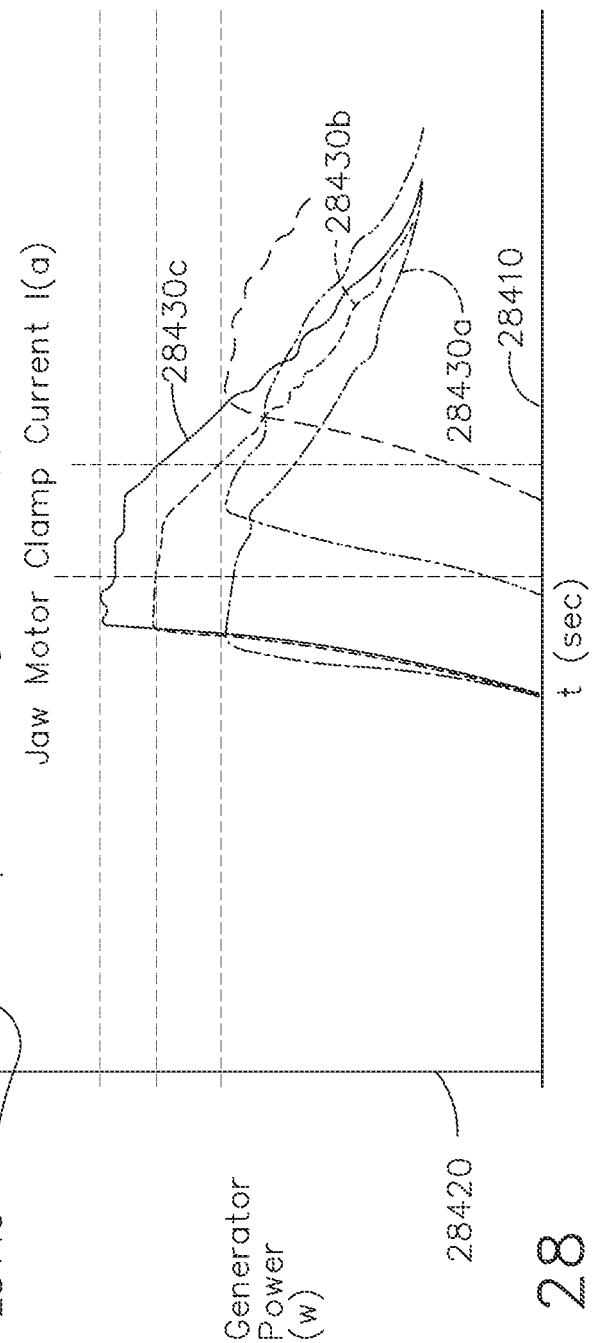
Figure 29:
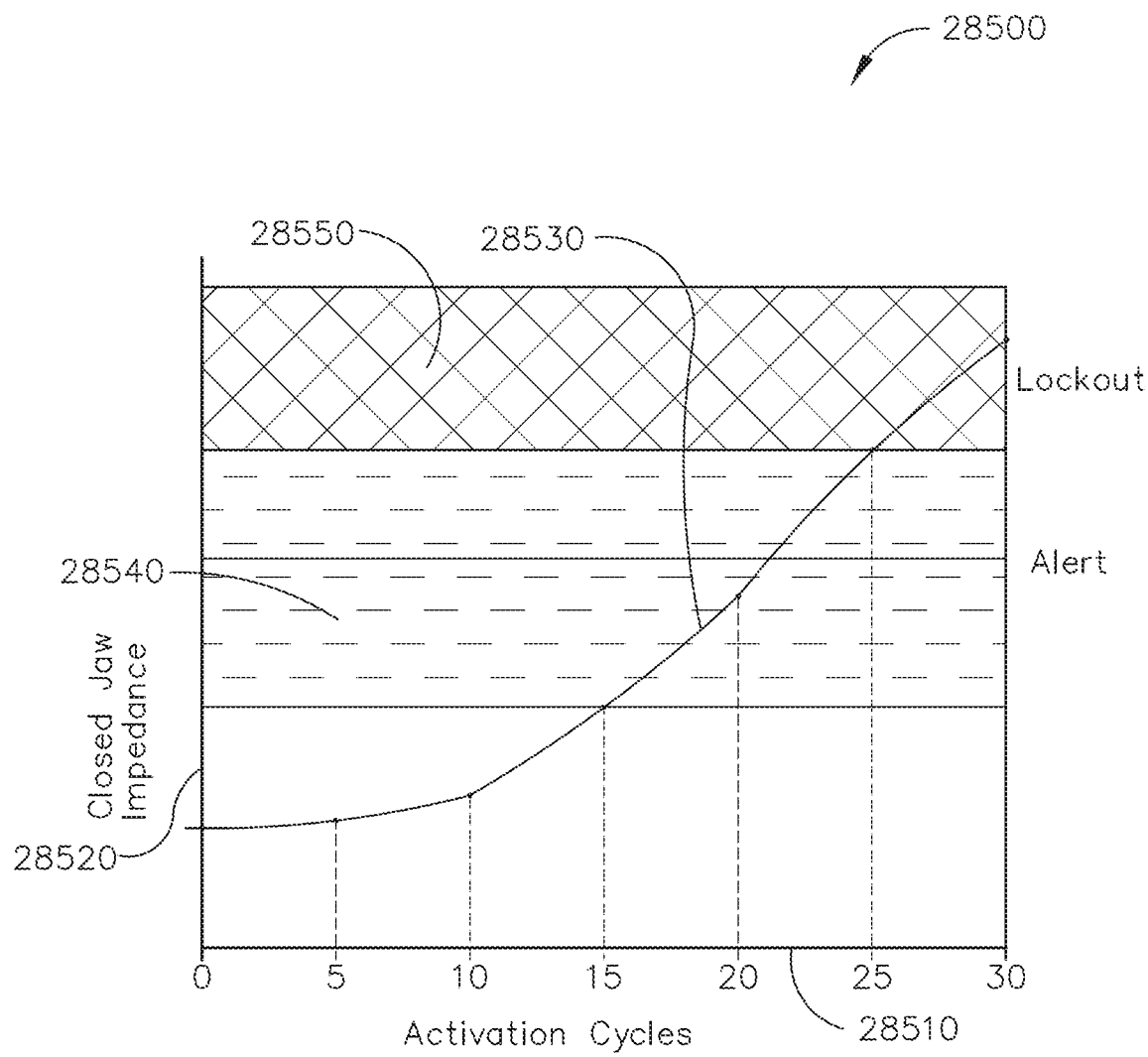
Figure 30:
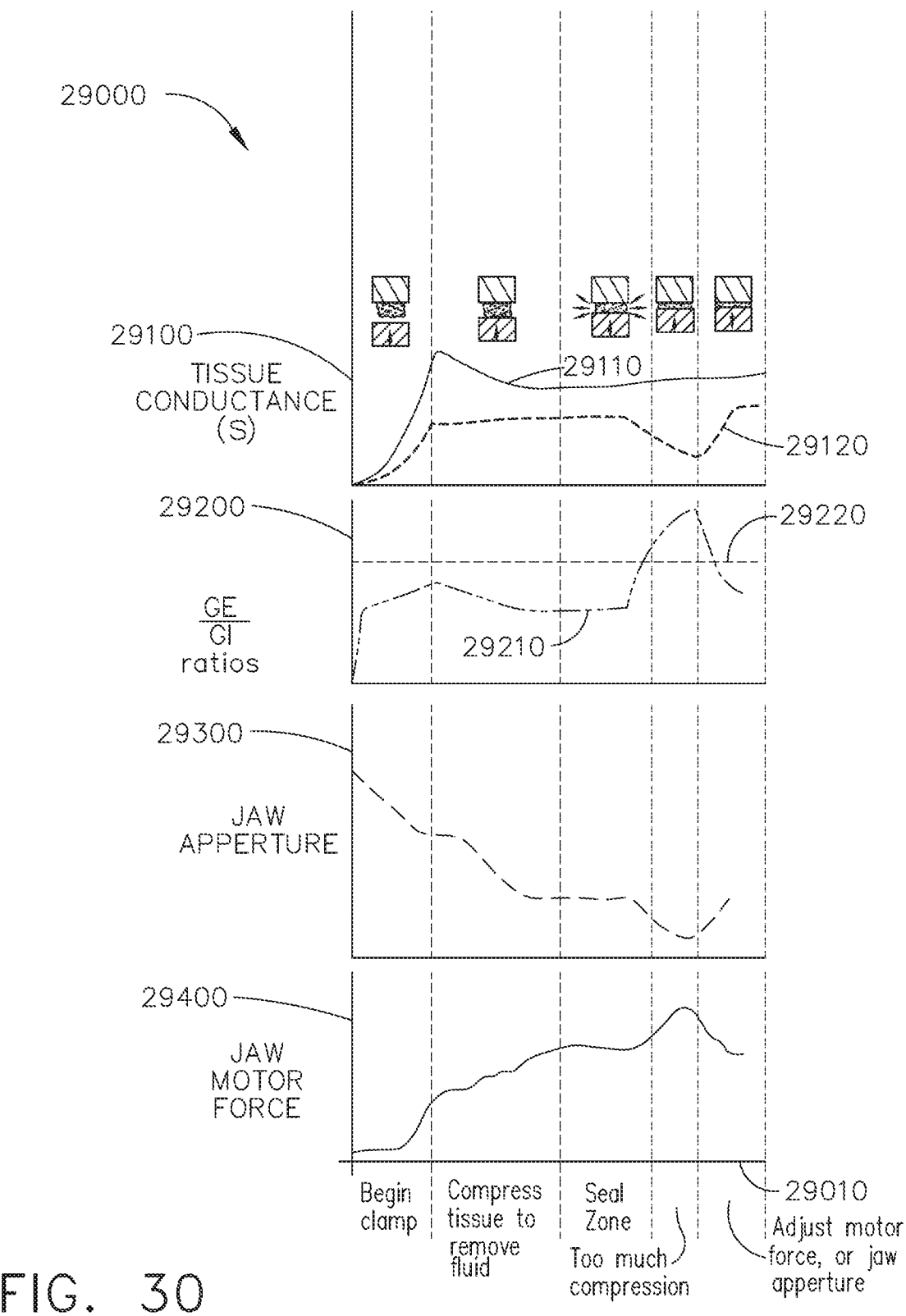
Figure 31:
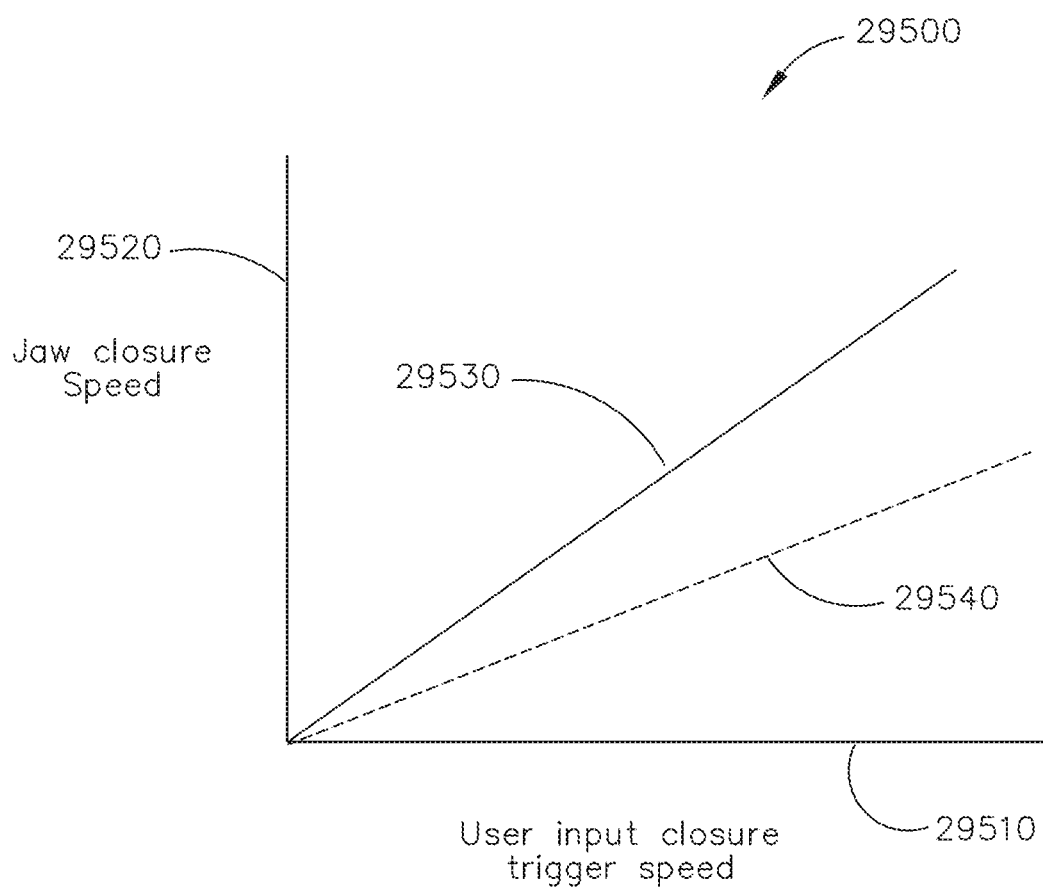

FIG. 13 is a schematic representation of the communication pathways with a surgical system, wherein the surgical system comprises a surgical hub, a smoke evacuation device, a surgical instrument, a first generator configured to power a first operation of the surgical instrument, and a second generator configured to power a second operation of the surgical instrument in accordance with at least one embodiment;

FIG. 14 is a schematic representation of a surgical system comprising a surgical hub and a plurality of robotic arms configured to receive tools thereon, wherein the surgical system comprises an authentication module configured to approve the tools for attachment to and/or use with the surgical system in accordance with at least one embodiment;

FIG. 15 is a schematic representation of a surgical system positioned within a treatment room in accordance with at least one embodiment;

FIG. 16 is a chart depicting various operational parameters and/or specifications of a surgical instrument at various stages of a surgical procedure in accordance with at least one embodiment;

FIG. 17 is an elevational view of the surgical instrument of FIG. 16 shown at a first time delivering bipolar energy to patient tissue;

FIG. 18 is an elevational view of the surgical instrument of FIG. 16 shown at a second time delivering bipolar and monopolar energies to patient tissue;

FIG. 19 is an elevational view of the surgical instrument of FIG. 16 shown at a fourth time delivering monopolar energy to patient tissue;

FIG. 20 is a graphical representation of various operational parameters and/or specifications of the surgical instrument of FIG. 16 at various stages of the surgical procedure;

FIG. 21 is a graphical representation of measured tissue impedance over a duration of a surgical procedure in accordance with at least one embodiment;

FIG. 22 is a schematic representing a strain calculation, wherein the applied strain is calculated using a gap defined between jaws of an end effector when the end effector is in an open configuration in accordance with at least one embodiment;

FIG. 23 is a schematic representing the strain calculation of FIG. 22, wherein the calculated applied strain overestimates an actual applied strain as the patient tissue is not in contact with positioned between the jaws of the end effector;

FIG. 24 is a schematic representing a tissue impedance calculation, wherein the tissue impedance is calculated using a gap defined between the jaws of the end effector when the jaws of the end effector contact the patient tissue positioned therebetween in accordance with at least one embodiment;

FIG. 25 is a graphical representation of a relationship between motor current and jaw gap over time in accordance with at least one embodiment;

FIG. 26 is a schematic representation of a network formed by surgical instruments and a cloud-based storage medium in accordance with at least one embodiment;

FIG. 27 is a graphical representation of a relationship between a change in jaw gap and jaw motor clamp current determined from the network of FIG. 26;

FIG. 28 is a graphical representation of a relationship between generator power over time determined from the network of FIG. 26;

FIG. 29 is a graphical representation of a relationship between activation cycles of a surgical instrument and a measured impedance when an end effector of the surgical instrument is in a closed configuration without patient tissue positioned therebetween in accordance with at least one embodiment;

FIG. 30 is a graphical representation of the relationships between tissue conductance, jaw aperture dimension, and jaw motor force during a jaw clamp stroke in accordance with at least one embodiment; and FIG. 31 is a graphical representation of a jaw closure speed based on a user input and the jaw closure speed based on the user input and a monitored parameter in accordance with at least one embodiment.

DESCRIPTION

Applicant of the present application owns the following U.S. Patent Applications that were filed on May 28, 2020 and which are each herein incorporated by reference in their respective entireties:

U.S. patent application Ser. No. 16/885,813, entitled METHOD FOR AN ELECTROSURGICAL PROCEDURE, now U.S. Patent Application Serial No. 2021/0196354;

U.S. patent application Ser. No. 16/885,820, entitled ARTICULATABLE SURGICAL INSTRUMENT, now U.S. Pat. No. 11,696,776;

U.S. patent application Ser. No. 16/885,823, entitled SURGICAL INSTRUMENT WITH JAW ALIGNMENT FEATURES, now U.S. Pat. No. 11,707,318;

U.S. patent application Ser. No. 16/885,826, entitled SURGICAL INSTRUMENT WITH ROTATABLE AND ARTICULATABLE SURGICAL END EFFECTOR, now U.S. Pat. No. 11,684,412;

U.S. patent application Ser. No. 16/885,838, entitled ELECTROSURGICAL INSTRUMENT WITH ASYNCHRONOUS ENERGIZING ELECTRODES, now U.S. Patent Application Serial No. 2021/0196357;

U.S. patent application Ser. No. 16/885,851, entitled ELECTROSURGICAL INSTRUMENT WITH ELECTRODES BIASING SUPPORT, now U.S. Patent Application Serial No. 2021/0196358;

U.S. patent application Ser. No. 16/885,860, entitled ELECTROSURGICAL INSTRUMENT WITH FLEXIBLE WIRING ASSEMBLIES, now U.S. Patent Application Serial No. 2021/0196349;

U.S. patent application Ser. No. 16/885,866, entitled ELECTROSURGICAL INSTRUMENT WITH VARIABLE CONTROL MECHANISMS, now U.S. Pat. No. 11,723,716;

U.S. patent application Ser. No. 16/885,870, entitled ELECTROSURGICAL SYSTEMS WITH INTEGRATED AND EXTERNAL POWER SOURCES, now U.S. Pat. No. 11,744,636;

U.S. patent application Ser. No. 16/885,873, entitled ELECTROSURGICAL INSTRUMENTS WITH ELECTRODES HAVING ENERGY FOCUSING FEATURES, now U.S. Patent Application Serial No. 2021/0196359;

U.S. patent application Ser. No. 16/885,879, entitled ELECTROSURGICAL INSTRUMENTS WITH ELECTRODES HAVING VARIABLE ENERGY DENSITIES, now U.S. Pat. No. 11,589,916;

U.S. patent application Ser. No. 16/885,881, entitled ELECTROSURGICAL INSTRUMENT WITH MONOPOLAR AND BIPOLAR ENERGY CAPABILITIES, now U.S. Patent Application Serial No. 2021/0196361;

U.S. patent application Ser. No. 16/885,888, entitled ELECTROSURGICAL END EFFECTORS WITH THERMALLY INSULATIVE AND THERMALLY CONDUCTIVE PORTIONS, now U.S. Patent Application Serial No. 2021/0196362;

U.S. patent application Ser. No. 16/885,893, entitled ELECTROSURGICAL INSTRUMENT WITH ELECTRODES OPERABLE IN BIPOLAR AND MONOPOLAR MODES, now U.S. Patent Application Serial No. 2021/0196363;

U.S. patent application Ser. No. 16/885,900, entitled ELECTROSURGICAL INSTRUMENT FOR DELIVERING BLENDED ENERGY MODALITIES TO TISSUE, now U.S. Patent Application Serial No. 2021/0196364;

U.S. patent application Ser. No. 16/885,917, entitled CONTROL PROGRAM ADAPTATION BASED ON DEVICE STATUS AND USER INPUT, now U.S. Pat. No. 11,759,251; and U.S. patent application Ser. No. 16/885,923, entitled CONTROL PROGRAM FOR MODULAR COMBINATION ENERGY DEVICE, now U.S. Pat. No. 11,786,294.

Applicant of the present application owns the following U.S. Provisional Patent Applications that were filed on Dec. 30, 2019, the disclosure of each of which is herein incorporated by reference in its entirety:

U.S. Provisional Patent Application Ser. No. 62/955,294, entitled USER INTERFACE FOR SURGICAL INSTRUMENT WITH COMBINATION ENERGY MODALITY END-EFFECTOR;

U.S. Provisional Patent Application Ser. No. 62/955,292, entitled COMBINATION ENERGY MODALITY END-EFFECTOR; and U.S. Provisional Patent Application Ser. No. 62/955,306, entitled SURGICAL INSTRUMENT SYSTEMS.

Applicant of the present application owns the following U.S. Patent Applications, the disclosure of each of which is herein incorporated by reference in its entirety:

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Patent Application Publication No. 2019/0201137;

U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;

U.S. patent application Ser. No. 16/209,490, titled METHOD FOR FACILITY DATA COLLECTION AND INTERPRETATION, now U.S. Patent Application Publication No. 2019/0206564;

U.S. patent application Ser. No. 16/209,491, titled METHOD FOR CIRCULAR STAPLER CONTROL ALGORITHM ADJUSTMENT BASED ON SITUATIONAL AWARENESS, now U.S. Patent Application Publication No. 2019/0200998;

U.S. patent application Ser. No. 16/562,123, titled METHOD FOR CONSTRUCTING AND USING A MODULAR SURGICAL ENERGY SYSTEM WITH MULTIPLE DEVICES;

U.S. patent application Ser. No. 16/562,135, titled METHOD FOR CONTROLLING AN ENERGY MODULE OUTPUT;

U.S. patent application Ser. No. 16/562,144, titled METHOD FOR CONTROLLING A MODULAR ENERGY SYSTEM USER INTERFACE; and U.S. patent application Ser. No. 16/562,125, titled METHOD FOR COMMUNICATING BETWEEN MODULES AND DEVICES IN A MODULAR SURGICAL SYSTEM.

Before explaining various aspects of an electrosurgical system in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Various aspects are directed to electrosurgical systems that include electrosurgical instruments powered by generators to effect tissue dissecting, cutting, and/or coagulation during surgical procedures. The electrosurgical instruments may be configured for use in open surgical procedures, but has applications in other types of surgery, such as laparoscopic, endoscopic, and robotic-assisted procedures.

As described below in greater detail, an electrosurgical instrument generally includes a shaft having a distally-mounted end effector (e.g., one or more electrodes). The end effector can be positioned against the tissue such that electrical current is introduced into the tissue. Electrosurgical instruments can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example.

Figure 1:
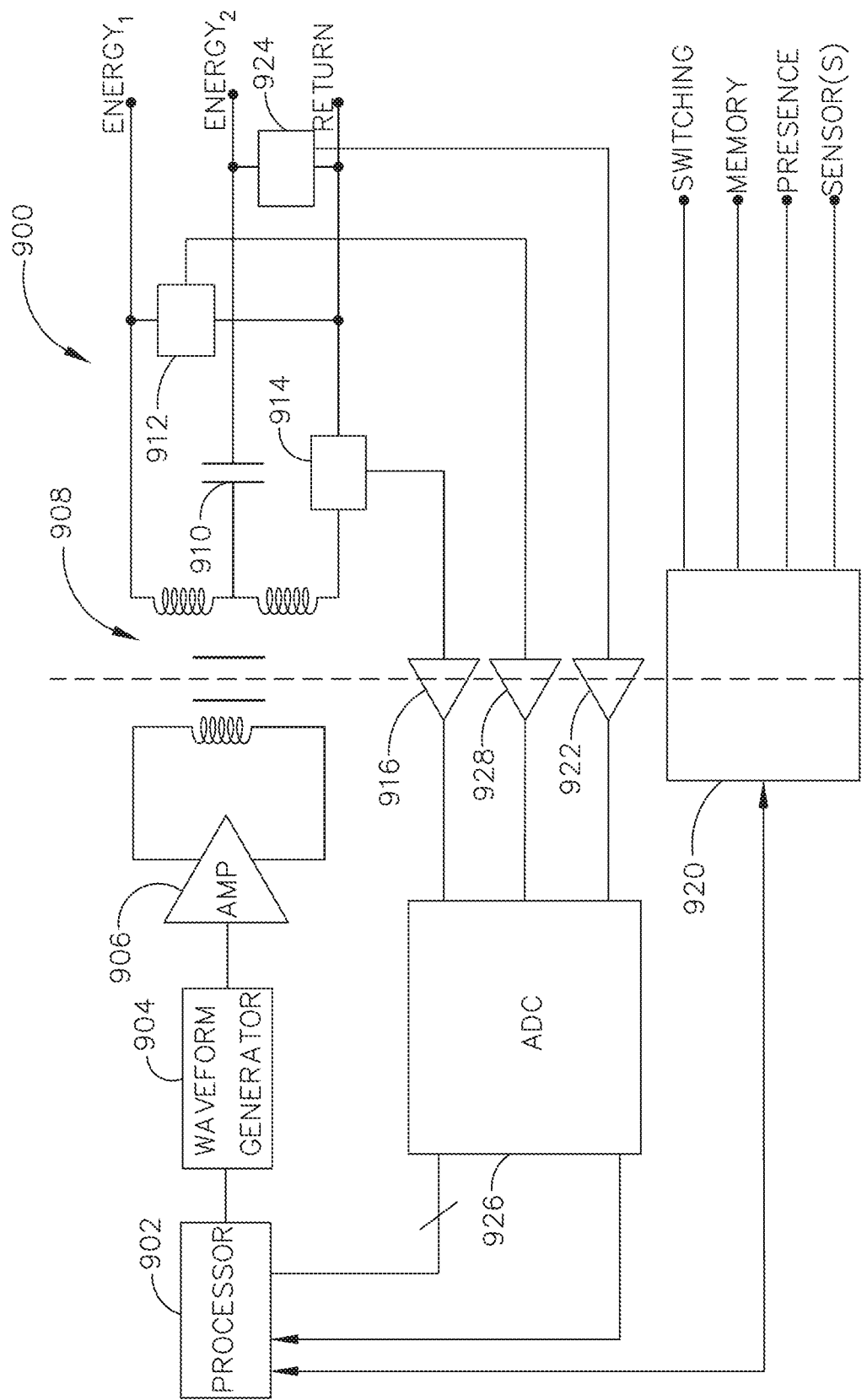
FIG. 1 illustrates an example of a generator for use with a surgical system, in accordance with at least one aspect of the present disclosure.

FIG. 1 illustrates an example of a generator 900 configured to deliver multiple energy modalities to a surgical instrument. The generator 900 provides RF and/or ultrasonic signals for delivering energy to a surgical instrument. The generator 900 comprises at least one generator output that can deliver multiple energy modalities (e.g., ultrasonic, bipolar or monopolar RF, irreversible and/or reversible electroporation, and/or microwave energy, among others) through a single port, and these signals can be delivered separately or simultaneously to an end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 906 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled $ENERGY_1$ and RETURN. A second signal of a second energy modality is coupled across a capacitor 910 and is provided to the surgical instrument between the terminals labeled $ENERGY_2$ and RETURN. It will be appreciated that more than two energy modalities may be output and thus the subscript "n" may be used to designate that up to n $ENERGY_n$ terminals may be provided, where n is a positive integer greater than 1. It also will be appreciated that up to "n" return paths $RETURN_n$ may be provided without departing from the scope of the present disclosure.

A first voltage sensing circuit 912 is coupled across the terminals labeled $ENERGY_1$ and the RETURN path to measure the output voltage therebetween. A second voltage sensing circuit 924 is coupled across the terminals labeled $ENERGY_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 928, 922 and the output of the current sensing circuit 914 is provided to another isolation transformer 916. The outputs of the isolation transformers 916, 928, 922 on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled $ENERGY_1$/RETURN or the second voltage sensing circuit 924 coupled across the terminals labeled $ENERGY_2$/RETURN by the output of the current sensing circuit 914 disposed in series with the RETURN leg of the secondary side of the power transformer 908. The outputs of the first and second voltage sensing circuits 912, 924 are provided to separate isolations transformers 928, 922 and the output of the current sensing circuit 914 is provided to another isolation transformer 916. The digitized voltage and current sensing measurements from the ADC circuit 926 are provided the processor 902 for computing impedance. As an example, the first energy modality $ENERGY_1$ may be RF monopolar energy and the second energy modality $ENERGY_2$ may be RF bipolar energy. Nevertheless, in addition to bipolar and monopolar RF energy modalities, other energy modalities include ultrasonic energy, irreversible and/or reversible electroporation and/or microwave energy, among others. Also, although the example illustrated in FIG. 1 shows a single return path RETURN may be provided for two or more energy modalities, in other aspects, multiple return paths $RETURN_n$ may be provided for each energy modality $ENERGY_n$.

As shown in FIG. 1, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. In one example, a connection of RF bipolar electrodes to the generator 900 output would be preferably located between the output labeled $ENERGY_2$ and RETURN. In the case of monopolar output, the preferred connections would be active electrode (e.g., pencil or other probe) to the $ENERGY_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

Figure 2:
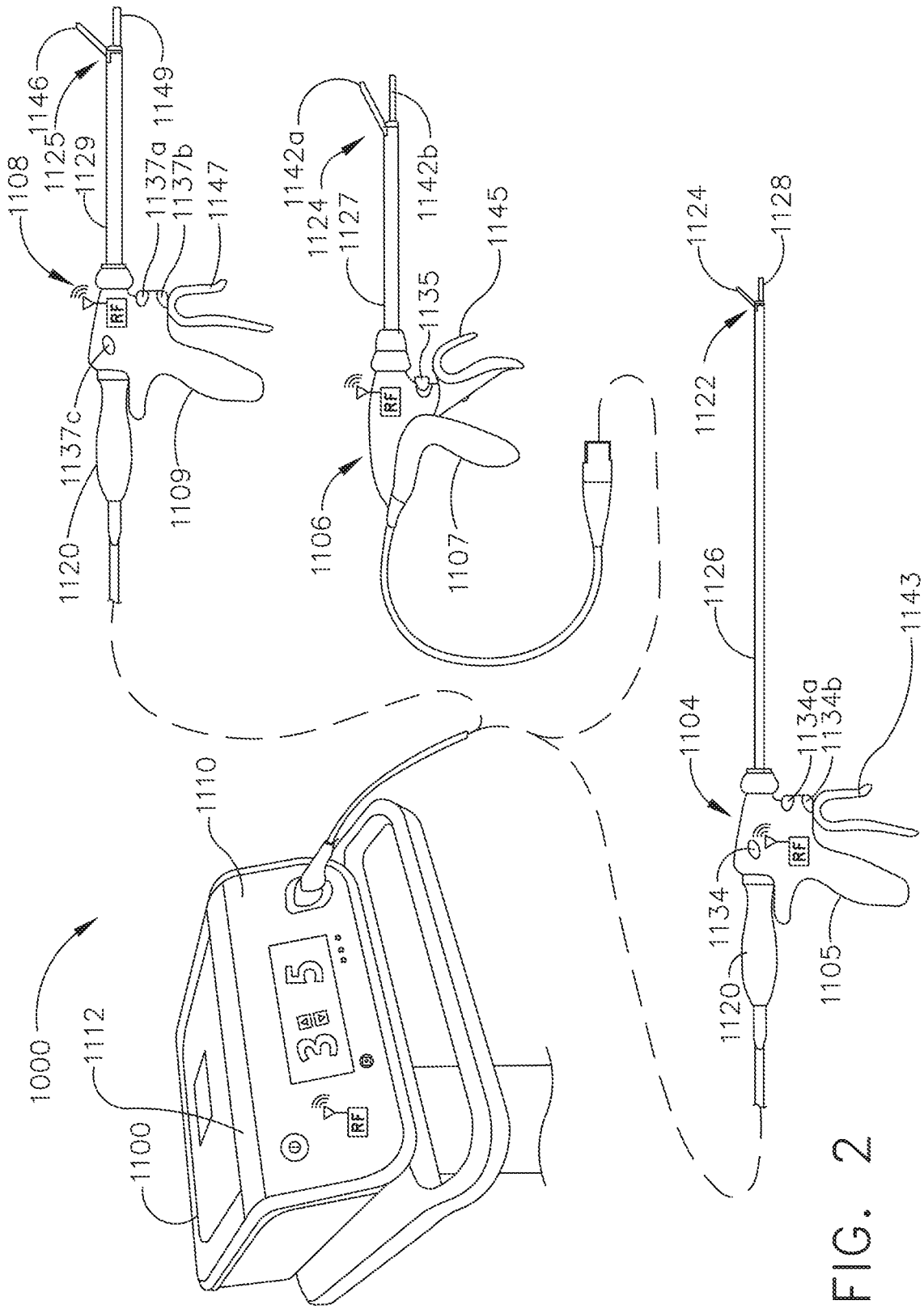
FIG. 2 illustrates one form of a surgical system comprising a generator and an electrosurgical instrument usable therewith, in accordance with at least one aspect of the present disclosure.

FIG. 2 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 2 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1137, 1134b, 1134c to energize and drive the ultrasonic blade 1128 or other function. The toggle buttons 1137, 1134b, 1134c can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1145, 1142b and return through an electrical conductor portion of the shaft 1127. The electrodes are coupled to and energized by a bipolar energy source within the generator 1100. The handpiece 1107 comprises a trigger 1145 to operate the clamp arms 1145, 1142b and an energy button 1135 to actuate an energy switch to energize the electrodes in the end effector 1124. The second surgical instrument 1106 can also be used with a return pad to deliver monopolar energy to tissue.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 11310, 1137b, 1137c to energize and drive the ultrasonic blade 1149 or other function. The toggle buttons 11310, 1137b, 1137c can be configured to energize the ultrasonic transducer 1120 with the generator 1100 and energize the ultrasonic blade 1149 with a bipolar energy source also contained within the generator 1100. Monopolar energy can be delivered to the tissue in combination with, or separately from, the bipolar energy.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 2, the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent application publication US-2017-0086914-A1, which is herein incorporated by reference in its entirety.

Figure 3:
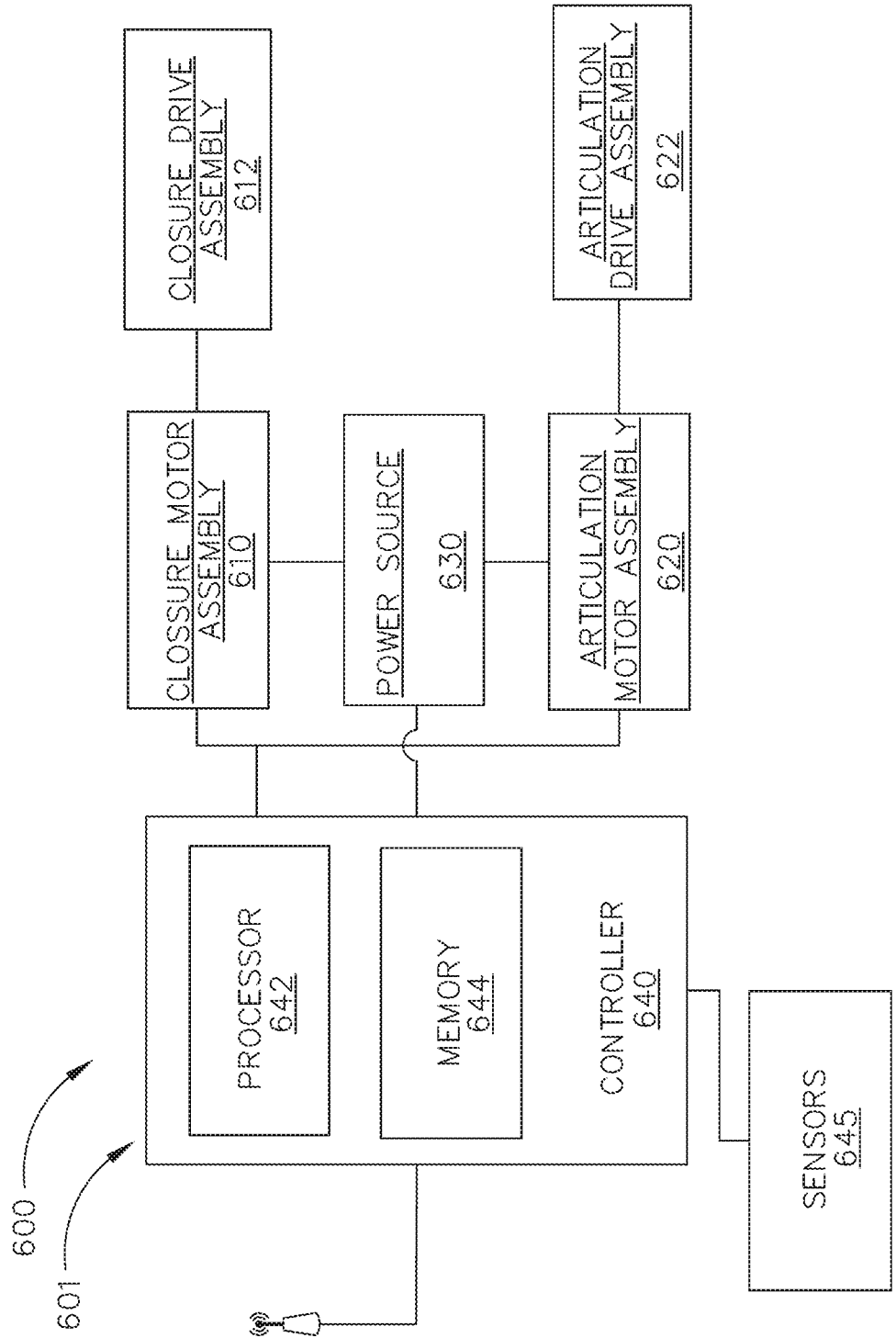
FIG. 3 illustrates a schematic diagram of a surgical instrument or tool, in accordance with at least one aspect of the present disclosure.

FIG. 3 illustrates a schematic diagram of a surgical instrument or tool 600 comprising a plurality of motor assemblies that can be activated to perform various functions. In the illustrated example, a closure motor assembly 610 is operable to transition an end effector between an open configuration and a closed configuration, and an articulation motor assembly 620 is operable to articulate the end effector relative to a shaft assembly. In certain instances, the plurality of motors assemblies can be individually activated to cause firing, closure, and/or articulation motions in the end effector. The firing, closure, and/or articulation motions can be transmitted to the end effector through a shaft assembly, for example.

In certain instances, the closure motor assembly 610 includes a closure motor. The closure 603 may be operably coupled to a closure motor drive assembly 612 which can be configured to transmit closure motions, generated by the motor to the end effector, in particular to displace a closure member to close to transition the end effector to the closed configuration. The closure motions may cause the end effector to transition from an open configuration to a closed configuration to capture tissue, for example. The end effector may be transitioned to an open position by reversing the direction of the motor.

In certain instances, the articulation motor assembly 620 includes an articulation motor that be operably coupled to an articulation drive assembly 622 which can be configured to transmit articulation motions, generated by the motor to the end effector. In certain instances, the articulation motions may cause the end effector to articulate relative to the shaft, for example.

One or more of the motors of the surgical instrument 600 may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, the motor assemblies 610, 620 include one or more motor drivers that may comprise one or more H-Bridge FETs. The motor drivers may modulate the power transmitted from a power source 630 to a motor based on input from a microcontroller 640 (the "controller"), for example, of a control circuit 601. In certain instances, the microcontroller 640 can be employed to determine the current drawn by the motor, for example.

In certain instances, the microcontroller 640 may include a microprocessor 642 (the "processor") and one or more non-transitory computer-readable mediums or memory units 644 (the "memory"). In certain instances, the memory 644 may store various program instructions, which when executed may cause the processor 642 to perform a plurality of functions and/or calculations described herein. In certain instances, one or more of the memory units 644 may be coupled to the processor 642, for example. In various aspects, the microcontroller 640 may communicate over a wired or wireless channel, or combinations thereof.

In certain instances, the power source 630 can be employed to supply power to the microcontroller 640, for example. In certain instances, the power source 630 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 630. In certain instances, the power source 630 may be replaceable and/or rechargeable, for example.

In various instances, the processor 642 may control a motor driver to control the position, direction of rotation, and/or velocity of a motor of the assemblies 610, 620. In certain instances, the processor 642 can signal the motor driver to stop and/or disable the motor. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 642 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 642 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the surgical instrument 600. Accordingly, the present disclosure should not be limited in this context.

In certain instances, the memory 644 may include program instructions for controlling each of the motors of the surgical instrument 600. For example, the memory 644 may include program instructions for controlling the closure motor and the articulation motor. Such program instructions may cause the processor 642 to control the closure and articulation functions in accordance with inputs from algorithms or control programs of the surgical instrument 600.

In certain instances, one or more mechanisms and/or sensors such as, for example, sensors 645 can be employed to alert the processor 642 to the program instructions that should be used in a particular setting. For example, the sensors 645 may alert the processor 642 to use the program instructions associated with closing and articulating the end effector. In certain instances, the sensors 645 may comprise position sensors which can be employed to sense the position of a closure actuator, for example. Accordingly, the processor 642 may use the program instructions associated with closing the end effector to activate the motor of the closure drive assembly 620 if the processor 642 receives a signal from the sensors 630 indicative of actuation of the closure actuator.

In some examples, the motors may be brushless DC electric motors, and the respective motor drive signals may comprise a PWM signal provided to one or more stator windings of the motors. Also, in some examples, the motor drivers may be omitted and the control circuit 601 may generate the motor drive signals directly.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that position during the actuation of the end effector and completion of the surgical procedure. Such articulation joint arrangements must also be able to withstand external forces that are experienced by the end effector during use.

Various modes of one or more surgical devices are often used throughout a particular surgical procedure. Communication pathways extending between the surgical devices and a centralized surgical hub can promote efficiency and increase success of the surgical procedure, for example. In various instances, each surgical device within a surgical system comprises a display, wherein the display communicates a presence and/or an operating status of other surgical devices within the surgical system. The surgical hub can use the information received through the communication pathways to assess compatibility of the surgical devices for use with one another, assess compatibility of the surgical devices for use during a particular surgical procedure, and/or optimize operating parameters of the surgical devices. As described in greater detail herein, the operating parameters of the one or more surgical devices can be optimized based on patient demographics, a particular surgical procedure, and/or detected environmental conditions such as tissue thickness, for example.

Figure 4:
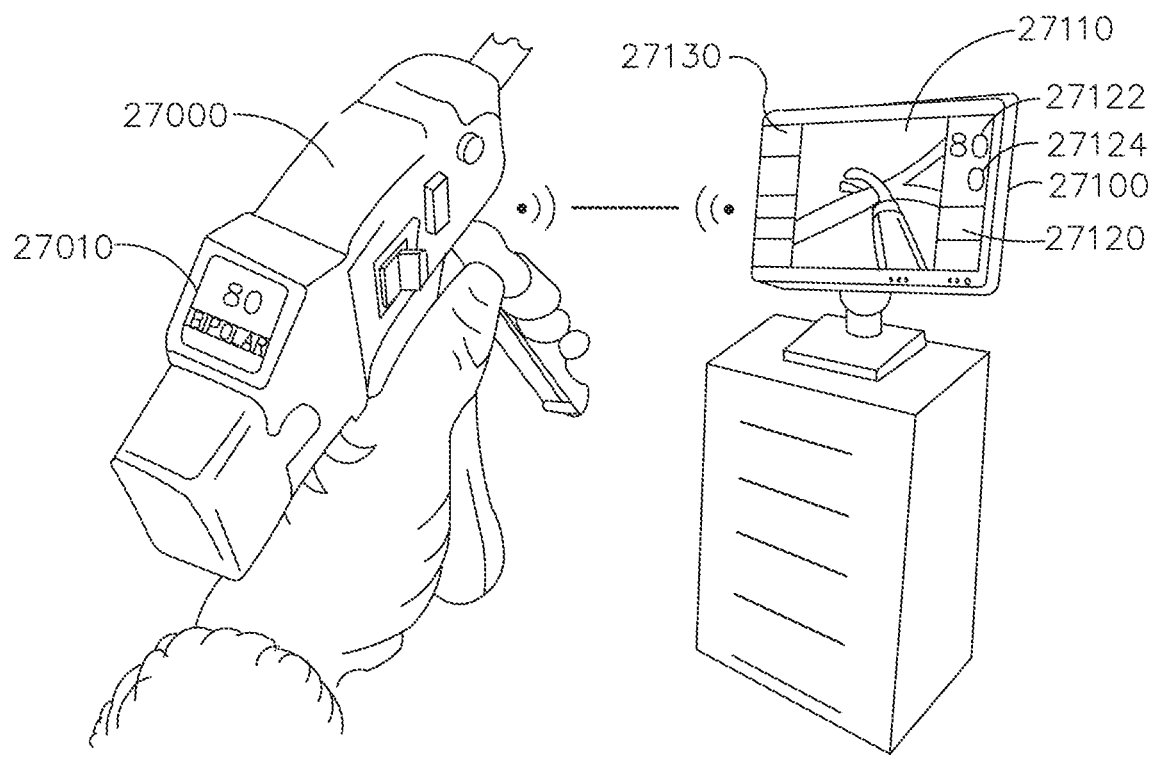
FIG. 4 is a perspective view of a surgical system comprising a surgical instrument and a display monitor, wherein the surgical instrument comprises a display screen in accordance with at least one embodiment.

A divided display system is shown in FIGS. 4-9. The divided display communicates various generator and/or surgical device parameters between a display 27010 of a handheld surgical instrument 27000 and a primary monitor display 27100. FIG. 4 depicts an example of the display 27010 of the handheld surgical instrument 27000. In various instances, the display 27010 includes a touch-sensitive graphical user interface capable of receiving user inputs. The display 27010 comprises various settings and/or modes that allow a user to customize the information and/or images shown on the display 27010 at any given time.

The surgical instrument 27000 is in communication with the main display monitor 27100. The main display monitor 27100 comprises a larger screen than the display 27010 of the surgical instrument 27000. In various instances, the main display monitor 27100 displays the same information and/or images as the display 27010 of the surgical instrument 27000. In other instances, the main display monitor 27100 displays different information and/or images than the display 27010 of the surgical instrument 27000. In various instances, the main display monitor 27100 includes a touch-sensitive graphical user interface capable of receiving user inputs. Similar to the display 27010 of the surgical instrument 27000, the main display monitor 27100 comprises various settings and/or modes that allow a user to customize the information and/or images shown on the main display monitor 27100 at any given time. As described in greater detail herein, a selected mode on the main display monitor 27100 can change the mode of the display 27010 on the surgical instrument 27000 and vice versa. Stated another way, the main display monitor 27100 and the surgical instrument display 27010 co-operate together to communicate the selected operational parameters most effectively to a user.

The depicted handheld surgical instrument 27000 comprises a combination electrosurgical functionality, wherein the surgical instrument 27000 includes an end effector comprising a first jaw and a second jaw. The first jaw and the second jaw comprise electrodes disposed thereon. The electrosurgical instrument 27000 comprises one or more power generators configured to supply power to the electrodes to energize the electrodes. More specifically, energy delivery to patient tissue supported between the first jaw and the second jaw is achieved by energizing the electrodes which are configured to deliver energy in a monopolar mode, bipolar mode, and/or a combination mode. The combination mode is configured to deliver alternating or blended bipolar and monopolar energies. In at least one embodiment, the at least one power generator comprises a battery, a rechargeable battery, a disposable battery, and/or combinations thereof. Various details regarding the operation of the first and second generators is described in greater detail in U.S. patent application Ser. No. 16/562,123, titled METHOD FOR CONSTRUCTING AND USING A MODULAR SURGICAL ENERGY SYSTEM WITH MULTIPLE DEVICES, and filed on Sep. 5, 2019, which is hereby incorporated by reference in its entirety.

The display 27010 of the surgical instrument 27000 and the main display monitor 27100 comprise divided displays to communicate numerous operational parameters to a user. The divided displays are configured to be selectively segmentable. Stated another way, a user is able to select which operational parameters to display and/or where to display the selected operational parameters. Such customization minimizes distraction by eliminating unwanted and/or unnecessary information while allowing the user to efficiently observe the information needed and/or desired to control the surgical instrument 27000 and/or to perform the surgical procedure. The display 27010 of the surgical instrument 27000 comprises a first portion 27012, wherein the power level of a particular mode is displayed. The display 27010 of the surgical instrument 27000 further comprises a second portion 27014, wherein the mode that the surgical instrument 27000 is in and/or the type of energy being delivered by the surgical instrument 27000 is identified, or otherwise communicated.

Similarly, the main display monitor 27100 comprises a segmented display; however, in various instances, the images displayed on the display monitor 27100 can be overlaid onto one another. A central portion 27110 of the main display monitor 27100 streams a live feed and/or still images of a surgical site to the procedure room. The live feed and/or images of the surgical site are captured through an appropriately positioned camera, such as an endoscope. A menu selection portion 27130 of the main display monitor 27100 prompts and/or otherwise allows a user to select which mode the main display monitor 27100 is in and/or what information a user wishes to see on the main display monitor 27100. A device status portion 27120 of the main display monitor 27100 communicates information similar to the first portion 27012 of the surgical instrument display 27010. In various instances, the device status portion 27120 is further divided into multiple sections. For example, a first portion 27122 is configured to communicate an operating parameter reflective of a bipolar mode. Such an operating parameter can be specific and/or generic. A specific operating parameter can reflect the power level of the bipolar mode, for example. A general operating parameter can indicate whether the bipolar mode is active or inactive, for example. A second portion 27124 is configured to communicate an operating parameter reflective of a monopolar mode. Such an operating parameter can be specific and/or generic. A specific operating parameter can reflect the power level of the monopolar mode, for example. A general operating parameter can indicate whether the monopolar mode is active or inactive, for example. A third portion 27126 is configured to communicate an operating parameter reflective of a smoke evacuation system. Such an operating parameter can be specific and/or generic. A specific operating parameter can reflect the power level of the smoke evacuation system, for example. A general operating parameter can indicate whether the smoke evacuation system is active or inactive, for example.

Referring now to FIGS. 5-9, the display 27010 of the surgical instrument 27000 is shown alongside a corresponding display on the main display monitor 27100. As described in greater detail herein, as a user changes a power level on the handheld surgical instrument 27000, such a power level change is reflected on the main display monitor 27100. For example, as shown in FIG. 5, a generator operating the bipolar mode is currently operating at a power level of 80 watts as indicated in the device status portion 27120 of the main display monitor 27100 and the first and second portions 27012, 27014 of the surgical instrument display 27010. More specifically, the first portion 27012 of the surgical instrument display 27010 represents the output of a generator while the second portion 27014 of the surgical instrument display 27010 represents the mode and/or type of energy. Similarly, the device status portion 27120 of the main display monitor 27100 indicates that a generator is operating the bipolar energy mode at a power level of 80 watts and a generator is operating the monopolar energy mode at a power level of zero watts. Upon receiving a command to increase the power output of the generator operating the bipolar mode to 100 watts, the surgical instrument display 27010 and the main display monitor 27100 change accordingly as shown in FIG. 6. More specifically, the first portion 27012 of the surgical instrument display 27010 now represents the power level of 100 watts, and the device status portion 27120 of the main display monitor 27100 now indicates that the generator is operating the bipolar mode at a power level of 100 watts. The main display monitor 27100 continues to indicate that the monopolar energy mode is operating at a power level of zero watts; however, the main display monitor 27100 also indicates that the smoke detection system has been activated to 20% 27126 due to the detection of smoke within the surgical site and/or the increased power level of the surgical instrument.

FIGS. 7-9 depict the display 27010 of the surgical instrument 27000 and the corresponding main display monitor 27100 when a combination of both bipolar and monopolar energies are being delivered to patient tissue. FIG. 7 shows the first portion 27012' of the surgical instrument display 27010 in a total power mode. As shown on the main display monitor 27100, the bipolar energy mode 27122 is operating at a power level of 60 watts and the monopolar energy model 27124 is operating at a power level of 60 watts. However, a combined and/or total power level of 120 watts is represented on the first portion 27012' of the surgical instrument display 27010. The main display monitor 27100 also indicates that the smoke detection system has been activated to 50% 27126 due to the detection of smoke within the surgical site and/or the increased power level of the surgical instrument. As shown in FIG. 8, the user may wish to see the individual power levels of the bipolar mode and the monopolar mode on the first portion 27012" of the surgical instrument display 27010 and the total power level on the device status portion 27122' of the main display monitor 27100. Stated another way, the information shown on the displays in FIG. 8 are reversed from the displays shown in FIG. 7. The main display monitor 27100 further indicates that the smoke detection system has been activated to 73% 27126 due to the detection of smoke within the surgical site and/or the change of power levels of the bipolar and/or monopolar modes. The pair of displays shown in FIG. 9 are similar in many respects to the pair of displays shown in FIG. 8; however, the user has selected to remove the indication of the operating level of the smoke detection system from the main display monitor 27100.

As discussed in greater detail herein, the surgical instrument display 27010 and/or the main display monitor 27100 can comprise touch-sensitive graphical user interfaces. In various instances, the surgical instrument display 27010 is used to control what is being displayed on the surgical instrument display 27010 versus what is being displayed on the main display monitor 27100. In other instances, the main display monitor 27100 is used to control what is being displayed on the surgical instrument display 27010 versus what is being displayed on the main display monitor 27100. In various instances, each display is configured to control what is displayed on its own display. In various instances, each display within a surgical system is configured to cooperatively control what is displayed on other displays within the surgical system.

In various instances, a surgical system comprises an electrosurgical device and a smoke evacuation system. As discussed in greater detail herein, the electrosurgical device is configured to deliver energy to patient tissue supported between the jaws of an end effector by energizing electrodes. The electrodes are configured to deliver energy in a monopolar mode, bipolar mode, and/or a combination mode with alternating or blended bipolar and monopolar energies. In various instances, a first generator is configured to control the bipolar energy modality and a second generator is configured to control the monopolar energy modality. A third generator is configured to control the smoke evacuation system. Various details regarding the operation of the first and second generators is described in greater detail in U.S. patent application Ser. No. 16/562,123, titled METHOD FOR CONSTRUCTING AND USING A MODULAR SURGICAL ENERGY SYSTEM WITH MULTIPLE DEVICES, and filed on Sep. 5, 2019, which is hereby incorporated by reference in its entirety.

Figure 10:
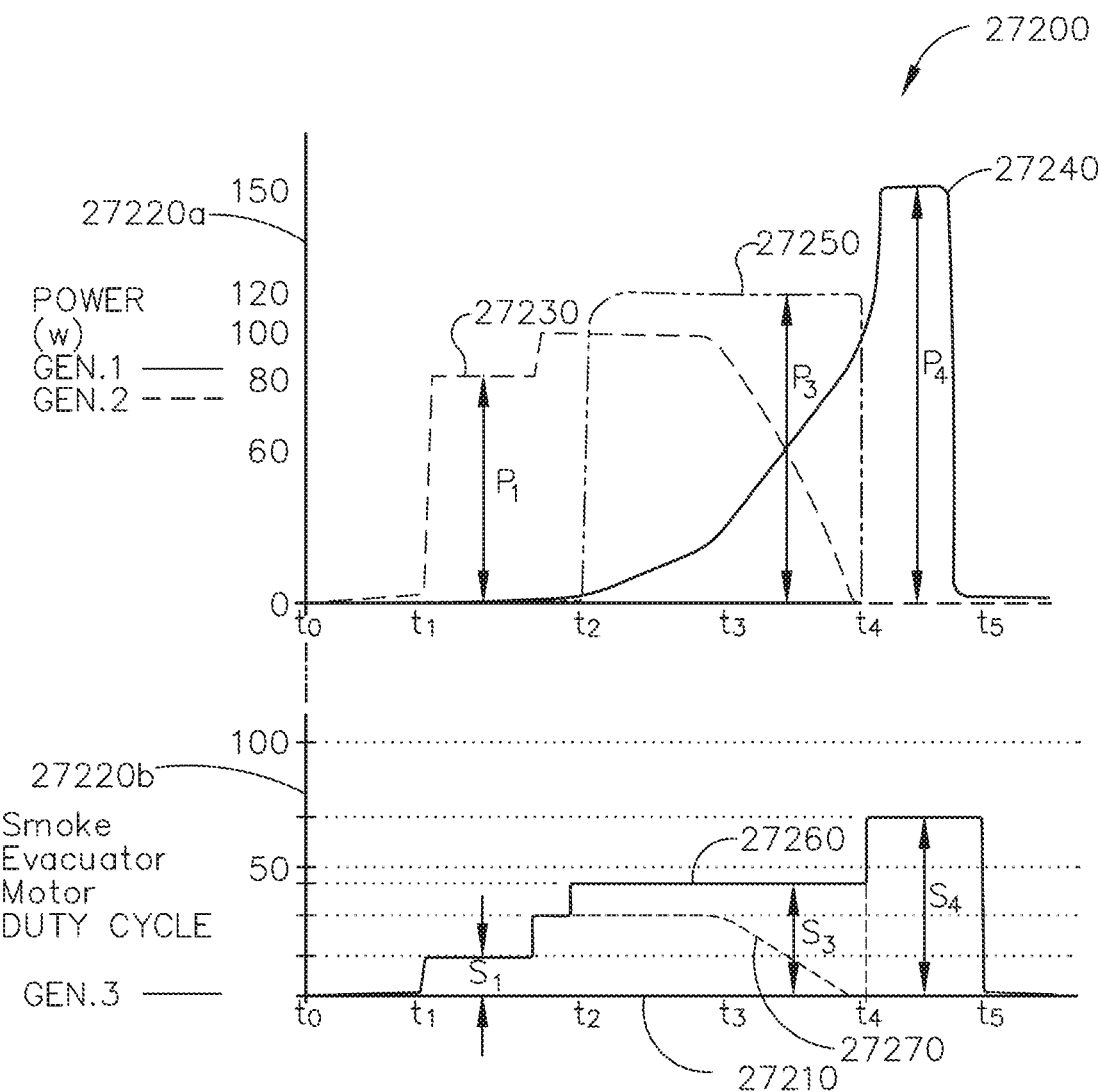
FIG. 10 is a graphical depiction of the relationship between the total effective energy delivered by one or more generators of a surgical system and a duty cycle of a motor from a smoke evacuator in accordance with at least one embodiment.

FIG. 10 is a graphical representation 27200 depicting the proportional relationship between a duty cycle of the smoke evacuation system and the total effective energy delivered to patient tissue. Time 27210 is represented along the x-axis while power (W) 27220a and duty cycle of the smoke evacuation system (%) 27220b are represented along the y-axis. The total effective energy is represented in three facets: (1) bipolar therapy 27230; (2) monopolar therapy 27240; and (3) combined energy 27250. The percentage of the smoke evacuator duty cycle is represented in two facets: (1) in response to the combined energy 27260; and (2) in response to only the bipolar therapy 27270. For example, at time to, power is not being delivered to the patient tissue and the smoke evacuation system is inactive. At time $t_1$, bipolar therapy 27230 is delivered at a first power level $P_1$. At time $t_1$, bipolar therapy 27230 is the only energy delivered to the patient tissue. As the power increased to $P_1$ during the time period of $t_0$ to $t_1$, the smoke evacuation system activated. At time $t_1$, a first percentage $S_1$ of the smoke evacuation duty cycle is utilized.

At time $t_2$, the power level of the bipolar therapy 27230 increased and monopolar therapy 27240 has begun to be delivered. At time $t_3$, the bipolar therapy 27230 decreased while the monopolar therapy 27240 increased. Overall, the combined energy 27250 has remained substantially the same from $t_2$ to $t_3$. At time $t_3$, the combined energy 27250 is delivered at a third power level $P_3$, which is higher than the first power level $P_1$ delivered at time $t_1$. As the power increased to $P_3$ during the time period of $t_1$ to $t_3$, the percentage of the smoke evacuation system duty cycle also increased. At time $t_3$, a third percentage $S_3$ of the smoke evacuation duty cycle is utilized. The third percentage $S_3$ is greater than the first percentage $S_1$. At time $t_4$, delivery of the bipolar therapy 27230 has ceased and the only energy delivered to the patient tissue is through monopolar therapy 27240. Notably, at time $t_4$, the monopolar therapy 27240 delivers energy to the patient tissue at the highest level $P_4$ of monopolar therapy delivered during the entire surgical procedure. Thus, as the delivered energy $P_4$ at time $t_4$ is greater than the delivered energy $P_3$ at time $t_3$, the percentage of the smoke evacuation duty cycle also increased. At time $t_4$, a fourth percentage $S_4$ of the smoke evacuation duty cycle is utilized. The fourth percentage S4 is greater than the third percentage $S_3$ and the first percentage $S_1$.

The graphical representation of FIG. 10 shows bipolar energy 27230 being delivered at varying levels throughout different time points of a surgical procedure. Such time points can correspond to a tissue sealing cycle in which the surgical hub commands the smoke evacuation system to increase or decrease its operating level in response to the current bipolar power level. After the tissue sealing cycle is complete, monopolar energy can be applied for a defined period of time in order to cut the patient tissue. As patient tissue is being cut, the surgical hub can command the smoke evacuation system to increase its operating level based on the increase in energy being applied to cut the tissue as such an increase in applied energy typically corresponds to an increase in smoke from burning tissue, for example. During the particular surgical procedure, the surgical hub is aware of pre-defined time points at which the energy delivery and power levels change. The pre-defined time points can vary based on the type of particular surgical procedure to be performed, for example. The pre-defined time points can vary based on patient demographics identified to the surgical hub, for example. Any detected change in the type of energy being applied and/or the level of energy being applied can trigger responses of different components of the surgical system.

Figure 11:
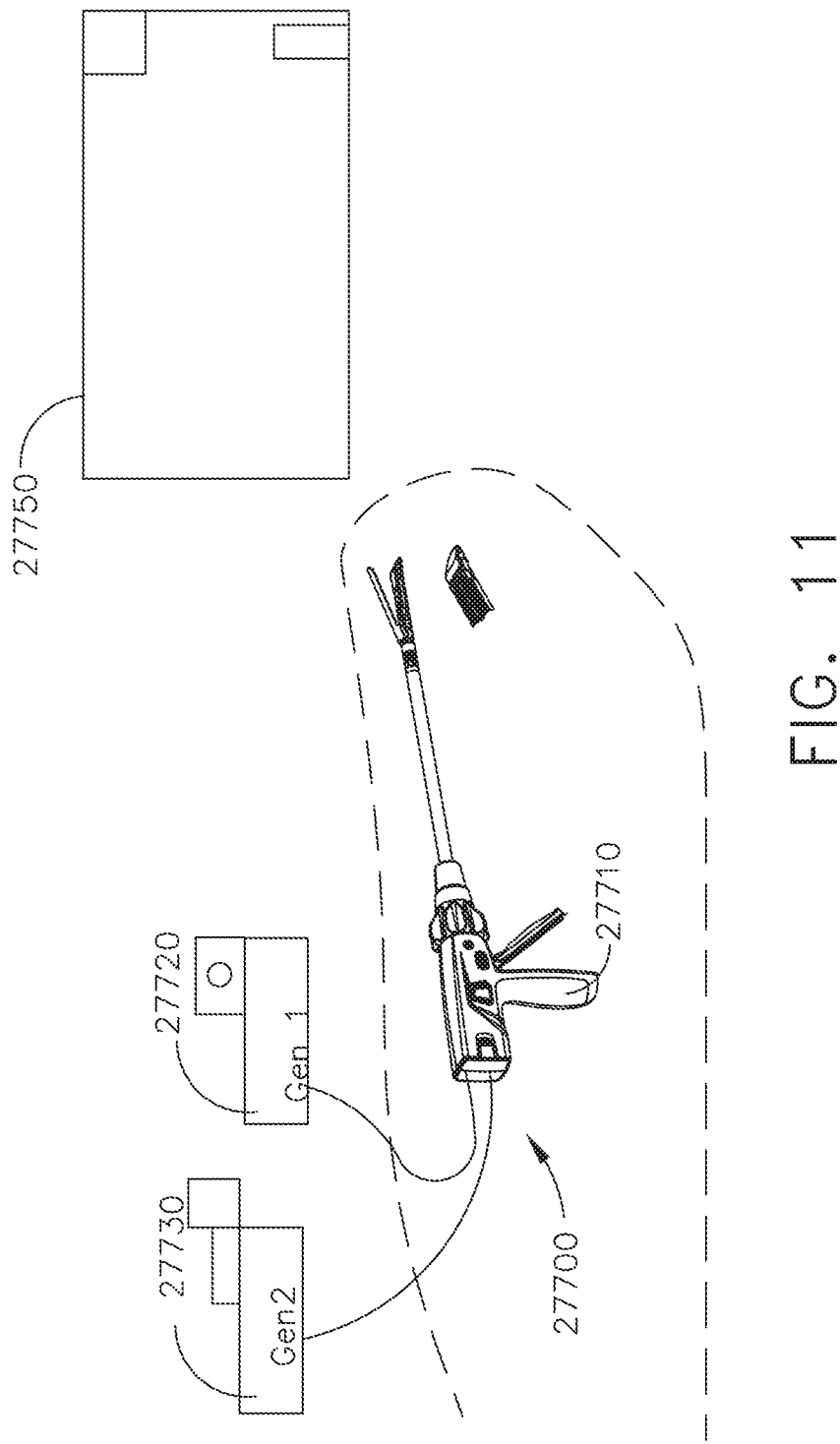
FIG. 11 is a schematic representation of a surgical system comprising a surgical hub, a combination electrosurgical instrument powered by a plurality of generators, a smoke evacuation system, and a display in accordance with at least one embodiment.

Similar to the surgical system described with respect to FIG. 10, a surgical system 27700 depicted in FIG. 11 comprises an electrosurgical instrument 27710 in communication with a surgical hub. The electrosurgical instrument 27710 is configured to deliver energy to patient tissue supported between the jaws of an end effector by electrodes which are configured to deliver energy in a monopolar mode, bipolar mode, and/or a combination mode. The electrosurgical instrument 27710 is configured to apply alternating or blended bipolar and monopolar energies to the patient tissue when in the combination mode. The surgical system 27700 further comprises a first generator 27720 configured to control the monopolar energy modality and a second generator 27730 configured to control the bipolar energy modality. A display screen 27750 is positioned in a location within a procedure room that is within a field of vision of a user. In various instances, the electrosurgical instrument 27710 comprises a display positioned thereon. As the second generator 27730 causes bipolar energy to be delivered to patient tissue, the instrument display and/or the display screen 27750 within the procedure room indicates the level of power being applied. In various instances, a level of smoke evacuation by the smoke evacuation system is indicated on the display(s), wherein the level of smoke evacuation is based on the level of power and/or type of energy being applied. As discussed in greater detail herein, when the first generator 27720 causes monopolar energy to be delivered to patient tissue and/or the second generator 27730 causes a reduced amount of bipolar energy to be delivered to patient tissue, the display(s) are configured to update the displayed, or otherwise communicated, operational parameters. As the levels of power change during the surgical procedure, such changes are communicated to the surgical hub. In response, the surgical hub is configured to automatically, or without an external prompt, alter the level of smoke evacuation to compensate for the changes in the level of energy and/or type of energy being applied to patient tissue.

At least one of the instrument display and the display screen 27750 comprise a touch-sensitive graphical user interface which is configured to receive a user input. The user is able to select what information is displayed, where the selected information is displayed on a particular display, and/or which display within the surgical system displays the desired information. In various instances, the surgical system 27700 further comprises one or more cameras positioned within the procedure room. The one or more cameras are configured to monitor movements of the user and/or the devices of the surgical system. The one or more cameras can communicate any detected movement to the surgical hub, wherein the surgical hub recognizes that the detected movement corresponds to a pre-determined command. For example, a camera can detect when a user waves an arm. A memory within the surgical hub correlates arm waving with the user's desire to clear the display of all operational parameters, so that all that remains on the display is a live feed and/or images of the surgical site. Exemplary commands that can be associated with a specific user and/or instrument movement include adjusting a position of the display(s), adjusting the view of the display(s), adjusting the information presented on the display(s), adjusting the location of the displayed information on a particular display, adjusting the size of the displayed information, controlling power levels of the generator(s), and/or controlling operational parameters of various surgical instruments of the surgical system.

Figure 12:
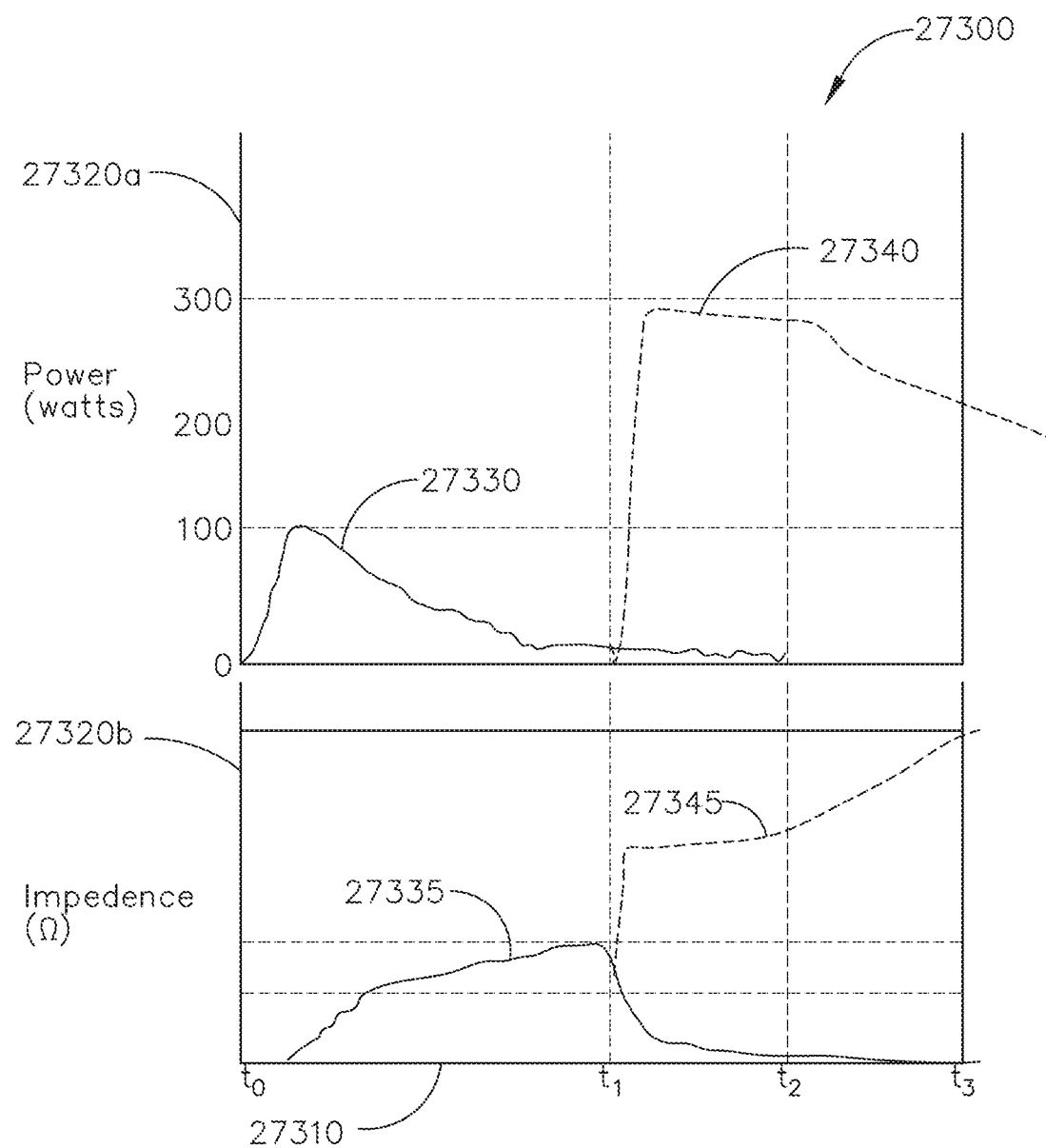
FIG. 12 is a graphical depiction of the relationship between the power supplied by one or more generators of a surgical system over time and the impedance of treated tissue over time in accordance with at least one embodiment.

As discussed with respect to the surgical system 27700, the electrosurgical instrument 27710 comprises a combination electrical modality. A monopolar modality of the electrosurgical instrument is operated by the first generator 27720, while a bipolar modality is operated by a second generator 27730. Monopolar energy is delivered to patient tissue to make an incision, or otherwise cut the treated tissue. Prior to cutting the patient tissue, bipolar energy is delivered to the tissue in order to seal and/or cauterize the target tissue. A graphical representation 27300 of the power level (wattage) of the first generator and the second generators 27320*a* with respect to time (t) 27310 is shown in FIG. 12. The power level is represented in two facets: (1) of the first generator 27340; and (2) of the second generator 27330. The graphical representation 27300 further depicts the relationship of tissue impedance (0) 27320*b* with respect to time (t) 27310. The tissue impedance is represented in two facets (1) in response to the monopolar energy delivered 27345; and (2) in response to the bipolar energy delivered 27335.

As the power level of the second generator 27330 increases from zero, bipolar energy is delivered to patient tissue. The impedance of the patient tissue increases in response to the application of bipolar energy 27335. Notably, the impedance of the patient tissue continues to increase for an amount of time even after the power level of the second generator 27330 begins to decrease. Stated another way, the impedance of the tissue sealed by the bipolar energy 27335 eventually decreases after the power level of the second generator 27330 is reduced absent the delivery of monopolar energy to cut the patient tissue; however, the impedance of the tissue in such instances does not necessarily immediately decrease. At time $t_1$, the power level of the first generator 27340 increases, thereby cutting the tissue through delivery of monopolar energy to the patient tissue. The impedance of the patient tissue also increases in response to the application of monopolar energy 27345. Notably, the impedance of the patient tissue exponentially grows as the tissue is cut and the power level of the first generator 27340 decreases.

FIG. 13 depicts an algorithm 27400 for controlling various components of a surgical system. The surgical system comprises a surgical instrument configured to perform an intended surgical function. In various instances, the surgical instrument is handheld and comprises a handle. A user is configured to operate various modes of the surgical instrument through an input element on the handle. As described in greater detail herein, the surgical instrument comprises a first generator configured to power a monopolar modality and a second generator configured to power a bipolar modality. The surgical system further comprises a smoke evacuation system configured to remove smoke and/or other unwanted particulates from a surgical site. The surgical instrument and/or the smoke evacuation system are in signal communication with a surgical hub, wherein the surgical hub is configured to orchestrate the appropriate response(s) of the components of the surgical system in response to a user input on the surgical instrument, the smoke evacuation system, and/or another component within the surgical system.

As shown in FIG. 13, a control algorithm 27400 begins when a user changes a mode 27410 of the surgical instrument. For example, the user may wish to increase the power level of the first generator to cut patient tissue. In another example, the user may wish for the surgical instrument to seal and/or cut patient tissue. In any event, the surgical instrument then communicates 27412, 27414 the user input to the first generator and the second generator, respectively. The surgical instrument further communicates 27415 the user input to the surgical hub. After the surgical hub is informed 27420 of the desired increase in monopolar energy, the surgical hub is configured to command the second generator 27425 to supply and/or administer an appropriate power level. Upon receiving the communication 27412 from the surgical instrument, the first generator increases a waveform 27440 in preparation for cutting patient tissue. Upon receiving the communication 27414 from the surgical instrument and the command 27425 from the surgical hub, the second generator increases the power level associated with the bipolar modality 27450 in preparation for sealing the patient tissue after the cut is performed. The second generator can then communicate 27455 its readiness to the first generator. The first generator is then able to start cutting the patient tissue 27442. Stated another way, the surgical hub prevents a monopolar electrode from being energized until the bipolar electrode has been energized to prevent cutting of tissue that has not been cauterized and/or sealed. The surgical hub is further configured to command 27426 the smoke evacuation system to increase a motor rate in response to an increase in power levels of the first and second generators. After the smoke evacuation system increases its motor rate 27430, the smoke evacuation system is configured to maintain a line of communication with the surgical hub, the surgical instrument, and/or the first and second generators throughout the duration of the surgical procedure. For example, the smoke evacuation system is configured to continuously communicate a current motor rate 27435 to the surgical hub. In such instances, the smoke evacuation system sends its current motor rate to the surgical hub every minute, or every two minutes; however, the smoke evacuation system is able to communicate its current motor rate at any suitable frequency. Upon the surgical instrument completing the desired tissue cut, the user can once again provide an input on the instrument handle to reduce the power level of the first generator and/or end the control algorithm 27400. In various instances, the control algorithm 27400 is configured to automatically reduce the power level of the first generator after a pre-determined period of time that corresponds to a completion a tissue cut. Utilizing the control algorithm 27400, the surgical hub is able to orchestrate the operating parameters of the components of the surgical system to facilitate an efficient and/or effective surgical procedure, for example.

Numerous surgical devices, tools, and/or replaceable components are often used during a particular surgical procedure. Various systems are disclosed herein that serve to, among other things, streamline the devices and/or components that are stocked within a procedure room for use during a particular procedure, minimize operator error, and/or minimize delays during surgical procedures. The systems described herein increase the efficiency of surgical procedures using, among other things, artificial intelligence and machine learning developed over the course of one or more surgical procedures.

Various components of an exemplary surgical system 27500 are shown in FIG. 14. During a particular surgical procedure, a patient rests on an operating table, or any suitable procedure surface 27510. In various instances, the particular procedure is performed at least in part using a surgical robot. The surgical robot comprises one or more robot arms 27520. Each robot arm 27520 is configured to receive a tool component 27590. The tool components 27590 are configured to cooperate with one another to perform and/or assist the clinician in performing the particular surgical procedure. The tool components may comprise, for example, a surgical stapling and/or tissue cutting tool component, a tissue grasping tool component, and/or an electrosurgical tool component. The tool components may comprise other distinguishing characteristics such as, for example, size, manufacturer, date of manufacture, number of previous uses, and/or expiration date.

The surgical system 27500 further comprises a surgical hub 27530. Various surgical hubs are described in described in U.S. patent application Ser. No. 16/209,395, titled METHOD OF HUB COMMUNICATION, and filed on Dec. 4, 2018, which is hereby incorporated by reference in its entirety. The surgical hub 27530 comprises a memory 27535 that stores various suitable, or otherwise appropriate, combinations of tool components 27590 to be used during the particular procedure. Stated another way, the memory 27535 of the surgical hub 27530 comprises a stored information bank which can be used to indicate which tool components 27590 are appropriate for utilization during a selected procedure.

Prior to performing a desired surgical procedure, a clinician can notify, or otherwise communicate, details relating to the desired surgical procedure and/or the patient to the surgical hub 27530. Such details can include, for example, an identity of the surgical procedure, an identity of the clinician performing the surgical procedure, and/or a biometric profile of the patient, for example. The surgical hub 27530 is then configured to utilize one or more of the communicated details to evaluate and/or determine which tool components 27950 are necessary and/or appropriate to perform the desired surgical procedure. In various instances, the surgical hub 27530 is configured to assess which modes of each tool components 27950 are appropriate for performing the desired surgical procedure on the particular patient.

As shown in FIG. 14, four robot arms 27250 surround, or are otherwise attached to, the operating table 27510. Three tool components 27590 are connected to three corresponding robot arms 27250, leaving one robot arm free to receive an additional tool component. A plurality of unique tool components 27560, 27570, 27580 are shown stored on a moving stand 27550 within the procedure room. As discussed above, the type and/or functionality of the tool components 27560, 27570, 27580 can be different. In such instances, the surgical hub 27530 evaluates the available tool components 27560, 27570, 27580 and identifies an appropriate tool component for attachment to the surgical robot. An appropriate tool component is identified based on one or more factors such as, which tool-type and/or function is still needed by the surgical robot and/or which tool component completes a pre-determined pairing of tool components that is associated with the desired surgical procedure, for example. In various instances, the surgical robot comprises a memory storing pre-determined tool component pairings based on a particular surgical procedure and/or a particular patient demographic, for example. In such instances, the surgical robot is able to identify an appropriate tool component for attachment to the surgical robot based on the identity of the tool components already attached.

In other instances, the tool components 27560, 27570, 27580 comprise the same type and/or functionality; however, the tool components 27560, 27570, 27580 comprise at least one other distinguishing characteristic such as, for example, a difference in size, manufacturer, expiration date, and/or number of previous uses. The surgical hub 27530 evaluates a profile of each available tool component 27560, 27570, 27580 and identifies an appropriate tool component based on which characteristics are compatible with the profiles of the other selected and/or attached tool components 27590.

As shown in FIG. 14, each tool component 27560, 27570, 27580 comprises a QR code 27565, 27575, 27585 positioned at any suitable location thereon, wherein each QR code contains a profile of information representative of the tool component to which the QR code is coupled. A user scans and/or reads the QR codes 27565, 27575, 27585 using any appropriate scanning tool 27540. The scanning tool 27540 then communicates the QR code and/or the information contained within the QR code to the surgical hub 27530. In instances where the QR code itself is communicated by the scanning tool 27540 to the surgical hub 27530, a processor of the surgical hub 27530 is configured to decrypt the profile of information contained by the received QR code. While the depicted embodiment comprises QR codes, the tool components can comprise any suitable memory device such as a barcode, an RFID tag, and/or a memory chip, for example.

The surgical hub 27530 is configured to alert a user when a tool component is not acceptable and/or desirable for use during the surgical procedure. Such an alert can be communicated through various forms of feedback, including, for example, haptic, acoustic, and/or visual feedback. In at least one instance, the feedback comprises audio feedback, and the surgical system 27500 can comprise a speaker which emits a sound, such as a beep, for example, when an error is detected. In certain instances, the feedback comprises visual feedback and the tool components can each comprise a light emitting diode (LED), for example, which flashes when an error is detected. In certain instances, the visual feedback can be communicated to a user through an alert presented on a display monitor within a field of vision of the clinician. In various instances, the feedback comprises haptic feedback and a component of the surgical system 27500 can comprise an electric motor comprising an eccentric element which vibrates when an error is detected. The alert can be specific or generic. For example, the alert can specifically state that the QR code on the tool component is unable to be detected, or the alert can specifically state that the QR code comprises information representative of an incompatible and/or defective tool component.

For example, a user attempts to attach a first tool component 27560 to the available robot arm 27590 of the surgical robot. Prior to attaching the first tool component 27560 to the robot arm 27590, the scanning tool 27540 scans the QR code 27565 displayed on the first tool component 27560. The scanning tool 27540 communicates the QR code 27565 and/or the information contained within the QR code 27565 to the surgical hub 27530. The surgical hub 27530 compares the information contained within the QR code 27565 to a stored list of acceptable tool components associated with the particular surgical procedure and/or a stored list of acceptable tool components compatible with the tool components that are currently attached to the surgical robot. In this instance, the surgical hub 27530 fails to recognize and/or locate the first tool component 27560 within its memory 27535. Thus, the first tool component 27560 is not recommended and/or appropriate for use with the surgical robot. As discussed above, the surgical hub 27530 is configured to alert the clinician of the incompatibility of the first tool component 27560 with the surgical robot and/or the particular surgical procedure. In various instances, the surgical system 27500 can prevent the first tool component 27560 from being attached thereto through a mechanical and/or electrical lockout, for example. Such an attachment lockout prevents a clinician from missing and/or simply ignoring the alert issued by the surgical system 27500. Stated another way, the attachment lockout requires the clinician to take affirmative steps in overriding the error communicated by the surgical system 27500. In such instances, an override can be activated to allow the clinician to override any system lockout and utilize operational functions of the first tool component 27560. In various instances, an override is unavailable in order to prevent a clinician from utilizing the functionality of the first tool component 27560 while the first tool component 27560 is recognized as incompatible for use with the surgical robot.

Similarly, a user attempts to attach a second tool component 27570 to the available robot arm 27590 of the surgical robot. Prior to attaching the second tool component 27570 to the robot arm 27590, the scanning tool 27540 scans the QR code 27575 displayed on the second tool component 27570. The scanning tool 27540 communicates the QR code 27575 and/or the information contained within the QR code 27575 to the surgical hub 27530. The surgical hub 27530 compares the information contained within the QR code 27575 to a stored list of acceptable tool components associated with the particular surgical procedure and/or a stored list of acceptable tool components compatible with the tool components that are currently attached to the surgical robot. In this instance, the surgical hub 27530 fails to recognize and/or locate the second tool component 27570 within its memory 27535. Thus, the second tool component 27570 is not recommended and/or appropriate for use with the surgical robot. As discussed above, the surgical hub 27530 is configured to alert the clinician of the incompatibility of the second tool component 27570 with the surgical robot and/or the particular surgical procedure. In various instances, the surgical system 27500 can prevent the second tool component 27570 from being attached thereto. Such an attachment lockout prevents a clinician from missing and/or simply ignoring the alert issued by the surgical system 27500. Stated another way, the attachment lockout requires the clinician to take affirmative steps in overriding the error communicated by the surgical system 27500. In such instances, an override can be activated to allow the clinician to override any system lockout and utilize operational functions of the second tool component 27570. In various instances, an override is unavailable in order to prevent a clinician from utilizing the functionality of the second tool component 27570 while the second tool component 27570 is recognized as incompatible for use with the surgical robot.

A user attempts to attach a third tool component 27580 to the available robot arm 27590 of the surgical robot. Prior to attaching the third tool component 27580 to the robot arm 27590, the scanning tool 27540 scans the QR code 27585 displayed on the third tool component 27580. The scanning tool 27540 communicates the QR code 27585 and/or the information contained within the QR code 27585 to the surgical hub 27530. The surgical hub 27530 compares the information contained within the QR code 27585 to a stored list of acceptable tool components associated with the particular surgical procedure and/or a stored list of acceptable tool components compatible with the tool components that are currently attached to the surgical robot. In this instance, the surgical hub 27530 successfully recognizes and/or locates the third tool component 27580 within its memory 27535. The third tool component 27580 is then determined to be appropriate for use with the surgical robot during the particular surgical procedure and/or with the other attached tool components. In various instances, the surgical hub 27530 is configured to alert the clinician of the compatibility of the third tool component 27580 with the surgical robot. In other instances, the surgical system 27500 simply does not prevent the attachment of the third tool component 27580 to the available robot arm 27590.

In various instances, the memory 27535 of the surgical hub 27530 is configured to store the QR codes associated with each tool component used during a particular surgical procedure. The surgical hub 27530 can then analyze the collected information to form observations and/or conclusions regarding factors such as, for example, the efficiency and/or the effectiveness of a particular tool component and/or a plurality of tool components during a surgical procedure. The observations and/or conclusions can then be used by the surgical hub 27530 in selecting and/or recommending which tool components to utilize during future surgical procedures.

FIG. 15 depicts a surgical system 27600 comprising one or more cameras configured to assist a clinician in performing an efficient and/or successful surgical procedure. Similar to the surgical system 27500, the surgical system 27600 comprises an operating table 27610, or any suitable procedure surface. The surgical system 27600 further comprises a surgical hub 27650, and a device tower 27660. Various surgical hubs are described in described in U.S. patent application Ser. No. 16/209,395, titled METHOD OF HUB COMMUNICATION, and filed on Dec. 4, 2018, which is hereby incorporated by reference in its entirety.

The surgical system 27600 further comprises a camera system including one or more cameras 27640 positioned at various locations throughout the procedure room. In the depicted embodiment, two cameras 27640 are positioned in opposing corners of the procedure room; however, the cameras 27640 can be positioned and/or oriented in any suitable location that allows the cameras 27640 to cooperatively capture the procedure room in an unimpeded manner. An artificial intelligence protocol detects and/or identifies various devices, equipment and/or personnel and their corresponding locations and/or orientations within the procedure room.

The cameras 27640 of the camera system are in communication with the surgical hub 27650. Stated another way, the live feeds of the cameras 27640 can be transmitted to the surgical hub 27650 for processing and analysis. Through analysis of the footage collected by the cameras 27640, the surgical hub 27650 is able to maintain a real-time inventory of the devices, equipment, and/or personnel within the procedure room and/or monitor and/or control the interactions between the detected devices, equipment and/or personnel. Using the images and/or data collected by the camera system, the surgical hub 27650 is configured to be informed regarding the identities of the detected devices, alert a clinician regarding compatibility concerns about the detected devices, and/or control various components of the surgical system 27600 based on the presence and/or operation of the detected devices. The surgical hub 27650 is configured to compare any detected devices to determine compatibility between the devices and/or during the particular surgical procedure, facilitate the cooperation of two devices that are intended to work together, and/or facilitate the cooperation of two devices that build off of one another's sensed and/or controlled operations.

As shown in FIG. 15, an anesthesia cart 27670 and a preparation table 27620 are positioned within a procedure room. The preparation table 27620 is configured to support various surgical tools and/or devices in a manner that makes them easily accessible for use during a surgical procedure. Such surgical tools and/or devices can include replaceable staple cartridges of varying sizes or shaft assemblies comprising end effectors of varying sizes and/or functionalities, for example. In the depicted embodiment, the preparation table 27620 supports a first device 27630*a*, a second device 27630*b*, and a third device 27630*c*.

The cameras 27640 are configured to detect identifying information regarding the devices, equipment, and/or personnel located within the procedure room. For example, the cameras 27640 can capture a serial number printed on a visible portion of each device 27630*a*, 27630*b*, 27630*c*, such as on a packaging of the devices, for example. In various instances, the packaging comprises a QR code printed thereon which contains information regarding a device contained therein. The QR code is captured by the cameras 27640 and communicated to the surgical hub 27650 for analysis and identification of the staple cartridge.

Such an identification system can be useful, for example, during a surgical procedure in which a surgical stapling instrument comprising an end effector, wherein a 60 mm staple cartridge is configured to be seated within the end effector. The cameras 27640 within the procedure room are configured to capture the presence of a surgical stapling instrument in the form of a live video feed and/or a still image, for example. The cameras 27640 then communicate the captured image(s) to the surgical hub 27650. The surgical hub 27650 is configured to identify the surgical stapling instrument based on the image(s) received from the cameras 27640. In instances where the surgical hub 27650 is aware of the surgical procedure to be performed, the surgical hub 27650 can alert the clinician as to whether or not the identified surgical stapling instrument is appropriate. For example, knowing that a 45 mm staple cartridge is associated with a particular surgical procedure, the surgical hub 27650 can alert the clinician that the detected surgical stapling instrument is inappropriate, as the end effector of the detected surgical stapling instrument is configured to receive a 60 mm staple cartridge.

The surgical hub 27650 comprises a memory 27655 that stores the technical requirements and/or specifications associated with various devices therein. For example, the memory 27655 of the surgical hub 27650 recognizes that the surgical stapling instrument described above is configured to receive a 60 mm staple cartridge. In various instances, the memory 27655 can also recognize a particular brand of 60 mm staple cartridges compatible with the surgical stapling instrument. In various instances, the cameras 27640 can capture the presence of replaceable staple cartridges in the form of a live video feed and/or a still image, for example. The cameras 27640 then communicate the captured image(s) to the surgical hub 27650. The surgical hub 27650 is configured to identify a characteristic of the replaceable staple cartridge based on the image(s) received from the cameras 27640. Such characteristics include, for example, a size, a brand, and/or a manufacturing lot. As discussed in greater detail herein, the alert can be specific or generic. In instances where the cameras 27640 capture the presence of packaging containing a replaceable 45 mm staple cartridge, the surgical hub 27650 is configured to alert the clinician that an incompatible staple cartridge has been mistakenly stocked within the room. Such an alert can prevent surgical instrument malfunction, injury to the patient, and/or valuable time loss during the surgical procedure, for example.

As discussed above, the camera system is configured to facilitate the surgical hub 27650 in coordinating the devices detected within the procedure room. In various instances, a combination energy device and a smoke evacuation system are detected by the camera system. The combination energy device is configured to apply bipolar energy and monopolar energy to patient tissue. As the camera system and/or the surgical hub 27650 detects an activation of the combination energy device, the presence of the combination energy device at a position near the patient, and/or the presence of smoke in the procedure room, the surgical hub 27650 is configured to direct a generator to enable the smoke evacuation system, for example.

A surgical instrument can utilize a measurable, or otherwise detectable, characteristic of an end effector to confirm a particular stage of the surgical procedure and/or to control various operational parameters of the surgical instrument. Such a characteristic can include, for example, a distance between the jaws of the end effector. A memory of the surgical instrument and/or the surgical hub comprises stored information that associates a particular jaw gap distance with a particular stage of a surgical procedure. For example, when the distance between the jaws is measured between 0.030 inches and 0.500 inches, the surgical instrument and/or the surgical hub confirms that the end effector is delivering bipolar energy to patient tissue. In other instances, when the distance between the jaws is measured between 0.030 inches and 0.500 inches, the surgical instrument and/or the surgical hub activates a generator, thereby initiating the delivery of bipolar energy to the patient tissue. Stated another way, a detection of a characteristic of the surgical instrument and/or contacted patient tissue can be used by the surgical instrument and/or the surgical hub in order to confirm and/or adapt the operation of the surgical instrument.

FIG. 16 comprises a chart depicting various operational parameters and/or specifications of a surgical instrument that correspond to various stages of a surgical procedure. Similar to the surgical instruments described in greater detail herein, the surgical instrument 27000 depicted in FIGS. 17-19 comprises a combination electrosurgical functionality, wherein the surgical instrument includes an end effector comprising a first jaw 27810 and a second jaw 27820. At least one of the first jaw 27810 and the second jaw 27820 are movable with respect to one another, and the end effector is configurable between an open configuration and a closed configuration. The first jaw 27810 comprises a first tissue-supporting and/or tissue-contacting surface 27815, and the second jaw 27820 comprises a second tissue-supporting and/or tissue-contacting surface 27825. The first jaw 27810 and the second jaw 27810 comprise electrodes disposed thereon. The electrosurgical instrument 27000 comprises one or more power generators configured to supply power to the electrodes to energize the electrodes. More specifically, energy delivery to patient tissue supported between the first jaw and the second jaw is achieved by the electrodes which are configured to deliver energy in a monopolar mode, bipolar mode, and/or a combination mode. Alternating or blended bipolar and monopolar energies are configured to be delivered in the combination mode. In at least one embodiment, the at least one power generator comprises a battery, a rechargeable battery, a disposable battery, and/or combinations thereof.

The end effector 27800 is used to perform various end effector functions during the surgical procedure. At an original time $t_0$, the end effector 27800 is not in contact with the patient tissue $T_{t0}$. Thus, the electrodes of the end effector 27800 are not delivering any energy. At the original time $t_0$, the patient tissue $T_{t0}$ is in a relaxed, uncompressed state. The end effector 27800 is shown in the open configuration. In the open configuration, a distance $d_0$ spans anywhere from 0.500 inches to 0.700 inches between the first tissue-supporting surface 27815 and the second tissue-supporting surface 27825. Stated another way, the tissue-supporting surfaces 27815, 27825 are separated a maximum distance do of 0.500 inches to 0.700 inches from one another when the end effector 27800 is in the open configuration.

At a first time $t_1$, the jaws 27810, 27820 of the end effector 27800 are brought into contact with the patient tissue $T_{t1}$. At least a portion of the patient tissue $T_{t1}$ is positioned in between the jaws 27810, 27820 of the end effector 27800 as the end effector 27800 moves from the open configuration toward the closed configuration. As the jaws 27810, 27820 are moved toward the closed configuration, the tissue $T_{t1}$ is compressed therebetween. At time $t_1$, the end effector 27800 is configured to deliver bipolar energy to the patient tissue $T_{t1}$. The application of bipolar energy allows the end effector 27800 to feather through parenchymal cells, for example. The end effector 27800 is in a partially closed configuration at time $T_1$. A first distance $d_1$ spans anywhere from 0.030 inches to 0.500 inches between the first tissue-supporting surface 27815 and the second tissue-supporting surface 27825 at time $t_1$. Stated another way, the tissue-supporting surfaces 27815, 27825 are separated a maximum first distance $d_1$ of 0.030 inches to 0.500 inches when the end effector is delivering bipolar energy to the patient tissue $T_{t1}$ at time $t_1$. A detailed depiction of the jaws 27810, 27820 of the end effector 27800 delivering bipolar energy to the patient tissue $T_{t1}$ at a first time $t_1$ is shown in FIG. 17.

At a second time $t_2$, the jaws 27810, 27820 of the end effector 27800 maintain contact with the patient tissue $T_{t2}$. At least a portion of the patient tissue $T_{t2}$ is positioned in between the jaws 27810, 27820 of the end effector 27800. At time $t_2$, the end effector 27800 is configured to deliver a combination of bipolar and monopolar energies to the patient tissue $T_{t2}$. The application of bipolar energy and monopolar energy allows the end effector 27800 to warm the patient tissue $T_{t2}$. The end effector 27800 is in a partially closed configuration at time $t_2$; however, the end effector 27800 is closer to a fully-closed configuration at time $t_2$ than the end effector 27800 at time $t_1$. More specifically, a second distance $d_2$ spans anywhere from 0.010 inches to 0.030 inches between the first tissue-supporting surface 27815 and the second tissue-supporting surface 27825 at time $t_2$. Stated another way, the tissue-supporting surfaces 27815, 27825 are separated a maximum second distance $d_2$ of 0.010 inches to 0.030 inches when the end effector is delivering bipolar and monopolar energies to the patient tissue $T_{t2}$ at time $t_2$. A detailed depiction of the jaws 27810, 27820 of the end effector 27800 delivering bipolar and monopolar energies to the patient tissue $T_{t2}$ at a second time $t_2$ is shown in FIG. 18.

At a third time $t_3$, the jaws 27810, 27820 of the end effector 27800 maintain contact with the patient tissue $T_{t3}$. At least a portion of the patient tissue $T_{t3}$ is positioned in between the jaws 27810, 27820 of the end effector 27800. At time $t_3$, the end effector 27800 is configured to continue delivering a combination of bipolar and monopolar energies to the patient tissue $T_{t3}$. The continued application of bipolar energy and monopolar energy allows the end effector 27800 to seal the patient tissue $T_{t3}$. The end effector 27800 is in a partially closed and/or fully-closed configuration at time $t_3$. Stated another way, the end effector 27800 is in the fully-closed configuration and/or closer to the fully-closed configuration at time $t_3$ than the end effector 27800 at time $t_2$. More specifically, a third distance $d_3$ spans anywhere from 0.003 inches to 0.010 inches between the first tissue-supporting surface 27815 and the second tissue-supporting surface 27825 at time $t_3$. Stated another way, the tissue-supporting surfaces 27815, 27825 are separated a maximum third distance $d_3$ of 0.003 inches to 0.100 inches when the end effector is delivering bipolar and monopolar energies to the patient tissue $T_{t3}$ at time $t_3$. A detailed depiction of the jaws 27810, 27820 of the end effector 27800 delivering bipolar and monopolar energies to the patient tissue at a third time $t_3$ is also shown in FIG. 18.

At a fourth time $t_4$, the jaws 27810, 27820 of the end effector 27800 maintain contact with the patient tissue M. At least a portion of the patient tissue $T_{t4}$ is positioned in between the jaws 27810, 27820 of the end effector 27800 as the end effector 27800. At time $t_4$, the end effector 27800 is configured to deliver monopolar energy to the patient tissue $T_{t4}$. The application of monopolar energy allows the end effector 27800 to cut through the patient tissue $T_{t4}$. The end effector 27800 is in a partially closed and/or fully-closed configuration at time $t_4$. Stated another way, the end effector 27800 is in the fully-closed configuration and/or closer to the fully-closed configuration at time $t_4$ than the end effector 27800 at time $t_2$. More specifically, a fourth distance $d_4$ spans anywhere from 0.003 inches to 0.010 inches between the first tissue-supporting surface 27815 and the second tissue-supporting surface 27825 at time $t_4$. Stated another way, the tissue-supporting surfaces 27815, 27825 are separated a maximum fourth distance $d_4$ of 0.003 inches to 0.010 inches when the end effector is delivering monopolar energy to the patient tissue $T_{t4}$ at time $t_4$. A detailed depiction of the jaws 27810, 27820 of the end effector 27800 delivering monopolar energy to the patient tissue T14 at a fourth time $t_4$ is shown in FIG. 19.

The graph 27900 shown in FIG. 20 illustrates the relationships between various operational parameters and/or specifications of the surgical instrument of FIGS. 16-19 with respect to time. The surgical instrument and/or the surgical hub can utilize the depicted relationships to confirm proper functionality of the surgical instrument during the surgical procedure and/or to operate and/or adjust various functionalities of the surgical instrument in response to one or more measured parameters. The graph illustrates (1) the change 27930 in the power (W) 27920a of a generator controlling a bipolar modality of the surgical instrument time 27910; (2) the change 27935 in the power (W) 27920a of a generator controlling a monopolar modality of the surgical instrument over time 27910; (3) the change 27940 in the distance between the jaws of the end effector 27920b over time 27910; (4) the change 27950 in the force of the jaw motor (F) 27920c over time 27910; and (5) the change 27960 in the velocity of the jaw motor (V) 27920d over time 27910.

At time $t_0$, the electrodes of the end effector are not delivering energy to patient tissue, and the end effector is not yet in contact with patient tissue. The distance 27920b between the jaws of the end effector is at a maximum at time $t_0$ due to the end effector being in the open configuration. The force to clamp 27950 the jaws is minimal from time $t_0$ to time $t_1$ as the end effector experiences little to no resistance from patient tissue when moving from the open configuration toward the closed configuration. The jaws of the end effector continue to close around patient tissue from time $t_1$ to time $t_2$, over which time period the end effector begins to deliver bipolar energy 27930. The distance between the jaws of the end effector is less at time $t_1$ than at time $t_0$. From time $t_1$ to time $t_2$, the jaw motor velocity 27960 begins to slow down as the force to clamp 27950 the jaws of the end effector begins to increase.

As described with respect to FIGS. 16-29, a combination of monopolar energy 27935 and bipolar energy 27930 is delivered to patient tissue from time $t_2$ to time $t_3$. The jaws of the end effector continue to close around patient tissue during this time period. The distance between the jaws of the end effector is less at time $t_2$ than at time $t_1$. The particular distance between the jaws of the end effector at time $t_2$ indicates to the surgical instrument and/or the surgical hub that a tissue-warming phase of the surgical procedure has been reached and that a combination of monopolar and bipolar energies should be and/or is being delivered to the patient tissue. From time $t_2$ to time $t_3$, the jaw motor velocity continues to decrease and is less than the jaw motor velocity at $t_1$. The force required to clamp the jaws suddenly increases between time $t_2$ and time $t_3$, thereby confirming to the surgical instrument and/or the surgical hub that a combination of monopolar and bipolar energies is being delivered to the patient tissue.

Monopolar and bipolar energies continue to be delivered to the patient tissue, and the patient tissue is sealed from time $t_3$ to time $t_4$. As the end effector reaches its fully-closed configuration at time $t_3$, the force to clamp the jaws also reaches a maximum; however, the force to clamp the jaws remains stable between time $t_3$ and time $t_4$. The power level of the generator delivering monopolar energy increases between time $t_3$ and time $t_4$, while the power level of the generator delivering bipolar energy decreases between time $t_3$ and time $t_4$. Ultimately between time $t_4$ and $t_5$, monopolar energy is the only energy being delivered in order to cut the patient tissue. While the patient tissue is being cut, the force to clamp the jaws of the end effector may vary. In instances where the force to clamp the jaws decreases 27952 from its steady-state level maintained between time $t_3$ and $t_4$, an efficient and/or effective tissue cut is recognized by the surgical instrument and/or the surgical hub. In instances where the force to clamp the jaws increases 27954 from its steady-state level maintained between time $t_3$ and $t_4$, an inefficient and/or ineffective tissue cut is recognized by the surgical instrument and/or the surgical hub. In such instances, an error can be communicated to the user.

In various instances, the clamping operation of the jaws of the end effector can be adjusted based on a detected characteristic of contacted patient tissue. In various instances, the detected characteristic comprises tissue thickness and/or tissue type. For example, operations such as a range of gap distances between the jaws during a jaw closure stroke, a load threshold value, a rate of jaw closure, current limits applied during the jaw closure stroke, and/or a wait time between the jaw closure stroke and delivery of energy can be adjusted based on the detected thickness of patient tissue. In various instances, the detected characteristic of the contacted patient tissue can be used to adjust tissue weld parameters. More specifically, the detected characteristic can be used to adjust a multi-frequency sweep of impedance sensing, a balance and/or sequence of energy modality, an energy delivery level, an impedance shutoff level, and/or a wait time between energy level adjustments, for example.

As discussed in greater detail above, a surgical instrument and/or a surgical hub can utilize measured tissue characteristics to control and/or adjust an operational parameter of the surgical instrument. For example, tissue impedance can be detected as patient tissue is positioned between the jaws of an end effector. The detection of tissue impedance alerts the surgical instrument and/or the surgical hub that the jaws of the end effector are in contact with and/or near patient tissue. Referring now to FIG. 21, a graph 28000 illustrates the tissue impedance 28020 calculated over time 28010. When the jaws of the end effector are not in contact with patient tissue, the tissue impedance 28030a is infinite. As the jaws of the end effector are clamped around the patient tissue positioned therebetween, the patient tissue comes into contact with both jaws. In such instances, the tissue impedance 28030b is measureable. The ability to measure tissue impedance indicates to the surgical instrument and/or the surgical hub that patient tissue is appropriately positioned between the jaws of the end effector. The surgical instrument and/or the surgical hub can then initiate an operation, such as applying bipolar and/or monopolar energies to the patient tissue, for example.

In various instances, the surgical instrument and/or the surgical hub can utilize the magnitude of the detected tissue impedance to determine a phase of the surgical procedure. For example, as shown in FIG. 21, the tissue impedance 28030b is measured at a first level upon initial contact between the jaws of the end effector and the patient tissue. The surgical instrument can then begin to deliver bipolar energy to the patient tissue. Upon the detected tissue impedance 28030b increasing to and/or above a first pre-determined level, the surgical instrument begins to deliver a combination of bipolar and monopolar energies to the patient tissue to warm the patient tissue and/or to form a seal. As the detected tissue impedance 28030b continues to increase, the tissue impedance 28030b reaches and/or exceeds a second pre-determined level, at which point the surgical instrument ceases delivery of the bipolar energy while continuing to deliver monopolar energy to cut the patient tissue. Ultimately, the tissue impedance reaches an infinite level as the patient tissue is no longer positioned between the jaws of the end effector upon completion of the cut. In such instances, the surgical instrument and/or the surgical hub can cease delivery of the monopolar energy.

In various instances, strain can be a metric used to adjust operational parameters of the surgical instrument such as the clamping mechanism, for example. However, contact between the jaws of an end effector and patient tissue is desirable for an accurate estimation of compressive strain. As discussed in greater detail in reference to FIG. 21, a surgical instrument and/or a surgical hub can determine that contact exists between the jaws of the end effector and patient tissue by detected tissue impedance. FIG. 22 illustrates an end effector 28100 comprising a first jaw 28110 and a second jaw 28120, wherein the end effector is in an open configuration. A gap $D_0^A$ is defined between the first jaw 28110 and the second jaw 28120 in the open configuration. The jaws 28110, 28120 of the end effector 28100 are configured to receive patient tissue therebetween. At an initial time to, patient tissue $T_{A,0}$ is positioned in between the first jaw 28110 and the second jaw 28120. Notably, the patient tissue $T_{A,0}$ is in contact with both the first jaw 28110 and the second jaw 28120. Stated another way, a thickness of the patient tissue $T_{A,0}$ is greater than or equal to the gap $D_0^A$. As at least one of the first jaw 28110 and the second jaw 28120 move toward one another, the patient tissue compresses and the gap $D_1^A$ defined between the first jaw 28110 and the second jaw 28120 is reduced. The patient tissue $T_{A,1}$ is shown compressed between the first jaw 28110 and the second jaw 28120 at time $t_1$. The compressive strain can be calculated using the equation shown in FIG. 22. Because the patient tissue $T_{A,0}$ was in contact with the jaws 28110, 28120 of the end effector 28100 at time to, the applied strain is calculated accurately.

FIG. 23 illustrates the end effector 28100 of FIG. 22 in the open configuration. A gap $D_0^B$ is defined between the first jaw 28110 and the second jaw 28120 in the open configuration. The jaws 28110, 28120 of the end effector 28100 are configured to receive patient tissue therebetween. At an initial time to$_0$, patient tissue $T_{B,0}$ is positioned in between the first jaw 28110 and the second jaw 28120. However, unlike the patient tissue $T_{A,0}$, the patient tissue $T_{B,0}$ is not in contact with both the first jaw 28110 and the second jaw 28120. Stated another way, a thickness of the patient tissue $T_{B,0}$ is less than or equal to the gap $D_0^B$. As at least one of the first jaw 28110 and the second jaw 28120 move toward one another, the gap $D_1^B$ defined between the first jaw 28110 and the second jaw 28120 is reduced. The patient tissue $T_{B,1}$ is shown compressed between and/or in contact with the first jaw 28110 and the second jaw 28120 at time $t_1$. The compressive strain can be calculated using the equation shown in FIG. 23; however, the calculated compressive strain will be overestimated as the patient tissue $T_{B,0}$ was not in contact with the jaws 28110, 28120 of the end effector 28100 at time $t_0$.

As described above, calculating compressive strain by utilizing the gap defined between the first jaw and the second jaw of the end effector when the end effector is in the open configuration only leads to an accurate calculation when the patient tissue is in contact with both jaws of the end effector at an initial time to. Therefore, using the standard gap defined between the first jaw and the second jaw of the end effector when the end effector is in the open configuration is not desirable. Instead, the gap defined between the first jaw and the second jaw of the end effector when patient tissue initially contacts both jaws should be used when calculating compressive strain. An end effector is shown in the open configuration 28150 in FIG. 24. Notably, the patient tissue is not in contact with both end effector jaws 28110, 28120. Thus, no dimensions and/or specifications of the end effector in this configuration 28150 should be used in calculating compressive strain. As at least one of the first jaw 28110 and the second jaw 28120 continue to move toward one another, a gap $D_0^C$ is defined between the first jaw 28110 and the second jaw 28120. At an initial time $t_0$, patient tissue $T_{C,0}$ is positioned in between the first jaw 28110 and the second jaw 28120. Notably, the patient tissue $T_{C,0}$ is now in contact with both the first jaw 28110 and the second jaw 28120. Stated another way, a thickness of the patient tissue $T_{C,0}$ is greater than or equal to the gap D. As at least one of the first jaw 28110 and the second jaw 28120 continue to move toward one another, the patient tissue compresses and the gap $D_1^C$ defined between the first jaw 28110 and the second jaw 28120 is reduced. The patient tissue $T_{C,1}$ is shown compressed between the first jaw 28110 and the second jaw 28120 at time $t_1$. The compressive strain can be calculated using the equation shown in FIG. 24. As the patient tissue $T_{C,0}$ was in contact with the jaws 28110, 28120 of the end effector 28100 at time to and the gap $D_0^C$ defined between the first jaw 28110 and the second jaw 28120 at the point of initial tissue contact was realized, the applied strain is calculated accurately.

A motor control program of a combination electrosurgical instrument can utilize detected tissue stability as an input. The surgical instrument can detect compression rate and/or can measure the creep of the patient tissue compressed between end effector jaws to determine tissue stability. The control program can be modified to adjust wait times between end effector functions, define when to make an additional tissue stability determination, and/or adjust the rate of jaw clamping based on the determined tissue stability.

As shown in FIG. 25, an end effector 28250 comprises a first jaw 28254 and a second jaw 28256, wherein at least one of the first jaw 28254 and the second jaw 28256 is configured to move toward one another, wherein patient tissue T is configured to be positioned therebetween. FIG. 25 provides a schematic representation of the various positions of the first jaw 28254 and the second jaw 28256 with respect to patient tissue T during a jaw clamping stroke. The gap 28220*a* defined between the jaws of the end effector and the motor current 28220*b* required to clamp the jaws of the end effector vary over time 28210 due, at least in part, to tissue stability measurement. An initial slope $S_0$ corresponds to the jaw gap 28230 change between when the jaws are fully open to the point at which an initial contact is made between the jaws and the patient tissue T. The resulting motor current 28240 remains low while no tissue contact is present up until the end effector jaws contact the patient tissue T. The surgical system is configured to monitor the current 28220*b* over time 28210 to identify when the current slop flattens—i.e., when the tissue stabilizes. When the current slope flattens, the surgical system is configured to take the difference between the peak current at the time at which the end effector made initial contact with the tissue and the point at which the current flattens out. Stated another way, the jaws are able to continue clamping the tissue positioned therebetween when a wait time expires, wherein the wait time is defined by the time it takes for the tissue compression to stabilize. The creep of the motor current drives the next stage of motor current and velocity to the desired jaw gap, or level of tissue compression. The measurement of creep is repeated to drive next stages of motor current and velocity until the final jaw cap, or level of tissue compression, is achieved.

In addition to sensing parameters associated with the jaw clamping stroke, the surgical system can monitor additional functions to adjust and/or refine operational parameters of the surgical instrument. For example, the surgical system can monitor an orientation of the surgical instrument with respect to the user and/or the patient, the impedance of tissue positioned between the jaws of the end effector to determine tissue position and/or tissue composition, the level of grounding to the patient, and/or leakage current. Leakage current can be monitored to determine secondary leakage from other devices and/or to create parasitic generated energy outputs through capacitive coupling.

In various instances, a surgical instrument is configured to modify instrument and/or generator settings and/or control programs using local unsupervised machine learning. In such instances, the surgical instrument may update and/or adjust local functional behaviors based on a summarization and/or aggregation of data from various surgical procedures performed with the same surgical instrument. Such functional behaviors can be adjusted based on previous uses and/or preferences of a particular user and/or hospital. In such instances, a control program of the surgical instrument recognizes the same user and automatically modifies a default program with the preferences of the identified user. The surgical instrument is able to be updated by receiving regional and/or global updates and/or improvements of digitally enabled control programs and/or displayed information through interaction with a non-local server.

In various instances, a surgical instrument is configured to modify instrument and/or generator settings and/or control programs using global aggregation of instrument operational parameters and/or surgical procedure outcomes. A global surgical system is configured to collect data regarding related and/or contributing instrument parameters such as, for example, outcomes, complications, co-morbities, cost of surgical instrument, instrument utilization, procedure duration, procedure data, and/or patient data. The global surgical system is further configured to collect data regarding generator operation data such as, for example, impedance curves, power levels, energy modalities, event annotation, and/or adverse incidents. The global surgical system is further configured to collect data regarding intelligent device operation parameters such as, for example, clamp time, tissue pressure, wait times, number of uses, time of the patient on the operating table, battery levels, motor current, and/or actuation strokes. The global surgical system is configured to adapt default control programs and/or update existing control programs based on the detected operational parameters. In this way, each surgical instrument within the global surgical system is able to perform the most effective and/or efficient surgical procedures as possible.

FIG. 26 illustrates a network 28300 of surgical instruments 28310 that communicate with a cloud-based storage medium 28320. The cloud-based storage medium 28320 is configured to receive data relating to operational parameters from the surgical instrument 28310 that was collected over numerous surgical procedures. The data is used by the cloud-based storage medium 28320 to optimize control programs to achieve efficient and/or desirable results. The cloud-based storage medium 28320 is further configured to analyze all of the collected data in random batches 28340. The results of the analysis from the random batches 28340 can further be used in re-defining a control program. For example, the data collected within Batch A might be representative of significantly different wear profiles. A conclusion might then be able to be made from this data that suggests that instruments that adjust power rather than clamp current degrade faster, for example. The cloud-based storage medium 28320 is configured to communicate this finding and/or conclusion with the surgical instrument. The surgical instrument could then maximize the life of the instrument by adjusting clamp current instead of power and/or the surgical system could alert a clinician of this finding.

FIG. 26 illustrates a network 28300 of surgical instruments 28310 that communicate with a cloud-based storage medium 28320. The cloud-based storage medium 28320 is configured to receive data relating to operational parameters from the surgical instrument 28310 that was collected over numerous surgical procedures. The data is used by the cloud-based storage medium 28320 to optimize control programs to achieve efficient and/or desirable results. The cloud-based storage medium 28320 is further configured to analyze all of the collected data in random batches 28340. The results of the analysis from the random batches 28340 can further be used in re-defining a control program. For example, the data collected within Batch A might be representative of significantly different wear profiles. A conclusion might then be able to be made from this data that suggests that instruments that adjust power rather than clamp current degrade faster, for example. The cloud-based storage medium 28320 is configured to communicate this finding and/or conclusion with the surgical instrument. The surgical instrument could then maximize the life of the instrument by adjusting clamp current instead of power and/or the surgical system could alert a clinician of this finding.

The information gathered from the network 28300 of surgical instruments 28310 by the cloud-based storage medium 28320 is presented in graphical form in FIGS. 27 and 28. More specifically, a relationship between the gap 28430 defined between the jaws of the end effector from the point of initial tissue contact changes over time during a surgical procedure as a function of jaw motor clamp current 28440 is shown in FIG. 27. The number of times that a particular end effector has reached a fully-clamped state during the jaw clamping stroke impacts the amount of force needed to clamp the same thickness tissue. For example, the jaws of the end effector are able to clamp to a greater degree with less current for instruments fully-clamped 1-10 times 28430a than instruments fully-clamped 10-15 times 28430b. Furthermore, the jaws of the end effector are able to clamp to a greater degree with less current for instruments fully-clamped 10-15 times 28430b than instruments fully-clamped 16-20 times 28430c. Ultimately, more force, and therefore current, is needed to clamp the same thickness tissue to the same fully-clamped gap as the surgical instrument continues to be used. A control program can be modified using the collected information from the surgical instruments 28310 and the cloud-based storage medium 28320 to perform a more efficient and/or time-effective jaw clamping stroke.

The current required to clamp the same thickness tissue by achieving the same fully-clamped gap between the jaws of the end effector is used to set a motor current threshold for a generator. As shown in FIG. 28, the motor current threshold is lower for an end effector that has reached a fully-clamped state less than ten times, as less current is required to achieve the fully-clamped state. Thus, a control program sets a lower threshold generator power of newer end effectors than the threshold generator power of older end effectors. If the same generator power was used in an older end effector than what is used in a newer end effector, the tissue may not be sufficiently clamped and/or compressed between the jaws of the end effector. If the same generator power was used in a newer end effector that what is used in an older end effector, the tissue and/or the instrument may be damaged as the tissue may be over-compressed by the jaws of the end effector.

In various instances, a surgical system comprises modular components. For example, the surgical system comprises a surgical robot comprising robot arms, wherein the robot arms are configured to receive tools of different capabilities thereon. A control program of the surgical system is modified based on the modular attachments, such as the type of tools connected to the surgical robot arms, for example. In other instances, the surgical system comprises a handheld surgical instrument configured to receive different and/or replaceable end effectors thereon. Prior to performing an intended surgical function, the handheld surgical instrument is configured to identify the attached end effector and modify a control program based on the determined identity of the end effector.

The surgical system is configured to identify the attached modular component using adaptive and/or intelligent interrogation techniques. In various instances, the surgical system uses a combination of electrical interrogations in combination with a mechanical actuation interrogation to determine the capacities and/or the capabilities of an attached component. Responses to interrogations can be recorded and/or compared to information stored within a memory of the surgical system to establish baseline operational parameters associated with the identified modular attachment. In various instances, the established baseline parameters are stored within the memory of the surgical system to be used when the same or a similar modular attachment is identified in the future.

In various instances, an electrical interrogation signal is sent from a handle of a surgical instrument to an attached modular component, wherein the electrical interrogation signal is sent in an effort to determine an identity, an operational parameter, and/or a status of the attached modular component. The attached modular component is configured to send a response signal with the identifying information. In various instances, no response is received to the interrogation signal and/or the response signal comprises unidentifiable information. In such instances, a surgical instrument can perform a default function in order to assess the capabilities of the attached modular component. The default function is defined by conservative operational parameters. Stated another way, the default operational parameters used during a performance of the default function are defined to a particular level so as to avoid damage to the surgical instrument and/or the attached modular component, injury to the patient, and/or injury to the user. The surgical instrument is configured to utilize results of the default function in order to set an operating program specific to the attached modular component.

For example, a surgical instrument can perform a tissue cutting stroke, wherein a cutting member traverses through an attached end effector from a proximal position toward a distal position. In instances where the surgical instrument is unable to identify the attached end effector, the surgical instrument is configured to perform the tissue cutting stroke using the default operational parameters. Utilizing a position of the cutting member within the end effector at the end of the tissue cutting stroke, the surgical instrument can determine a length of the tissue cutting stroke associated and/or appropriate for completion with the attached end effector. The surgical instrument is configured to record the distal-most position of the cutting member in order to set additional operational parameters associated with the attached end effector. Such additional operational parameters include, for example, a speed of the cutting element during the tissue cutting stroke and/or the length of the end effector.

The default function can also be used to determine a current state and/or status of the attached modular component. For example, the default function can be performed to determine if the attached end effector is articulated and/or to what degree the attached end effector is articulated. The surgical instrument is then configured to adjust a control program accordingly. A length of the cutting stroke changes as the end effector is articulated across a range of articulation angles. Stated another way, the length of the cutting stroke is different when the end effector is in articulated state as compared to when the end effector is in an unarticulated state. The surgical instrument is configured to update a control program to perform cutting strokes spanning the length associated with the last detected full stroke. The surgical instrument is further configured to use the length of the last completed cutting stroke to determine if the full length of the cutting stroke is accomplished and/or completed with the current control program when the end effector is unarticulated compared to when the end effector is articulated.

In various instances, the surgical system can perform an intelligent assessment of a characteristic of the attached component. Such a characteristic includes, for example, tissue pad wear, degree of attachment usage, and/or operating condition of the attachment. Stated another way, the surgical system is configured to assess the functionality and/or condition of the attached component. Upon detecting the characteristic of the attached modular component, a control program used to operate the surgical system is adjusted accordingly.

A surgical instrument comprises one or more tissue pads positioned on the jaws of an end effector. It is generally well known that tissue pads tend to degrade and wear over time due to frictional engagement with a blade when no tissue is present therebetween, for example. The surgical instrument is configured to determine a degree of tissue pad wear by analyzing the remaining tissue pad thickness and/or stiffness, for example. Utilizing the determined status of the tissue pad(s), the surgical instrument adjusts a control program accordingly. For example, the control program can alter an applied pressure and/or a power level of the surgical instrument based on the determined status of the tissue pad(s). In various instances, the power level of the surgical instrument can be automatically reduced by a processor of the surgical instrument in response to a detected thickness of the tissue pad(s) that is less than a threshold thickness.

A surgical instrument comprises a combination electrosurgical functionality, wherein the surgical instrument includes an end effector comprising a first jaw and a second jaw. At least one of the first jaw and the second jaw is configured to move toward one another to transition the end effector between an open configuration and a closed configuration. The first jaw and the second jaw comprise electrodes disposed thereon. The electrosurgical instrument comprises one or more power generators configured to supply power to the electrodes to energize the electrodes. The surgical instrument can assess a degree of charring and/or tissue contamination on one or more of the end effector jaws by measuring an impedance when the end effector is in the closed configuration without any patient tissue positioned therebetween. A pre-determined impedance can be stored within a memory of the surgical instrument, wherein if the impedance exceeds the pre-determined threshold, the jaws comprise an undesirable level of char and/or tissue contamination thereon. As discussed in greater detail herein, an alert can be issued to a user upon detection of an undesirable level of char. In various instances, an operational parameter can automatically be adjusted by a processor of the surgical instrument and/or a surgical hub in response to the detected closed jaw impedance. Such operational parameters include power level, applied pressure level, and/or advanced tissue cutting parameters, for example.

As shown in FIG. 29, a graphical representation 28500 illustrates a relationship 28530 between the measured impedance 28250 and a number of activation cycles 28510. A baseline impedance is measured and recorded within the memory prior to any energy activation (n=0 activations). As discussed above, the impedance is measured when the end effector of the surgical instrument is in the closed configuration and no patient tissue is positioned therebetween. The surgical instrument and/or a surgical hub prompts a user to transition the end effector into the closed configuration for the closed jaw impedance to be measured. Such prompts can be delivered at pre-defined activation intervals, such as n=5, 10, 15, etc., for example. As char and/or tissue contamination accumulate on the jaws of the end effector, impedance increases. At and/or above a first pre-determined level 28540, the surgical instrument and/or the surgical hub is configured to alert the user of such char accumulation and advise the user to clean the end effector. At and/or above a second pre-determined level 28550, the surgical instrument and/or the surgical hub can prevent the user from using various operational functions of the surgical instrument until the end effector is cleaned. The operational lockout can be removed upon cleaning of the end effector, assuming that the measured impedance has reduced to an acceptable level.

As discussed above, the surgical hub and/or the surgical instrument is configured to alert a user when a pre-determined impedance is met and/or exceeded. Such an alert can be communicated through various forms of feedback, including, for example, haptic, acoustic, and/or visual feedback. In at least one instance, the feedback comprises audio feedback, and the surgical instrument can comprise a speaker which emits a sound, such as a beep, for example, when an error is detected. In certain instances, the feedback comprises visual feedback and the surgical instrument can comprise a light emitting diode (LED), for example, which flashes when an error is detected. In certain instances, the visual feedback can be communicated to a user through an alert presented on a display monitor within a field of vision of the user. In various instances, the feedback comprises haptic feedback, and the surgical instrument can comprise an electric motor comprising an eccentric element which vibrates when an error is detected. The alert can be specific or generic. For example, the alert can specifically state that the closed jaw impedance exceeded a pre-determined level, or the alert can specifically state the measured impedance.

In various instances, the surgical instrument and/or the surgical hub is configured to detect parameters such as integral shaft stretch, damage, and/or tolerance stack up to compensate for functional parameter operations of motorized actuators. The surgical instrument is configured to alert a user when a detected parameter of the attached end effector and/or shaft is close to being and/or is outside of desirable operating ranges specific to the attached component. In addition to alerting the user, in various instances, operation of the surgical instrument is prevented when it has been detected that the surgical instrument is incapable of operating within a pre-defined envelope of adjustment. The surgical instrument and/or the surgical hub comprises an override, wherein the user is allowed to override the lockout in certain pre-defined conditions. Such pre-defined conditions include an emergency, the surgical instrument is currently in use during a surgical procedure where the inability to use the surgical instrument would result in harm to the patient, and a single use override to allow for one additional use of the surgical instrument at the discretion of the user. In various instances, an override is also available to allow a user to perform a secondary end effector function that is unrelated to a primary end effector function. For example, if a surgical instrument prevents the jaws of the end effector from being articulated, the user may activate the override to allow the surgical instrument to articulate the end effector.

A surgical system can adapt a control program configured to operate a surgical instrument in response to a detected instrument actuation parameter, an energy generator parameter, and/or a user input. A determined status of the surgical instrument is used in combination with the user input to adapt the control program. The determined status of the surgical instrument can include whether an end effector is in its open configuration, whether an end effector is in its closed configuration and/or whether a tissue impedance is detectable, for example. The determined status of the surgical instrument can include more than one detected characteristic. For example, the determined status of the surgical instrument can be assessed using a combination of two or more measures, a series of ordered operations, and/or interpretations of a familiar user input based on its situational usage. The control program is configured to adjust various functions of the surgical instrument such as the power level, an incremental step up or step down of power, and/or various motor control parameters, for example.

A surgical system comprises a surgical instrument including a combination electrosurgical functionality, wherein the surgical instrument includes an end effector comprising a first jaw and a second jaw with electrodes disposed thereon. The electrosurgical instrument comprises one or more power generators configured to supply power to the electrodes to energize the electrodes. More specifically, energy delivery to patient tissue supported between the first jaw and the second jaw is achieved by the electrodes which are configured to deliver energy in a monopolar mode, bipolar mode, and/or a combination mode with alternating or blended bipolar and monopolar energies. As described in greater detail herein, the surgical system can adapt a level of energy power activation of the one or more generators based on various monitored parameters of the surgical instrument.

The surgical system is configured to adapt energy power activation based on instrument monitored parameters. In various instances, the surgical system can monitor the sequence in which various surgical instrument functions are activated. The surgical system can then automatically adjust various operating parameters based on the activation of surgical instrument functions. For example, the surgical system can monitor the activation of rotation and/or articulation controls and prevent the ability for the surgical instrument to deliver energy to patient tissue while such secondary non-clamp controls are in use.

In various instances, the surgical system can adapt instrument power levels to compensate for detected operating parameters such as inadequate battery and/or motor drive power levels, for example. The detection of inadequate battery and/or motor drive power levels can indicate to the surgical system that clamp strength of the end effector is impacted and/or impaired, thereby resulting in undesirable control over the patient tissue positioned therebetween, for example.

The surgical system can record operating parameters of the surgical instrument during periods of use that are associated with a particular intended function. The surgical system can then use the recorded operating parameters to adapt energy power levels and/or surgical instrument modes, for example, when the surgical system identifies that the particular intended function is being performed. Stated another way, the surgical system can automatically adjust energy power levels and/or surgical instrument modes with stored preferred operating parameters when a desired function of the surgical instrument is identified and/or the surgical instrument can adjust energy power levels and/or surgical instrument modes in an effort to support and compliment the desired function. For example, a surgical system can supplement a detected lateral loading on the shaft with application of monopolar power, as detected lateral loading on the shaft often results from abrasive dissection with the end effector in its closed configuration. The surgical system decided to apply monopolar power, as the surgical system is aware, through previous procedures and/or through information stored in the memory, that monopolar power results in improved dissection. In various instances, the surgical system is configured to apply the monopolar power proportionate to increases in the detected lateral load.

The surgical system can adapt a control program configured to operate a surgical instrument in response to a detected end effector parameter. As shown in FIG. 30, a surgical instrument can utilize measured tissue conductance to automatically modify a gap clamp control program. Tissue conductance is measured at two frequencies such as 50 kHz and 5 MHz, for example. Low frequency conductance (GE) is driven by extracellular fluid, whereas high frequency conductance (GI) is driven by intracellular fluid. The intracellular fluid levels change through as cells become damaged, for example. The end effector is configurable in an open configuration and a closed configuration. Thus, as the end effector is motivated from its open configuration toward its closed configuration, the jaws of the end effector compress the tissue positioned therebetween. During the tissue compression, changes in the conductance between the two frequencies can be detected and/or recorded. The surgical system is configured to adapt the control program to control end effector clamp compression based on the ratio of low frequency conductance (GE) to high frequency conductance (GI). The surgical system adapts the control program until a discrete pre-determined point and/or until an inflection point is approached, whereby the pre-determined point and/or the inflection point indicate that cellular damage could be near.

More specifically, FIG. 30 is a graphical representation 29000 of relationships between measured tissue conductance 29100, a ratio of low frequency conductance to high frequency conductance 29200, dimension of jaw aperture 29300, and jaw motor force 29400 over the duration 29010 of a jaw clamp stroke. At the beginning of the jaw clamp stroke, measured tissue conductance is at its lowest as the jaws of the end effector initially come into contact with patient tissue, and the jaw aperture 29300 is at its largest value when the end effector is in its open configuration. Due, at least in part, to the small amount of resistance provided against the jaws from the tissue positioned therebetween, the jaw motor force is low at the beginning of the jaw clamp stroke. Prior to compression, but after contact between the patient tissue and the jaws of the end effector, the low frequency conductance 29110 increases indicating the presence of extracellular fluid within the captured tissue. Similarly, prior to compression, but after contact between the patient tissue and the jaws of the end effector, the high energy conductance 29120 increases indicating the presence of intracellular fluid.

As the end effector begins to move toward its closed configuration, the jaws of the end effector begin to clamp the tissue positioned therebetween, and thus, the jaw aperture 29300 continues to decrease. The tissue begins to be compressed by the jaws; however until fluid begins to expel from the compressed tissue, the patient tissue is not desirable to be sealed by the surgical instrument. The jaw motor force continues to increase during the jaw clamp stroke, as increased resistance is expelled against the end effector jaws by the captured tissue.

After the initial expulsion of extracellular fluid causes a decrease in the low frequency conductance (GE) 29110, the low frequency conductance (GE) 29110 remains relatively constant during the jaw clamp stroke. The high frequency conductance (GI) 29120 remains relatively constant during the jaw clamp stroke until after the patient tissue is sealed. As the tissue continues to be compressed after the seal is completed, intracellular tissue damage occurs and the intracellular fluid is expelled. At such point, the high frequency conductance 29120 decreases, causing a spike in the ratio 29210 of low frequency conductance to high frequency conductance. A tissue damage threshold 29220 is predetermined to alert a user and/or automatically prompt the surgical system to modify operational parameters when the spike in the ratio 29210 of low frequency conductance to high frequency conductance reaches and/or exceeds the tissue damage threshold 29220. At such point, the surgical system is configured to modify the control program to stop motivating the jaws of the end effector toward the closed configuration of the end effector and/or begin motivating the jaws of the end effector back toward the open configuration of the end effector. In various instances, the surgical system is configured to modify the control program to reduce the jaw clamp force. Such adaptation of the control program prevents additional tissue damage.

A surgical system is configured to modify a control program based on cooperative dual inputs. More specifically, a surgical system can vary a motor actuation rate based on a user input and pre-defined settings. For example, the more force that a user applies to a handle control, the faster the motor is actuated to trigger the system. In various instances, a handle control can be used to communicate different commands to the surgical system depending on its situational usage. More specifically, the surgical system can monitor and/or record a particular user input. The particular user input can be analyzed for its length, duration, and/or any suitable characteristic that can be used to distinguish the input. For example, a handle of a surgical instrument can include a trigger, wherein the trigger is configured to control shaft rotation. In various instances, faster actuation of the trigger corresponds to an increase in the rate at which the shaft is rotated; however, the maximum force (current) threshold of the motor remains constant. In other instances, faster actuation of the triggers corresponds to an increase in force being applied while a rotation speed threshold remains the same. Such control can be further differentiated by the shaft rotation speed being increased based on the duration that a user actuates the trigger while the force is based on the rate at which the trigger is actuated.

In various instances, motor actuation control is based on a combination of a pre-defined setting and a detection of an instrument operating parameter and/or a user control parameter. FIG. 31 is a graphical representation 29500 of the relationship between actual jaw closure speed 29520 and a trigger speed indicated by a user input 29510. The jaw closure speed 29520 resulting solely from a corresponding user input 29510 is represented by a first line 29530. As the user input trigger speed 29510 increases, the jaw closure speed 29520 also increases. Such a relationship 29530 is determined without the consideration of any additional parameters. The jaw closure speed 29520 resulting from a corresponding user input 29510 and a determination of thick tissue positioned between the jaws of the end effector is represented by a second line 29540. As the user input trigger speed 29510 increases, the jaw closure speed 29520 also increases; however, the jaw closure speed 29520 is less than if the user input trigger speed was being considered alone. The additional consideration of tissue thickness slows the jaw closure speed down in order to prevent damage to the patient tissue and/or the surgical instrument, for example.

A surgical system comprises numerous components. For example, the surgical system comprises numerous handheld surgical instruments, a surgical hub, and a surgical robot. In various instances, each component of the surgical system is in communication with the other components and can issue commands and/or alter a control program based on at least one monitored parameter and/or a user input. The surgical system comprises means to determine which system is in charge and which system makes portions of operational decisions. This designation can be changed based on situational awareness, the occurrence of pre-determined events, and/or the exceedance of thresholds. In various instances, a command protocol can be established within the surgical system to indicate a type of command each component is able to issue and/or to which components within the surgical system the issuing component can direct a command.

The command protocol can use pre-defined thresholds to determine when a control hand-off is warranted. For example, the surgical system comprises a generator and a handheld surgical instrument including various controls therein. At the beginning of a surgical procedure, the generator is initially in control and adjusts the power based on detected impedance. The generator uses the detected impedance and/or the current power level to command a pressure control within a handle of the surgical instrument to follow specific pressure needs. At a point during the surgical procedure, a lower impedance threshold is exceeded indicative that the generator algorithm has detected an electrical short. The generator passes control to the pressure control within the handle by instructing the pressure control to determine if tissue is still positioned between the jaws of the end effector. The pressure control is then able to determine an appropriate tissue compression and can communicate what power level and/or energy modality is most appropriate for the detected tissue.

The control protocol can be determined based on a consensus reached by a plurality of the components within the surgical system. For example, three components within the surgical system detect a first value relating to a monitored parameter while two components within the surgical system detect a second value relating to the same monitored parameter, wherein the first value and the second value are different. The group of three components comprise more components than the group of two components, and thus, the first value of the monitored parameter controls. Each component within the surgical system can be assigned a positioned within a hierarchy. The hierarchy can be established based on reliability of the particular component and/or the capabilities of the particular component. A first component detects a first value relating to a monitored parameter, and a second component detects a second value relating to the same monitored parameter, wherein the first value is different than the second value. The second component "outranks" the first component within the hierarchy of the surgical system, and thus, the second value of the monitored parameter detected by the second component controls.

Various aspects of the subject matter described herein are set out in the following examples.

EXAMPLE SET 1

Example 1

A surgical system comprising a surgical instrument, a generator configured to supply power to an end effector, and a processor configured to run a control program to operate the surgical system. The surgical instrument comprises the end effector that includes a first jaw and a second jaw. At least one of the first jaw and the second jaw is moved with respect to one another between an open position and a closed position. Tissue is configured to be positioned between the first jaw and the second jaw. The processor is configured to detect a first parameter of the surgical system, detect at least one user input, and modify the control program in response to the detected first parameter and the at least one user input.

Example 2

The surgical system of Example 1, wherein the control program is configured to control a power level of the generator.

Example 3

The surgical system of Examples 1 or 2, wherein the control program is configured to control a motor, wherein the motor is configured to cause the end effector to move between the open configuration and the closed configuration.

Example 4

The surgical system of Example 3, wherein the control program is configured to control the motor through motor control parameters, and wherein the control program is configured to adjust the motor control parameters in response to the detected first parameter and the detected user input.

Example 5

The surgical system of Examples 1, 2, 3, or 4, wherein the first parameter comprises an instrument actuation parameter.

Example 6

The surgical system of Examples 1, 2, 3, 4, or 5, wherein the first parameter comprises a generator operating parameter.

Example 7

The surgical system of Examples 1, 2, 3, 4, 5, or 6, wherein the first parameter comprises a status of the end effector.

Example 8

The surgical system of Examples 1, 2, 3, 4, 5, 6, or 7, wherein the first parameter indicates whether the end effector is in the open configuration or the closed configuration.

Example 9

The surgical system of Examples 1, 2, 3, 4, 5, 6, or 7, wherein the first parameter indicates whether the tissue is positioned between the first jaw and the second jaw.

Example 10

The surgical system of Examples 1, 2, 3, 4, 5, 6, 7, 8, or 9, wherein the surgical instrument is in operational control, and wherein the generator is a slave control system by default.

Example 11

The surgical system of Examples 1, 2, 3, 4, 5, 6, 7, 8, or 9, wherein the control program is configured to cause the generator to be in operational control and the surgical instrument to be the slave control system in response to the detected first parameter and the detected user input.

Example 12

The surgical system of Examples 1, 2, 3, 4, 5, 6, 7, 8, 9, 10, or 11, wherein the first parameter comprises a combination of two measures.

Example 13

The surgical system of Examples 1, 2, 3, 4, 5, 6, 7, 8, 9, 10, 11, or 12, wherein the surgical system further comprises a trigger configured to receive the user input, wherein the processor is configured to interpret multiple user inputs received by the trigger, wherein each user input comprises a different meaning based on situational usage.

Example 14

A surgical system comprising a surgical instrument, a generator configured to supply power to the surgical instrument, and a processor configured to run a control program to operate the surgical system. The processor is configured to detect a status of the surgical instrument, detect at least one user input, and adapt the control program in response to the detected status of the surgical instrument and the at least one user input.

Example 15

The surgical system of Example 14, wherein the surgical instrument comprises an end effector, wherein the end effector is configurable in an open configuration and a closed configuration, and wherein the status of the surgical instrument corresponds to whether the end effector is in the open configuration or the closed configuration.

Example 16

The surgical system of Examples 14 or 15, wherein the surgical instrument comprises an end effector, wherein the end effector is configurable in an open configuration and a closed configuration, and wherein the status of the surgical instrument corresponds to whether patient tissue is positioned between the first jaw and the second jaw.

Example 17

The surgical system of Examples 14, 15, or 16, wherein the surgical system further comprises an input member configured to receive the user input, wherein the processor is configured to interpret multiple user inputs received by the input member, wherein each received user input comprises a different meaning based on situational usage of the surgical system.

Example 18

A surgical system comprising a surgical instrument, a generator configured to supply power to an end effector, and a processor configured to run a control program to operate the surgical system. The surgical instrument comprises the end effector which includes a first jaw and a second jaw. At least one of the first jaw and the second jaw is moved with respect to one another between an open position and a closed position. Tissue is configured to be positioned between the first jaw and the second jaw. The processor is configured to detect a first parameter of the surgical instrument, detect a second parameter of the generator, detect at least one user input, and modify the control program in response to the detected first parameter, the detected second parameter, and the at least one user input.

Example 19

The surgical system of Example 18, wherein the first parameter of the surgical instrument corresponds to whether the end effector is in the open configuration or the closed configuration and whether patient tissue is positioned between the first jaw and the second jaw.

Example 20

The surgical system of Examples 18 or 19, wherein the surgical instrument further comprises an input member configured to receive the user input, wherein the processor is configured to interpret multiple user inputs received by the input member, wherein each received user input comprises a different meaning based on situational usage of the surgical instrument within the surgical system.

EXAMPLE SET 2

Example 1

A surgical instrument comprising a housing, a shaft assembly, a processor, and a memory. The shaft assembly is replaceably connected to the housing. The shaft assembly comprises an end effector. The memory is configured to store program instructions which, when executed from the memory cause the processor to send an electrical interrogation signal to the attached shaft assembly, receive a response signal from the attached shaft assembly, cause a default function to be performed when a response signal is not received by the attached shaft assembly, determine an identifying characteristic of the attached shaft assembly as a result of the performance of the default function, and modify a control program based on the identifying characteristic of the attached shaft assembly.

Example 2

The surgical instrument of Example 1, wherein the identifying characteristic comprises remaining capacity of the attached shaft assembly.

Example 3

The surgical instrument of Examples 1 or 2, wherein the identifying characteristic comprises a performance level of the attached shaft assembly.

Example 4

The surgical instrument of Examples 1, 2, or 3, wherein the identifying characteristic is different for attached shaft assemblies of different capabilities.

Example 5

The surgical instrument of Example 1, 2, 3, or 4, wherein the memory comprises a lookup table comprising operating parameters corresponding to particular shaft assemblies, wherein the processor utilizes the received response signal to identify the attached shaft assembly within the lookup table, and wherein the control program is modified using the stored operating parameters corresponding to the identified shaft assembly.

Example 6

The surgical instrument of Examples 1, 2, 3, 4, or 5, wherein the memory further comprises program instructions which, when executed, cause the processor to store the modified control program in the memory.

Example 7

A surgical instrument comprising a housing, a shaft assembly, a processor, and a memory. The shaft assembly is replaceably connected to the housing. The shaft assembly comprises an end effector. The memory is configured to store program instructions which, when executed from the memory cause the processor to send a variable interrogative communication to the attached shaft assembly, determine a capability of the attached shaft assembly based on a response to the variable interrogative communication, and modify a control program based on the determined capability of the attached shaft assembly.

Example 8

The surgical instrument of Example 7, wherein the variable interrogative communication comprises an electrical interrogation signal and a physical actuation of the surgical instrument.

Example 9

The surgical instrument of Examples 7 or 8, wherein the physical actuation of the surgical instrument is monitored to determine a functional capability of the attached shaft assembly.

Example 10

The surgical instrument of Examples 7, 8, or 9, wherein the determined capability relates to a remaining capacity of the shaft assembly.

Example 11

The surgical instrument of Examples 7, 8, 9, or 10, wherein the determined capability relates to a performance level of the shaft assembly.

Example 12

The surgical instrument of Examples 7, 8, 9, 10, or 11, wherein the capability to be determined differs based on the connected shaft assembly.

Example 13

The surgical instrument of Examples 7, 8, 9, 10, 11, or 12, wherein the memory further comprises further comprises program instructions which, when executed, cause the processor to store the modified control program and the determined shaft assembly capability in the memory.

Example 14

A surgical instrument comprising a housing, a shaft assembly, a processor, and a memory. The shaft assembly is interchangeably coupled to the housing. The shaft assembly comprises an end effector. The memory is configured to store program instructions which, when executed from the memory, cause the processor to send an interrogation signal to the shaft assembly coupled to the housing, receive a response signal from the shaft assembly coupled to the housing, cause a default end effector function to be performed when a response signal is not recognized, determine an identifying characteristic of the shaft assembly coupled to the housing as a result of the performance of the default end effector function, and modify a control program based on the identifying characteristic of the shaft assembly coupled to the housing.

Example 15

The surgical instrument of Example 14, wherein the response signal is not recognized by the processor because the response signal is not received by the processor.

Example 16

The surgical instrument of Examples 14 or 15, wherein the identifying characteristic comprises remaining capacity of the shaft assembly coupled to the housing.

Example 17

The surgical instrument of Examples 14, 15, or 16, wherein the identifying characteristic comprises a performance level of the shaft assembly coupled to the housing.

Example 18

The surgical instrument of Examples 14, 15, 16, or 17, wherein the determined characteristic can differ based on the shaft assembly interchangeably coupled to the housing.

Example 19

The surgical instrument of Examples 14, 15, 16, 17, or 18, wherein the memory comprises a lookup table comprising operating parameters corresponding to particular shaft assemblies, wherein the processor utilizes the received response signal to identify the shaft assembly coupled to the housing within the lookup table, and wherein the control program is modified using the stored operating parameters corresponding to the identified shaft assembly.

Example 20

The surgical instrument of Examples 14, 15, 16, 17, 18, or 19, wherein the memory further comprises program instructions which, when executed, cause the processor to store the modified control program in the memory.

EXAMPLE SET 3

Example 1

A surgical system comprising a surgical hub, a surgical instrument, a generator configured to energize an end effector; and a smoke evacuation system configured to remove smoke from a surgical site. The surgical instrument comprises the end effector. A control command is passed directly from the surgical hub to the surgical instrument. The surgical instrument is configured to pass the control command received from the surgical hub to the generator and the smoke evacuation system in a daisy-chain manner.

Example 2

The surgical system of Example 1, wherein the surgical instrument is configured to modify the control command with a parameter detected by the surgical instrument.

Example 3

The surgical system of Example 2, wherein the surgical instrument is configured to pass the modified control command to the generator.

Example 4

The surgical system of Examples 2 or 3, wherein an operating parameter of the generator is controlled by the modified control command.

Example 5

The surgical system of Examples 2, 3, or 4, wherein the generator is configured to alter the modified control command with a second parameter detected by the generator.

Example 6

The surgical system of Examples 2, 3, 4, or 5, wherein the surgical instrument is configured to pass the modified control command to the surgical hub, and wherein the surgical hub is configured to pass the modified control command to the generator.

Example 7

The surgical system of Example 1, wherein the surgical instrument detects a first parameter of the surgical instrument, wherein the surgical instrument is configured to communicate the detected first parameter to the generator, and wherein generator is configured to modify the control command with the first parameter.

Example 8

The surgical system of Example 1, wherein the surgical instrument detects a first parameter of the surgical instrument, wherein the surgical instrument is configured to communicate the detected first parameter to the generator, wherein the generator detects a second parameter, and wherein the generator is configured to modify the control command with the first parameter and the second parameter.

Example 9

The surgical system of Examples 1, 2, 3, 4, 5, 6, 7, or 8, further comprising a display screen configured to display a live feed of a surgical site and a first operating parameter of the surgical instrument.

Example 10

The surgical system of Example 9, wherein the surgical instrument further comprises an instrument display configured to display a second operating parameter of the surgical instrument, and wherein the first operating parameter is the same as the second operating parameter.

Example 11

The surgical system of Example 9, wherein the surgical instrument further comprises an instrument display configured to display a second operating parameter of the surgical instrument, and wherein the first operating parameter is different than the second operating parameter.

Example 12

The surgical system of Examples 9, 10, or 11, wherein the display screen is further configured to display an operating parameter of the generator.

Example 13

A surgical system comprising a surgical hub, a surgical instrument, a generator configured to energize an end effector, and a smoke evacuation system configured to remove smoke from a surgical site. The surgical instrument comprises the end effector. A control command is passed directly from the surgical hub to the surgical instrument. The surgical instrument is configured to pass the control command received from the surgical hub to the generator and the smoke evacuation system.

Example 14

The surgical system of Example 13, wherein the surgical instrument is configured to pass the control command received from the surgical hub to the generator and the smoke evacuation system in a daisy-chain manner.

Example 15

A surgical system comprising a surgical hub, a first surgical instrument, a first generator configured to energize a first end effector, and a second surgical instrument. The first surgical instrument comprises the first end effector. A control command is passed directly from the surgical hub to the first surgical instrument. The first surgical instrument is configured to pass the control command received from the surgical hub to the first generator and the second surgical instrument in a daisy-chain manner.

Example 16

The surgical system of Example 15, wherein the first surgical instrument is configured to modify the control command with a first parameter detected by the first surgical instrument.

Example 17

The surgical system of Example 16, wherein the first surgical instrument is configured to pass the modified control command to the second surgical instrument.

Example 18

The surgical system of Example 17, wherein the second surgical instrument is configured to alter the modified control command with a second parameter detected by the second surgical instrument, and wherein the second surgical instrument is configured to pass the altered control command to the first surgical instrument.

Example 19

The surgical system of Example 15, wherein the first surgical instrument is configured to detect a first parameter, wherein the second surgical instrument is configured to detect a second parameter, wherein the second surgical instrument is configured to communicate the detected second parameter to the first surgical instrument, and wherein the first surgical instrument is configured to modify the control command with the first parameter detected by the first surgical instrument and the second parameter detected by the second surgical instrument.

Example 20

The surgical system of Examples 15, 16, 17, 18, or 19, wherein the second surgical instrument comprises a smoke evacuation system configured to remove smoke from a surgical site.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical system, comprising:
a surgical hub comprising a hub processor configured to provide a first signal;
a surgical instrument comprising an end effector, a sensor, and an instrument processor, wherein the instrument processor is to receive, from the surgical hub, the first signal;
an electrosurgical generator comprising a generator processor, wherein the electrosurgical generator is configured to energize the end effector, wherein the instrument processor is configured to communicate, to the electrosurgical generator, a second signal; and
a smoke evacuation system configured to remove smoke from a surgical site, wherein the generator processor is configured to communicate, to the smoke evacuation system, a third signal; wherein the surgical hub, the surgical instrument, the electrosurgical generator, and the smoke evacuator system are configured to communicate in a daisy-chain manner.

2. The surgical system of claim 1, wherein the surgical instrument is configured to modify the second signal based on a parameter of the end effector detected by the sensor of the surgical instrument.

3. The surgical system of claim 2, wherein the surgical instrument is configured to communicate the modified second signal to the electrosurgical generator.

4. The surgical system of claim 3, wherein an operating parameter of the electrosurgical generator is controlled by the modified second signal.

5. The surgical system of claim 3, wherein the electrosurgical generator is configured to alter the modified second signal with a second parameter detected by the electrosurgical generator.

6. The surgical system of claim 2, wherein the surgical instrument is configured to communicate the modified second signal to the surgical hub, and wherein the surgical hub is configured to communicate the modified second signal to the electrosurgical generator.

7. The surgical system of claim 1, wherein the sensor of the surgical instrument is configured to detect a first parameter of the end effector, wherein the instrument processor is configured to communicate the detected first parameter to the electrosurgical generator, and wherein the generator processor is configured to modify the first signal based on the first parameter.

8. The surgical system of claim 1, wherein the surgical instrument sensor is configured to detect a first parameter of the end effector of the surgical instrument, wherein the instrument processor is configured to communicate the detected first parameter to the electrosurgical generator, wherein the electrosurgical generator detects a second parameter, and wherein the electrosurgical generator is configured to modify the third signal with the first parameter and the second parameter.

9. The surgical system of claim 1, further comprising a display screen configured to display a live feed of a surgical site and a first operating parameter of the surgical instrument.

10. The surgical system of claim 9, wherein the surgical instrument further comprises an instrument display configured to display a second operating parameter of the surgical instrument, and wherein the first operating parameter is the same as the second operating parameter.

11. The surgical system of claim 9, wherein the surgical instrument further comprises an instrument display configured to display a second operating parameter of the surgical instrument, and wherein the first operating parameter is different than the second operating parameter.

12. The surgical system of claim 9, wherein the display screen is further configured to display an operating parameter of the electrosurgical generator.

13. A surgical system, comprising:
a surgical hub comprising a hub processor configured to provide a first signal;
a surgical instrument comprising an end effector, a sensor, and an instrument processor, wherein the instrument processor is to receive, from the surgical hub, the first signal;
an electrosurgical generator comprising a generator processor, wherein the electrosurgical generator is to energize the end effector, wherein the instrument processor is configured to communicate, to the electrosurgical generator, a second signal; and a smoke evacuation system configured to remove smoke from a surgical site, wherein the generator processor is configured to communicate, to the smoke evacuation system, a third signal.

14. The surgical system of claim 13, wherein the first signal, the second signal, and the third signal are communicated in a daisy-chain manner.

15. A surgical system, comprising:
a surgical hub comprising a hub processor configured to provide a first signal;
a first surgical instrument comprising a first end effector and a first processor, wherein the first processor is to receive, from the surgical hub, the first signal;
a first electrosurgical generator comprising a first generator processor, wherein the first electrosurgical generator is to energize the first end effector, wherein the first processor of the first surgical instrument is to communicate, to the first electrosurgical generator, a second signal; and
a second surgical instrument, wherein the first generator processor is configured to communicate, to the second surgical instrument, a third signal;
wherein the surgical hub, the first surgical instrument, the first electrosurgical generator, and the second surgical instrument are configured to communicate in a daisy-chain manner.

16. The surgical system of claim 15, wherein the first surgical instrument is configured to modify the second signal with a first parameter detected by the first surgical instrument.

17. The surgical system of claim 16, wherein the first surgical instrument is configured to convey the modified second signal to the second surgical instrument.

18. The surgical system of claim 17, wherein the second surgical instrument is configured to alter the modified second signal with a second parameter detected by the second surgical instrument, and wherein the second surgical instrument is configured to convey the modified second signal to the first surgical instrument.

19. The surgical system of claim 15, wherein the first surgical instrument is configured to detect a first parameter, wherein the second surgical instrument is configured to detect a second parameter, wherein the second surgical instrument is configured to communicate the detected second parameter to the first surgical instrument, and wherein the first surgical instrument is configured to modify the second signal with the first parameter detected by the first surgical instrument and the second parameter detected by the second surgical instrument.

20. The surgical system of claim 15, wherein the second surgical instrument comprises a smoke evacuation system configured to remove smoke from a surgical site.

* * * * *